United States Patent [19]

Houghten

[11] Patent Number: 4,886,663
[45] Date of Patent: * Dec. 12, 1989

[54] **SYNTHETIC HEAT-STABLE ENTEROTOXIN POLYPEPTIDE OF *ESCHERICHIA COLI* AND MULTIMERS THEREOF**

[75] Inventor: Richard A. Houghten, Solana Beach, Calif.

[73] Assignee: Scripps Clinic and Research Foundation, La Jolla, Calif.

[*] Notice: The portion of the term of this patent subsequent to Jul. 29, 2003 has been disclaimed.

[21] Appl. No.: 559,469

[22] Filed: Dec. 12, 1983

Related U.S. Application Data

[63] Continuation-in-part of Ser. No. 455,265, Jan. 3, 1983, Pat. No. 4,545,931.

[51] Int. Cl.[4] ...................... A61K 39/108; C07K 7/10
[52] U.S. Cl. ..................................... 424/88; 530/327; 530/326; 530/324; 530/806
[58] Field of Search ................... 424/88; 260/112 SR; 530/326, 324, 327, 806

[56] References Cited

U.S. PATENT DOCUMENTS

| | | | |
|---|---|---|---|
| 4,314,993 | 2/1982 | Wijnendaele | 424/88 |
| 4,411,888 | 10/1983 | Klipstein et al. | 424/88 |
| 4,499,080 | 2/1985 | Duflot et al. | 514/12 |

FOREIGN PATENT DOCUMENTS 2145419 3/1985 United Kingdom.

OTHER PUBLICATIONS

Infect. Immun., 37, 550–557 (1982).
Proc. Nat'l Acad. Sci., 77, 4011–4015 (1980).
J. Biol. Chem., vol. 256, (1981) 7744–7746.
Stimulus–Secretion Coupling in the Gastrointestinal Tract, 10.
Infection and Immunity (1980) 91–97, vol. 29.
The J. Biol. Chem. 254, (1979) 9254–9261.
Proc. Nat'l. Acad. Sci. 76, (1979) 4832–4836.
The Journal of Infectious Diseases 141, (1980) 64–70.
Med. Hypotheses 5, 347–349, 1979.
Infection and Immun., 1983, 269–275, vol. 42.
Biochem. and Biophys. Res. Commun., 1983, vol. 112, pp. 320–326.
J. Gen. Microbiol. (1982) 128, 2081–2096.
J. Bacteriology, 1983, 728–733, vol. 155.
Gastroenterology 78, 1545–1553, 1980.
Wijnendaele et al., *Zbl. Vet. Med. B*, 29:441–450 (1980).
Duflot et al., *Proceedings, European Peptide Symposium*, Aug. 29, 1982.
M. P. Stevens, *Polymer Chemistry an Introduction*, Addison-Wesley Publishing Co., Inc., Reading, MA (1975), pp. 3, 8 and 9.

*Primary Examiner*—Delbert R. Phillips
*Attorney, Agent, or Firm*—Dressler, Goldsmith, Shore, Sutker & Milnamow, Ltd.

[57] ABSTRACT

A synthetic polypeptide having at least about 10% of the immunological activity of biologic heat-stable enterotoxin of *E. coli*. The synthetic polypeptide includes at least 14 amino acids in the sequence, from amino-terminus to carboxy-terminus, represented by the formula: CysCysGluLeuCysCysTyr-(Asn)ProAlaCysAla(Thr)-GlyCysAsn(Tyr) wherein the amino acid in parentheses may replace the immediately preceding amino acid residue, and at least one intramolecular disulfide bond formed between the Cys residues. The Cys residues that are not part of the intramolecular disulfide bond can be replaced by other amino acid residues or be bonded to substituent moieties. The polypeptides can be a monomeric or multimeric material containing an intramolecular, intrapolypeptide and/or an intramolecular, interpolypeptide cystine disulfide bond.

19 Claims, 15 Drawing Sheets

SYNTHETIC HEAT-STABLE ENTEROTOXIN POLYPEPTIDE OF ESCHERICHIA COLI AND MULTIMERS THEREOF

CROSS-REFERENCE TO RELATED APPLICATION

This is a continuation-in-part of copending application Ser. No. 455,265, filed Jan. 3, 1983, now U.S. Pat. No. 4,545,931.

TECHNICAL FIELD

The present invention relates to a synthetic polypeptide corresponding to heat-stable enterotoxin of *Escherichia coli*, and more particularly to synthetic polypeptides and multimers therof that comprise principal determinant domains responsible for the antigenicity of the *E. coli* heat-stable enterotoxin.

BACKGROUND ART

Acute diarrheal disease due to transient colonization of the small bowel by enterotoxigenic strains of *Escherichia coli* (*E. coli* or ETEC) is a major health problem of global scope for both humans and for animal husbandry. These organisms, together with rotavirus, are the principal cause of the often fatal acute diarrhea that is common among infants living in underdeveloped countries and among neonatal animals, particularly lambs and piglets. ETEC strains are also the usual cause of acute diarrhea among persons from temperate zones who travel to the tropics, and may be responsible for sporadic or epidemic episodes of diarrhea among children and adults living in either temperate or tropical areas.

The disease caused by ETEC is mediated by the release of two enterotoxins, either singly or together. The large molecular weight, antigenic heat-labile toxin (LT) has been purified to homogeneity and its subunit structure characterized as five B subunits which attach the holotoxin to the specific $GM_1$ ganglioside receptors on the mucosal surface, and a single A subunit which stimulates intracellular adenylate cyclase activity, thus evoking fluid and electrolyte secretion.

The low molecular weight, heat-stable toxin (ST) produced by ETEC strains of human or porcine origin has also recently been purified. Preparations of ST have a relatively high content of half-cystine, cause secretion by stimulating guanylate cyclase and are haptenic as evidenced by their capacity to raise an antitoxin response in animals immunized with the toxin coupled to a large molecular weight carrier.

The most practical approach for the prevention of ETEC-induced diarrhea would be an immunization program that provides protection against heterologous ETEC serotypes that produce either or both of the LT or ST enterotoxins. Immunization with either the biologic LT or the biologic ST toxin evokes an antitoxin response in experimental animals that protects against homologous and heterologous serotypes of strains that produce the specific toxin used for immunization. Immunization with the LT whole toxin or its B subunit yields protection against viable heterlogous strains that produce this toxin alone (LT+/LT−) or together with ST (LT+/ST+), but not against those which make just ST (LT−/ST+).

Immunization with biologic ST coupled to a large molecular weight carrier arouses serum antibodies that passively neutralize the secretory effect in the suckling mouse model of ST produced by heterlogous strains. Immunization also provides protection against direct challenge with viable heterlogous LT−/ST+, but not LT-producing strains. Neither of these toxins is suitable for immunization when given along, however, in view of their toxicity, their failure to provide protection against strains which produce the other toxin form, and the fact that the large molecular weight carriers that have been used to render the haptenic biologic ST molecule antigenic are unsuitable for human use.

Klipstein et al., *Infect. Immun.*, 37: 550–557 (1982) have reported the development of a vaccine made by conjugating the biologic ST toxin to the LT toxin by means of the carbodiimide reaction. As a result of that reaction, biologic ST acquires antigenicity when coupled to the large molecular weight LT carrier, while both cross-linked toxins retain most of ther antigenicity but loose most of their toxix properties. Rats immunized with the vaccine so produced were strongly protected against challenge with either LT or biologic ST and with viable ETEC strains which produce those toxins.

A semi-pure preparation of biologic ST was used for that vaccine because of the relatively low yield of pure biologic ST obtained by the available purification techniques which involve multiple chromatographic separation steps. The inclusion of the heterogeneous material in the vaccine may preclude its use for human immunization, however.

The present invention, relating to the synthetically produced ST, has overcome the problem of using ST derived from natural sources in that synthetic ST can be made in large quantities and in purified form, and has properties similar to those described for pure ST obtained by bacterial growth of a human ETEC strain. [Staples et al., *J. Biol. Chem.*, 255: 4716–4721 (1980); and Chan et al., *J. Biol. Chem.*, 256: 7744–7746 (1981)].

At least two types of ST have been identified by their physical properties. The first type known as ST I (also referred to as STa) is soluble in methanol and is active in the suckling mouse model. The second type, ST II (also referred to as STb) is methanol insoluble and not active in the suckling mouse model, but is active in ligated pig ileal loops.

Among the ST I polypeptides, at least three similar polypeptides, or determinant domains of those polypeptides, have been identified, and their amino acid sequences determined. These three types of ST I are referred herein as (i) ST Ia which was initially found in a bovine *E. Coli* strain and a portion of which is also encoded in porcine strains, (ii) that designated ST Ib from a human isolate of *E. coli* and (iii) ST Ic also isolated from human-infecting *E. coli*.

The nucleotide sequence coding for the ST Ia polypeptide has been determined. Translation of the nucleotide sequence into a polypeptide amino acid sequence leads to a polypeptide that contains 72 amino acids capped at the carboxy-terminus with a tyrosine group [So et al., *Proc. Natl. Acad. Sci. USA*, 77: 4011–4015 (1980)]. The ST Ic polypeptide is though to also contain 72 amino acids as well as several homologous domains with the ST Ia polypeptide. The ST Ib polypeptide is reported to contain only 18 amino acids ([Chan et al., *J. Biol. Chem.*, 256: 7744–7746 (1981)].

The 18 amino acids of the ST Ib polypeptide (18-mer) show great homology to amino acids 55 through 72 for the polypeptide of ST Ia. The homologous, almost identical, region is illustrated hereinbelow, beginning at amino acid number 55, from left to right and in the direction of amino-terminus to carboxy-terminus, of the ST Ia polypeptide:

ST Ia: AsnThrPheTyrCysCysGluLeuCysCys
ST Ib: AsnThrPheTyrCysCysGluLeuCysCys
AsnProAlaCysAlaGlyCysTyr
TyrProAlaCysAlaGlyCysAsn

More recent reports by Takeda et al., *Abstracts*, 19th Joint Conference US-Japan Cooperative Medical Science Program, Cholera Panel, 87–88 (1983) and Ikemura et al., *Chem. Letters*, (Chem. Soc. Japan), 101–104 (1983) have indicated the presence of further polypeptide sequences for this 18-mer polypeptide. Those workers referred to the ST molecule obtained from human and porcine strains of ETEC as $ST_h$ and $ST_p$, respectively. The amino acid residue sequences reported by those workers, from left to right and in the direction from amino-terminus to carboxy-terminus, are:

$ST_h$ AsnSerSerAsnTyrCysCysGluLeuCysCys
$ST_p$- - - AsnThrPheTyrCysCysGluLeuCysCys
AsnProAlaCysThrGlyCysTyr
AsnProAlaCysAlaGlyCysTyr

As can be seen from a comparison of both of the above sets of sequences; i.e., ST Ia, ST Ib, $ST_h$ and $ST_p$, a great deal of homology is shared among the carboxy-terminal fourteen residues of each of the four sequences shown.

Those workers also reported a synthesis of $ST_h$. Solution methods of synthesis were used to prepare the blocked polypeptide. Blocking groups were removed with hydrogen fluoride, and the Cys mercapto groups (thiols) were air oxidized. Air oxidation was carried out at a polypeptide concentration of $10^{-5}$ molar in distilled water adjusted to a pH value of 8.0 with aqueous ammonia. Oxidation was continued until free thiol groups disappeared.

Biologic activity of the synthetic $ST_h$ in a suckling mouse assay was reported to be the same as that for native toxin. Toxicity of the synthetic material was reported to be neutralized by antisera against the native toxin.

Examination of the above four 18-amino acid polypeptide sequences also reveals that six half-cystine (Cys) residues that are present. Oxidation of those half-cystine residues to cystine residues containing intramolecular disulfide bonds in the naturally occuring enterotoxin is thought to lend the observed heat stability to that material.

It is further noted, however, that while cystine disulfide bonds are known to be present in biologic ST, it is not known which pairs of half-cystine residues combine to form the three disulfide bonds that are present in the native ST molecule. Those three sulfide bonds can theoretically be formed from fifteen different combinations of the six Cys residues present.

Staples et al., supra, have shown that the disulfide linkages of biologic ST are required for biological activity of the toxin. Thus, chemical reduction to form half-cystines or performic acid oxidation to cysteic acid was shown to destroy the biological activity of the toxin. In addition, Chan et al., supra, have reported that the first four residues from the amio-terminus of the homologous 18-amino acids of the above sequence of St Ib are not required for biological activity. Thus, biological activity was obtained from the amino acid-containing polypeptide comprising the above carboxy-terminal 14 amino acids and their disulfide bonds.

Aimoto et al, *Biochem. Biophys. Res. Chem.*, 112: 320–326 (Apr. 15, 1983) have reported on the synthesis of the carboxy-terminal fourteen amino acid residues of the beforedescribed $ST_h$. That synthetic molecule was reported to have biologic activity 2–5 times that of the native $ST_h$ on a molar basis, using a suckling mouse assay.

In an oral presentation on Aug. 29, 1982 by Duflot et al., *Proceedings European Peptide Symposium*: 683–686, published in Berlin in June of 1983, those workers reported the synthesis of a porcine and human ST 18-mer polypeptides having their Cys mercapto groups blocked (S-blocked) with acetamidomethyl groups. Those amino acid residue sequences were purportedly identical to the sequences reported by So et al, supra, for ST Ia and by Chan et al., supra, for ST Ib. However, the seventh amino acid residue from the amino-terminus of the sequences reported by Duflot et al. was a glycine residue (Gly), while that residue in the beforedescribed sequences is a glutamic acid residue (Glu).

Duflot et al. reported that immunization of micr or rabbits with their S-blocked porcine ST toxin coupled to tetanus toxoid or ovalbumin produced antibodies that recognized the natural or the synthetic toxins equally. Substantially no biologic activity in the suckling mouse assay was reported for the S-blocked, porcine, synthetic polypeptide toxin. Those authors reported the lack of biologic activity to be due to the absence of intramolecular disulfide bonds in the S-blocked molecule, which is in keeping with the prior report of Staples et al., supra.

SUMMARY OF THE INVENTION

The present invention contemplates a synthetic polypeptide having an antigenicity, as a free monomer or as a multimer, that is at least about 10 percent of that of biologic *E. coli* heat-stable enterotoxin (ST). The synthetic polypeptide includes the amino acid residue sequence, taken left to right and in the direction from amino-terminus to carboxy-terminus, represented by the formula:

$$R_m{}^{13}-\overset{\overset{\displaystyle R_a{}^1}{|}}{C}ys(R_g{}^7)\overset{\overset{\displaystyle R_b{}^2}{|}}{C}ys(R_h{}^8)GluLeuCys(R_i{}^9)\overset{\overset{\displaystyle R_d{}^4}{|}}{C}ys(R_j{}^{10})Tyr(Asn)$$
$$\underset{\underset{\displaystyle R_c{}^3}{|}}{}$$

$$ProAlaCys(R_k{}^{11})\overset{\overset{\displaystyle R_e{}^5}{|}}{}Ala(Thr)GlyCys\,(R_l{}^{12})\overset{\overset{\displaystyle R_f{}^6}{|}}{}Asn(Tyr)$$

wherein the three specific amino acid residues in parentheses are each an alternative to the immediately preceding amino acid residue in the sequence;

a–f and g–l are integers each having a value of zero or one, with the proviso that if the value of any of a–f or g–l is zero, the corresponding $R_{a-f}{}^{1-6}$- or $R_{g-l}{}^{7-12}$-group is absent, and when an $R_{a-f}{}^{1-6}$-group is absent the sulfur atom of the Cys residue having an absent $R_{a-f}{}^{1-6}$-group forms a cystine disulfide bond, while if the value of the a–f or g–l is one, the corresponding $R_{a-f}{}^{1-6}$- or $R_{g-l}{}^{7-12}$-group is present;

the $R_{a-f}{}^{1-6}$-groups, when taken individually, are the same or different moieties bonded to the sulfur atom of the Cys residues and are selected from the group consisting of hydrogen, an alkyl group containing 1 to about 4 carbon atoms, a substituted alkyl group containing 2 to about 20 carbon atoms, an acyl group containing 1 to about 8 carbon atoms, and a substituted acyl group containing 2 to about 10 carbon atoms;

the $R_{g\text{-}l}^{7\text{-}12}$-groups are the same or different alternative amino acid residues to each immediately preceding Cys residue;

at least two of a-f and two of g-l are zero and two Cys residues are present with the proviso that the synthetic polypeptide contains at least one intramolecular cystine disulfide bond formed from the at least two Cys residues present; and "m" is an integer having the value of zero or one with the proviso that if "m" is zero $R_m^{13}$ is absent, and if "m" is one $R_m^{13}$ is selected from the group consisting of a chain containing 1 to about 54 amino acid residues, a linking group, and the acyl portion of a carboxylic acid containing 1 to about 20 carbon atoms forming an amide bond with the amine of the amino-terminal residue.

When in monomeric form, the above at least one disulfide bond is an intramolecular cystine disulfide formed between the at least two Cys residues present in the antigenic polypeptide. When the antigenic polypeptide is in a multimeric form that contains a plurality of polypeptide repeating units, the above at least one disulfide bond may be an intramolecular cystine disulfide formed between the at least two Cys residues present in each polypeptide repeating unit, or that disulfide bond may be an intramolecular cystine disulfide formed between one of the at least two Cys residues present in a first repeating unit and another one of the at least two Cys residues present in a second repeating unit. Thus, whether in monomeric or multimeric forms, the cystine disulfide bond is intramolecular. However, in the monomeric ST, the disulfide bond is an intrapolypeptide bond, while in multimeric ST embodiments the disulfide bond may be an intrapolypeptide or interpolypeptide bond.

The above antigenic polypeptide may be used in its monomeric form alone as when used in a diagnostic where competitive binding determinations are carried out, or more preferably as a monomeric immunogen of a vaccine when conjugated to a carrier molecule such as the porcine immunoglobulin G. In still more preferred practice, the antigenic polypeptide is utilized in a multimeric form.

When utilized in multimeric form, the polypeptide is one of a plurality of repeating units of a multimer. In one embodiment, the multimer contains at least two of the antigenic ST polypeptides bonded together head-to-tail through an amide bond formed between the amine group of the amino-terminus of one polypeptide and the carboxyl group of the carboxy-terminus of the second polypeptide. In another multimeric embodiment, the antigenic polypeptide is one of a plurality of repeating units of a polymer whose polypeptide repeating units are bonded together by interpolypeptide cystine disulfide bonds formed between the Cys residues of the polypeptide repeating units.

In more preferred practice for the monomeric and multimeric forms of synthetic ST, with reference to the above formula for the antigenic synthetic polypeptide:

a-f are integers having a value of zero or one with the proviso that:
"e" is zero when "a" is zero,
"d" is zero when "b" is zero, and
"f" is zero when "c" is zero;
the further proviso that at least one of "a", "b" or "c" must be zero so that the corresponding $R_{a\text{-}c}^{1\text{-}3}$ is absent as is the $R_{d\text{-}f}^{4\text{-}6}$ whose subscript is zero when said "a", "b" or "c" is zero and an intramolecular cystine disulfide bond is present between the respective Cys residues for which a subscript value of zero requires another subscript value to be zero; and when a value of a-f is one; said $R_{a\text{-}f}^{1\text{-}6}$-groups, when taken individually, are the same or different moieties bonded to the sulfur atom of the Cys residue and are selected from the group consisting hydrogen, an alkyl group containing 1 to about 4 carbon atoms and a substituted alkyl group containing 2 to about 20 carbon atoms;

wherein g-l are integers having the value of zero or one, as noted above, with the proviso that:
each of "g" and "k" is zero when "a" is zero,
each of "h" and "j" is zero when "b" is zero, and
each of "i" and "l" is zero when "c" is zero; and
when the value of g-l is one, the $R_{g\text{-}l}^{7\text{-}12}$-groups are the same or different alternative amino acid residues to each immediately preceding Cys residue.

The monomeric or multimeric antigenic synthetic polypeptide can thus be seen to contain at least one intramolecular disulfide that is an intrapolypeptide or interpolypeptide disulfide bond of a cystine residue formed between two Cys residues. In the more preferred embodiments, the intrapolypeptide cystine disulfide bond is formed between the pairs of Cys residues of groups $R_a^1$ and $R_e^5$, or $R_b^2$ and $R_d^4$, or $R_c^3$ and $R_f^6$. In still more preferred embodiments, the monomeric synthetic polypeptide contains at least two cystine residues and their disulfide bonds are formed betweenn the above pairs of Cys residues, and in most preferred embodiments, the synthetic polypeptide contains three cystine residues between the aforementioned Cys residues.

Biologic, natural (native) ST contains three disulfide bonds formed among the six Cys residues. The most preferred monomeric synthetic ST of this invention has an identical 18-amino acid residue sequence to a biologic, native ST, and also contains three intramolecular, intrapolypeptide disulfide bonds formed among its six Cys residues. However, the thin layer chromatographic and electrophoretic mobilities compared with literature values, and immunologic properties of biologic and synthetic, monomeric ST molecules are different even though the two molecules have the same primary structure and each contains three intramolecular, intrapolypeptide disulfide bonds.

The monomeric or multimeric synthetic ST of this invention having at least 10% of the antigenicity of biologic ST may be prepared by synthesizing under non-oxidizing conditions a first, unoxidized polypeptide such as the polypeptide described before wherein hydrogen is the $R_{a\text{-}f}^{1\text{-}6}$-group of the at least two of a-f that are one. More preferably, for the monomeric synthetic ST and the multimeric forms of synthetic ST, the first unoxidized polypeptide includes the amino acid residue sequence taken from left to right and in the direction from amino-terminus to carboxy-terminus represented by the formula:

$$\text{Cys}(R_g^7)\text{Cys}(R_h^8)\text{GluLeuCys}(R_i^9)\text{Cys}(R_j^{10})\text{Tyr}(\text{Asn})\text{ProAlaCys}(R_k^{11})\text{Ala}(\text{Thr})\text{GlyCys}R_l^{12}\text{Asn}(\text{Tyr})$$

wherein the above more preferred amino acid residue sequence without the three specific parenthesized amino acid residues and the $R_{g\text{-}l}^{7\text{-}12}$-groups corresponds to the amino acid residues of the ST Ib polypeptide numbered 5 through 18 from the amino-terminus of that ST Ib polypeptide;

the three specific amino acid residues in parentheses are each an alternative to the immediately preceeding amino acid residue;

$R_g^7$, $R_h^8$, $R_i^9$, $R_j^{10}$, $R_k^{11}$ and $R_l^{12}$ are the same or different alternative amino acid residues to the preceding Cys residue; g-l are integers each having the value of zero or one with the proviso that if any of g-l has a value of zero the corresponding, individual $R_{g\text{-}l}^{7\text{-}12}$-group is absent, and the value of at least two of g-l are zero, with the further proviso that at least one pair of non-contiguous Cys residues from the Cys residues preceding the individual $R_{g\text{-}l}^{7\text{-}12}$-groups is present, the non-contiguous pairs of Cys residues being selected from the group consisting of the Cys residues corresponding to amino acid residue positions in the ST Ib polypeptide numbered 5 or 6 and 9 or 10, 5 or 6 and 14, and 9 or 10 and 17 from the amino-terminus of the ST Ib polypeptide.

Once the first polypeptide is synthesized it is provided, and is dissolved or suspended in an aqueous composition at a concentration of less than about 5 milligrams per milliliter, and more preferably at less than about 2 milligrams per milliliter, and most preferably at a concentration of about 1 milligram per milliliter to about 0.1 milligrams per milliliter. Preferably, the aqueous composition is alkaline and has a pH value less than about 10.5.

The obtained first polypeptide-containing composition is thereafter contacted with molecular oxygen as an oxidizing agent. The contact between the composition and molecular oxygen is maintained for a period of about 1 to about 24 hours to form at least one intrapolypeptide or one interpolypeptide cystine disulfide bond between the at least two Cys residues present.

In preferred practice for the monomeric molecule, the disulfide bond is formed between the pairs of Cys residues corresponding to the amino acid residues positions in the ST Ib polypeptide numbered 5 and 14, 6 and 10, and 9 and 17 from the amino-terminus of the ST Ib polypeptide. In more preferred practice for that molecule, the contact between molecular oxygen and the solution containing the first polypeptide is maintained for a period sufficient to form two disulfide bonds between the above mentioned pairs of Cys residues, and still more preferably to form three, intramolecular cystine disulfide bonds between those pairs of Cys residues.

The present invention has several benefits and advantages. One such benefit is that it provides a source of immunologically active ST which may be prepared in large quantities and in substantially pure form. One of the advantages of the present invention is that the synthetic ST may be used to vaccinate humans and other animals against strains of *E. coli* that produce ST. Another benefit of the present invention is that the synthetic ST may be utilized in a diagnostic reagent or reagent system for assaying the presence of an infection caused by ST-producing *E. coli*. Yet another benefit of this invention is that ST molecules having several times the antigenicity of the native toxin can be prepared. Still another advantage of the invention is that synthetic ST polypeptides can be prepared that have substantially less biologic activity than the native toxin. Still further benefits and advantages of the present invention will be apparent to those skilled in the art from the detailed description examples and claims which follow.

BRIEF DESCRIPTION OF THE DRAWINGS

In the drawings forming the portion of this disclosure.

Figure 10:
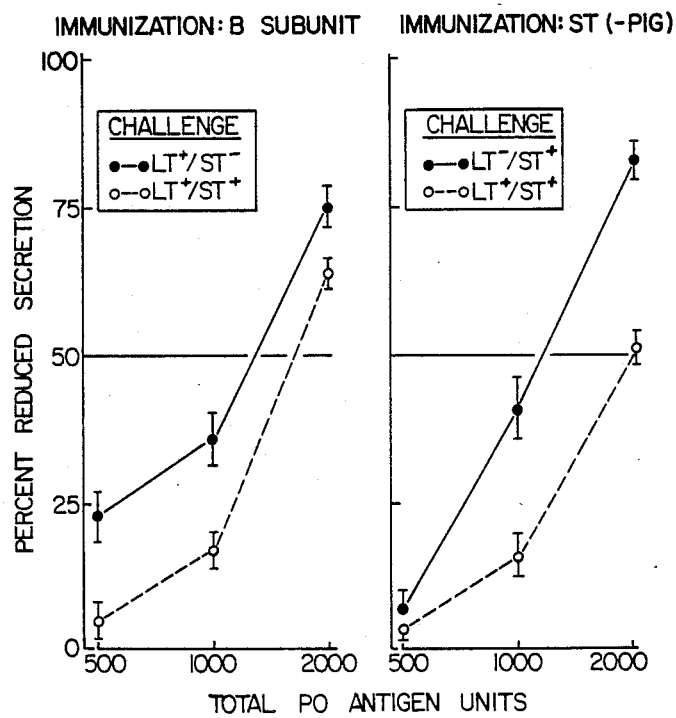

FIG. 10 illustrates protection attained against challenge with the human LT+/ST+ *E. coli* strain (○- - -○) compared to that against human LT- or ST-only *E. coli* strains (●——●) in rats immunized with graded p.o. antigen unit dosages of either the B subunit or synthetic ST coupled to PIG. All rats received i.p. primary immunization with 200 antigen units.

Figure 11:
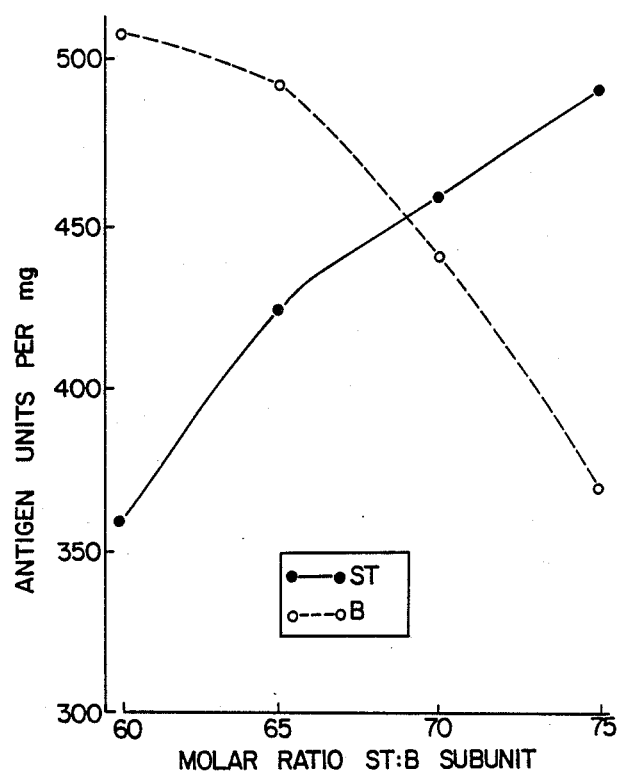

FIG. 11 illustrates the effect of varying the initial molar ratio of ST (●——●) to the B subunit (○- - -○) on the antigenicity of the component toxins in the cross-linked vaccine. The ratio of carbodiimide to conjugate protein was consistently 1.5:1 by weight.

Figure 12:
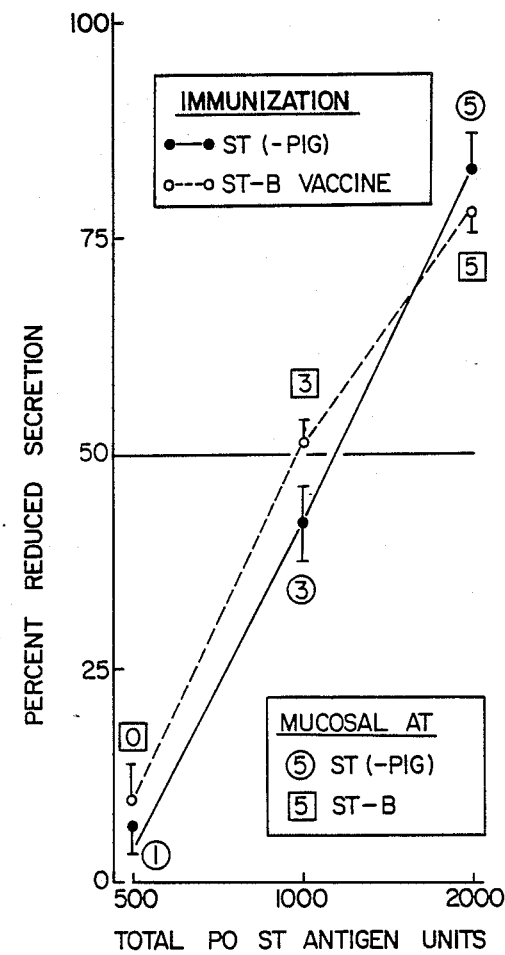

FIG. 12 illustrates the immunogenicity of ST when given coupled to PIG or as a component of the cross-linked vaccine. All rats received (i.p.) primary immunization with 200 ST antigen units, followed by graded peroral (po) boosts of ST as shown on the abscissa, and were then challenged with the human LT−/ST+ *E. coli* strain. Mucosal AT values are shown by numbers within circles or squares and are as in FIG. 9.

Figure 13:
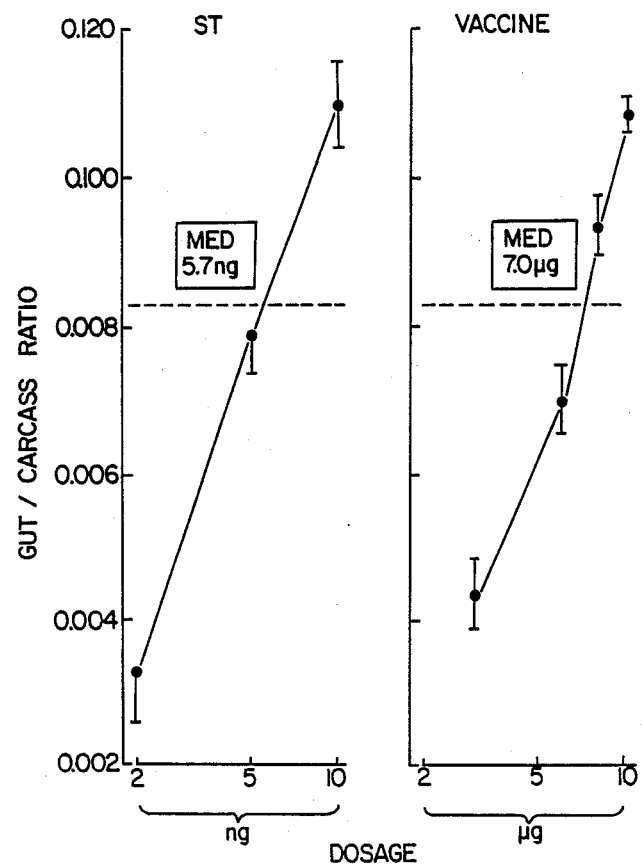

FIG. 13 illustrates the toxicity of uncoupled, synthetic ST (left panel) and of that ST coupled to PIG as a vaccine (right panel) in the suckling mouse assay. Values are the mean ± standard error of the mean for 3 mice for each datum point. MED, minimum effective dosage, is that dosage (here, in nanograms or micrograms) that yields a positive response of a gut:carcass weight ratio of at least 0.083. Abscissas show the dosages administered in nanograms (left panel) or micrograms (right panel).

Figure 14:
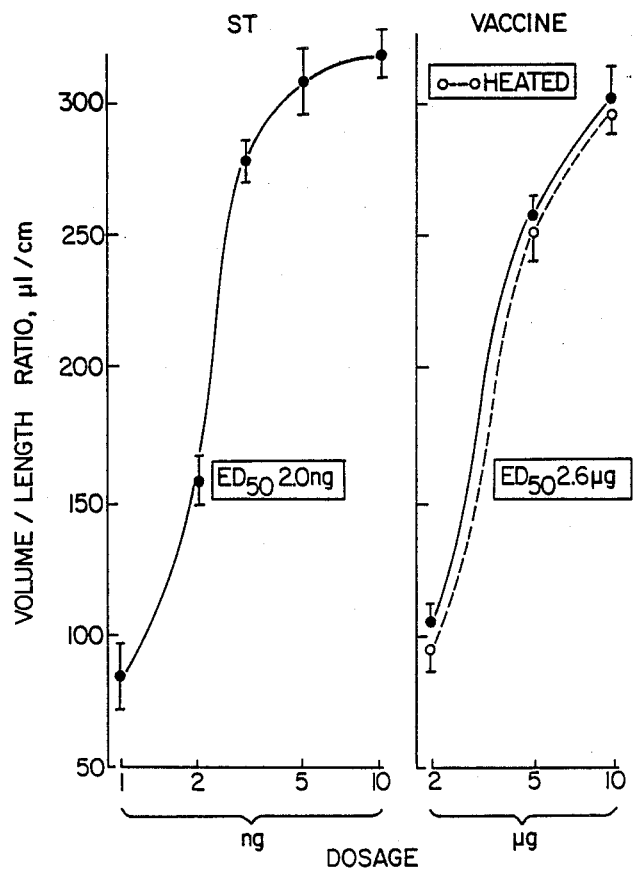

FIG. 14 illustrates the toxicity of uncoupled synthetic ST (left panel) and of that ST coupled to PIG as a vaccine (right panel) in rat ligated ileal loops. Values are the mean ± standard error of the mean for 3 rats for each datum point. $ED_{50}$ is that dosage in nanograms or micrograms which yields one-half of the maximum secretory response. "Heated" indicates the vaccine was exposed to 65° C. for 1 hour prior to testing. Abscissas show the dosages administered in nanograms (left panel) or micrograms (right panel).

Figure 15:
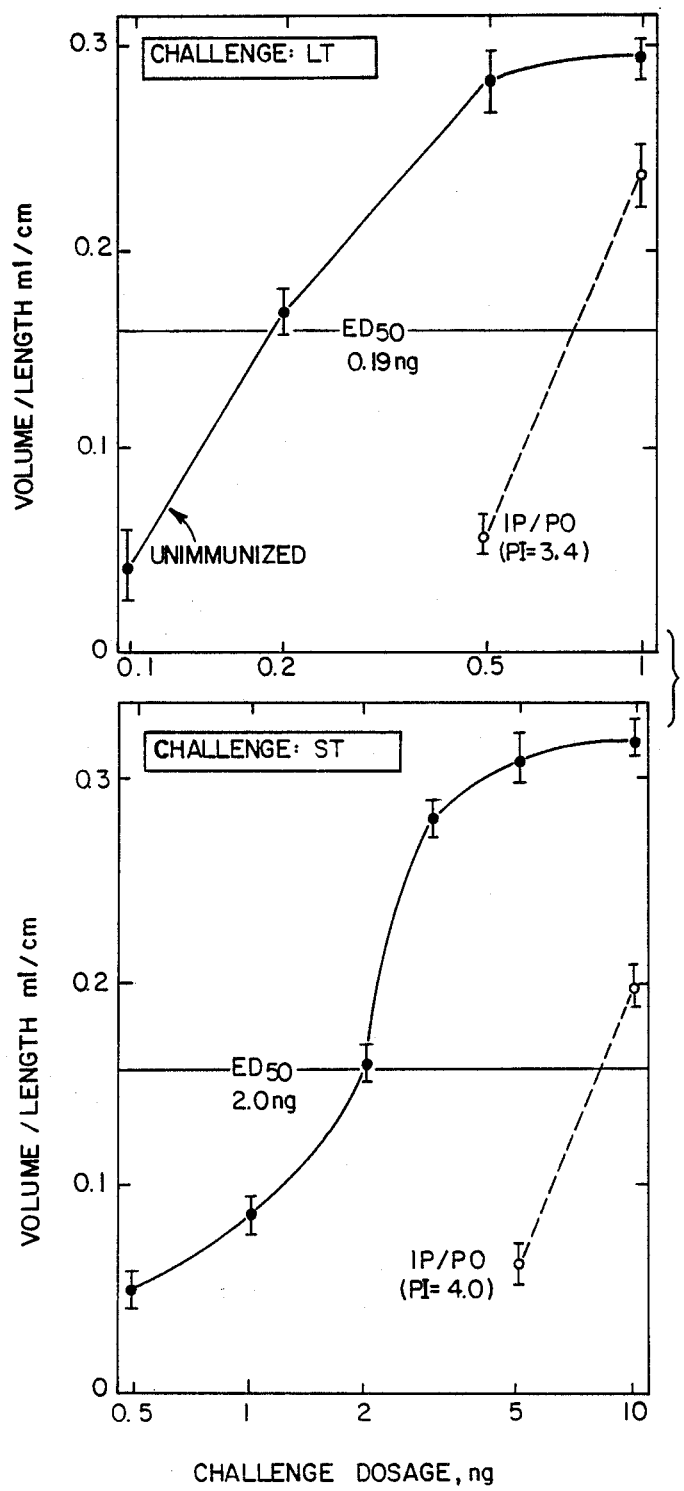

FIG. 15 illustrates protection attained in immunized rats. The horizontal line designates 50% of maximum secretion in unimmunized animals, and $ED_{50}$ signifies that dosage in nanograms which produced this value in this group of rats. PI signifies protection index, and IP/PO (intraperitoneal/peroral) signifies the immunization route. The upper panel shows results from challenge with LT, while the lower panel shows results from challenge with monomeric ST. The abscissa for both panels shows the dosage of challenging toxin in nanograms. The ordinate shows the volume of secretion in milliliters/centimeter of illeal loop.

Figure 16:
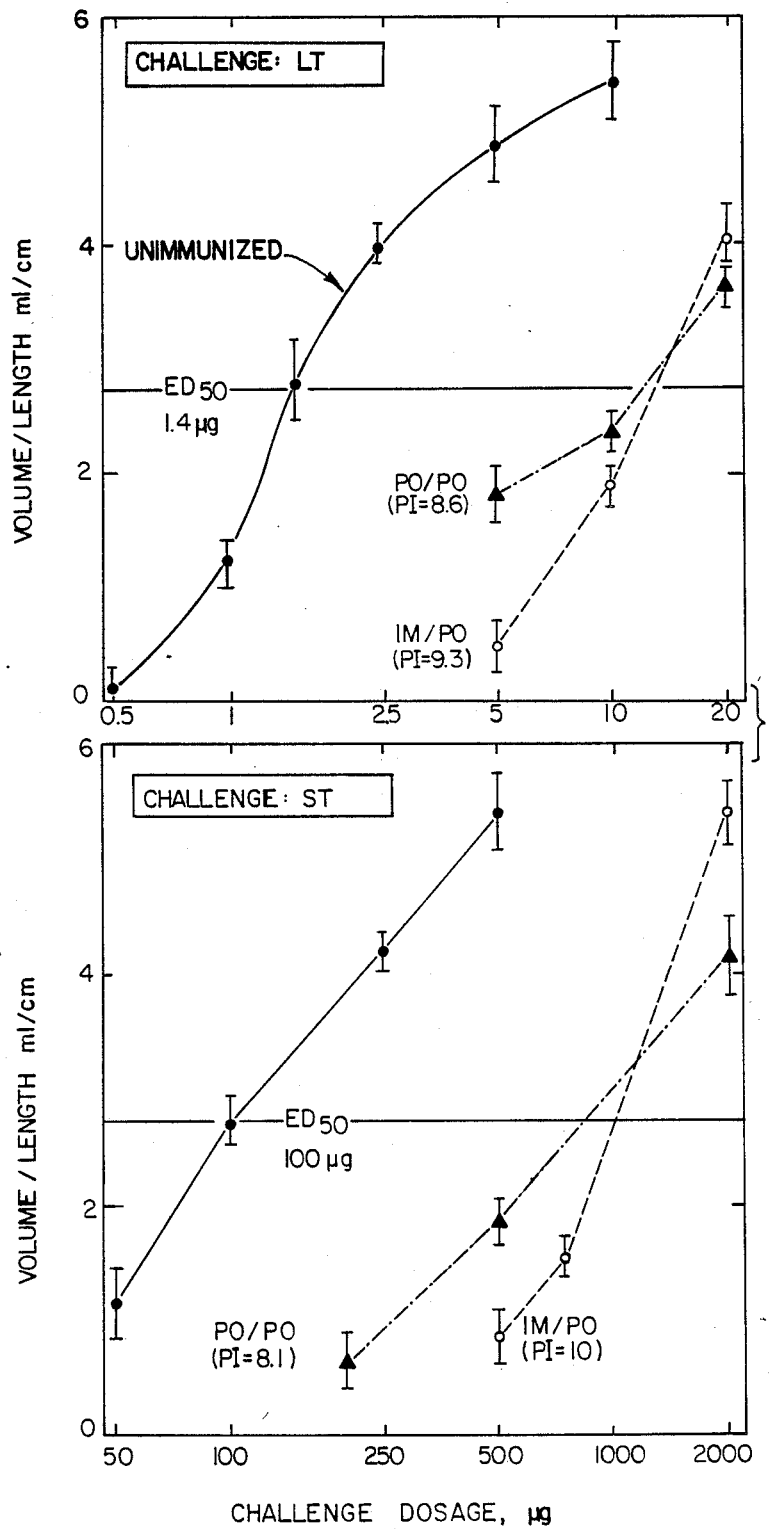

FIG. 16 illustrates protection attained in immunized rabbits. Designations are the same as in FIG. 15, except that the challenging dosages and $ED_{50}$ values are in micrograms, and IM/PO signifies immunization by an intramuscular/peroral route.

Figure 17:
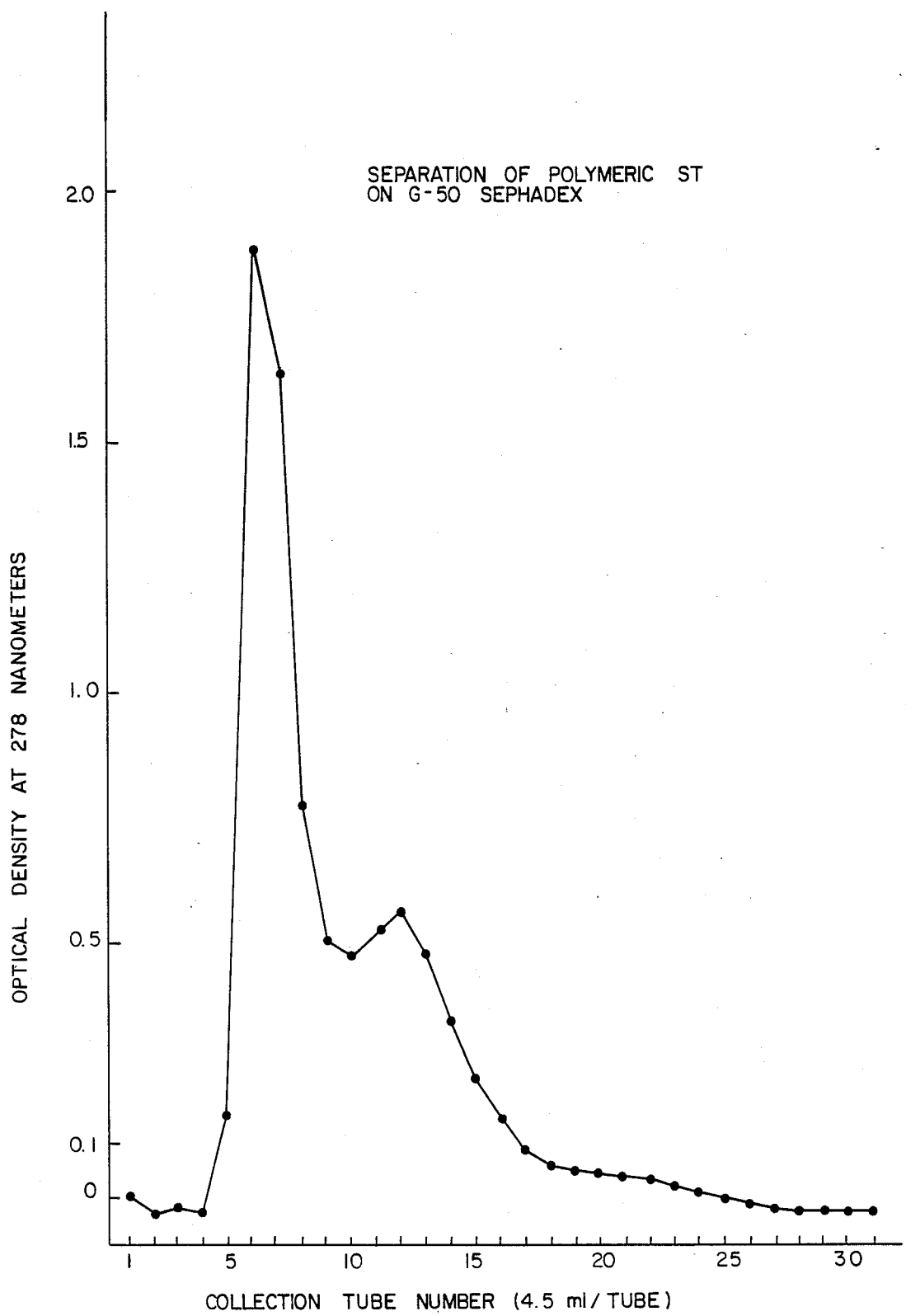

FIG. 17 is a graph that illustrates the separation of a polymeric ST (P-ST) preparation using Sephadex G-50 column chromatography. The numerals of the abscissa refer to column eluate collection tube numbers, each tube receiving 4.5 milliliters of eluate, while the numerals of the ordinate refer to the optical density of the collection tube contents measured at 278 nanometers. The contents of collection tubes numbered 5-9 were pooled to provide a solution containing substantially P-ST, while the contents of collection tubes numbered 10-18 were pooled to provide a solution that primarily contained synthetic monomeric ST (M-ST).

Figure 18:
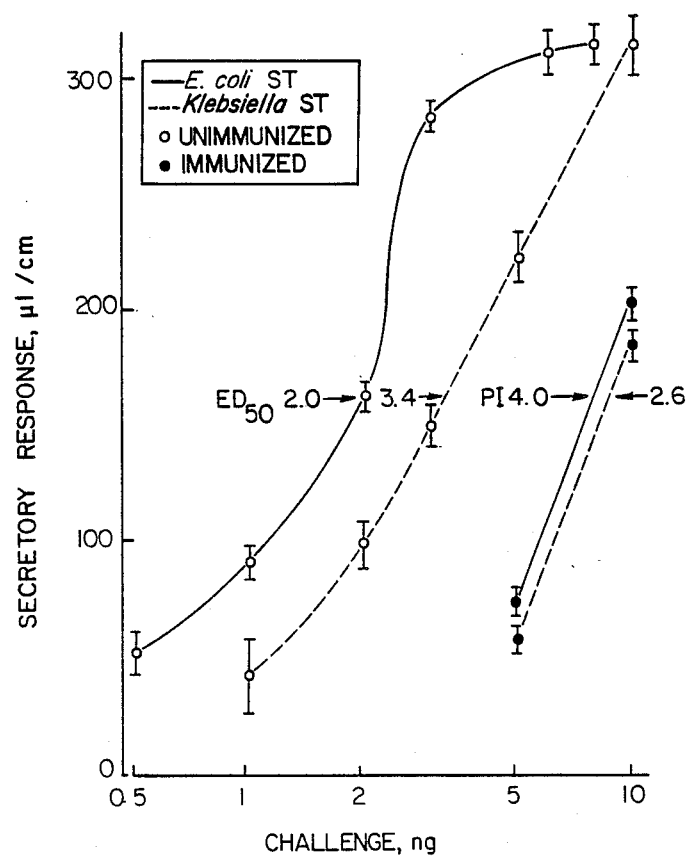

FIG. 18 illustrates graphical representations of dose-secretory response values for immunized (●) and unimmunized (○) rats that were challenged by instillation of graded dosages into ligated ileal loops for 18 hours with *E. coli* ST (——) or with *Klebsiella pneumoniae* ST ( - - - ). The rats were immunized with a vaccine containing synthetic monomeric ST conjugated to a natural LT B subunit as the immunogen. The abscissa shows nanograms of the challenging toxin, while the ordinate shows the secretory responses of those illeal loops in microliters per centimeter of loop. $ED_{50}$ signifies the dosage that produces 50 percent maximum secretion in unimmunized rats. PI is the protection index obtained by dividing the dosage of toxin in immunized animals that yielded the same secretion as the 50% effective dose ($ED_{50}$) in unimmunized animals by the value for unimmunized animals.

Figure 19:
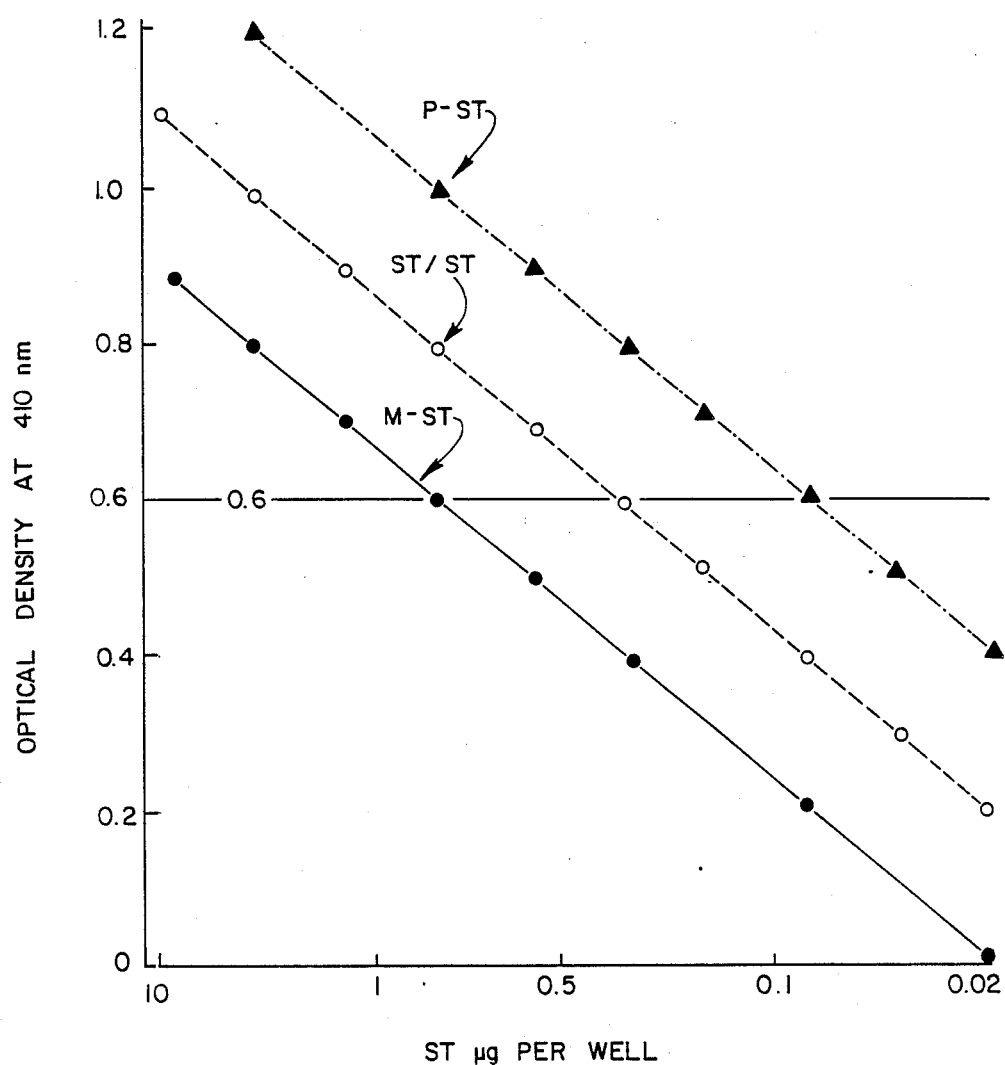

FIG. 19 is a graph that illustrates relative antigenicities of synthetic monomeric ST (M-St; ●- - -●), a synthetic multimeric head-to-tail ST dimer (ST/ST; ○- - -○) and of a preparation of polymeric synthetic ST (P-ST; △—.—△) as determined by a double-sandwich ELISA technique with hyperimmune antisera raised to an M-ST conjugate. Percent antigenicity is based upon the micrograms of ST required to yield an optical density at 410 nanometers of 0.600. The abscissa shows the amount of ST per microtiter plate well in micrograms.

Figure 20:
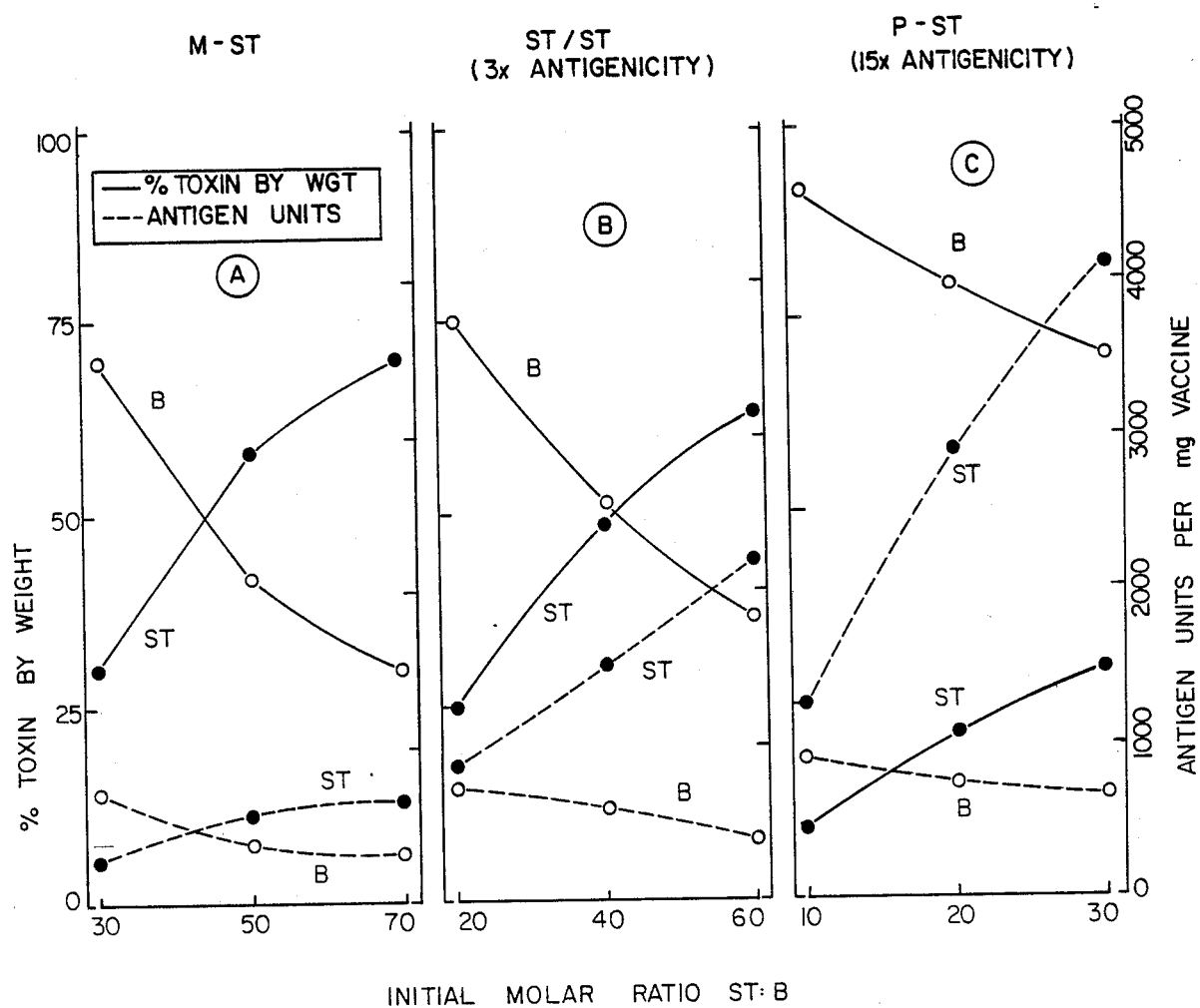

FIG. 20 provides graphical illustrations of properties of three preparations of ST conjugated to the LT B subunit using glutaraldehyde as coupling agent at a molar ratio of glutaraldehyde to the B subunit of 700:1. Panel A illustrates conjugates prepared using synthetic monomeric ST (M-ST), panel B illustrates conjugates prepared using synthetic multimeric head-to-tail ST dimer (ST/ST), and panel C illustrates conjugates prepared using polymeric synthetic ST (P-ST). The numerals of the abscissas of each of the panels represent the molar ratios of the appropriate ST preparation to B subunit in the initial conjugation reaction mixture. The left-hand ordinate for each of the panels represents the percent of toxin by weight in the reaction mixtures, and data points connected by solid lines (——) show molar ratios of the two toxins in the reaction mixture. The right-hand ordinate for each panel shows the determined number of antigen units per milligram of vaccine prepared, and data points connected by dashed lines ( - - - ) show the antigenicity for each conjugate. Plots relating to the ST toxin are indicated by solid circles (●), while plots relating to the B subunit toxin are indicated by open circles (○). The letters "B" and "ST", designating data relating to the B subunit and to synthetic ST, respectively, are also placed adjacent each line for added clarity. Antigen units for the conjugates were determined by the double sandwich ELISA technique with antisera to M-ST; ST values for all conjugates are expressed in terms of M-ST antigen units.

Figure 21:
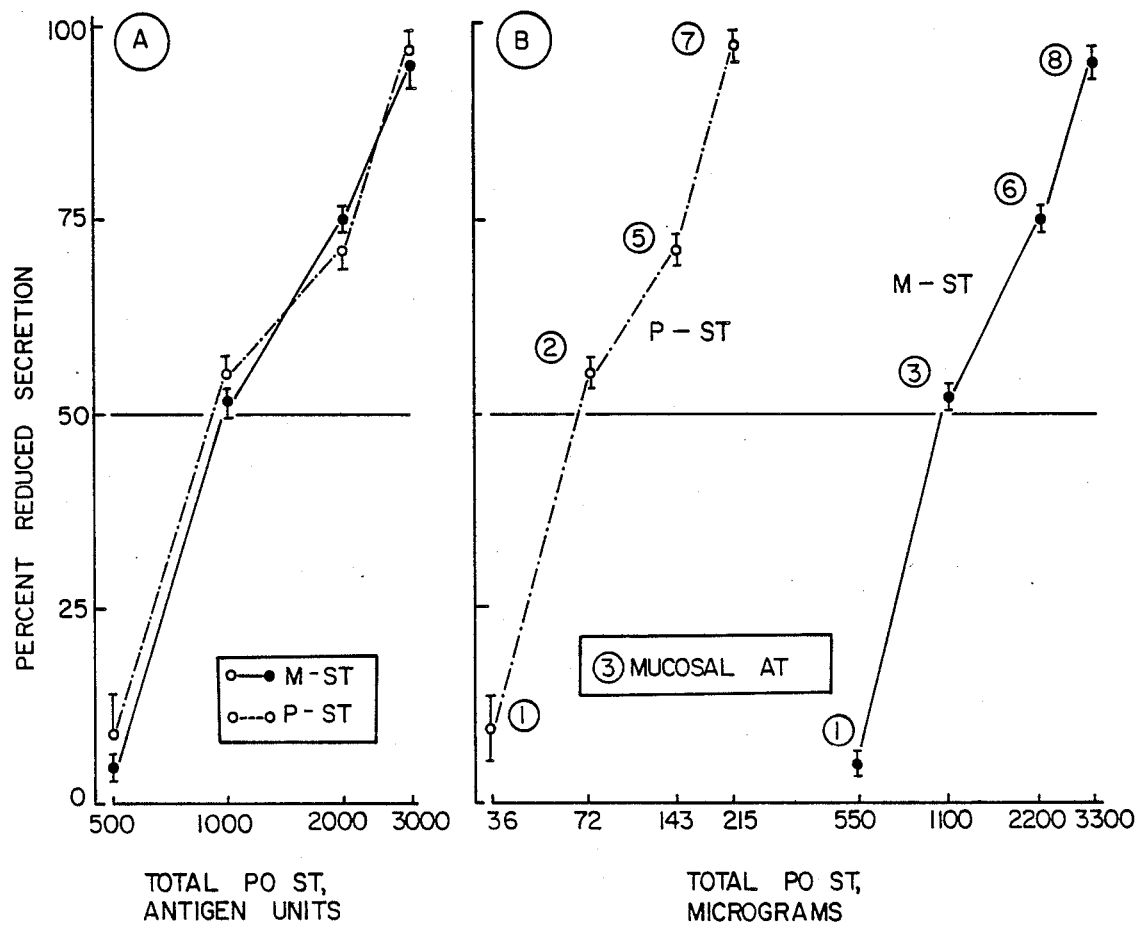

FIG. 21 illustrates the immunogenicity of vaccines containing conjugates of synthetic monomeric ST (M-ST) or of polymeric synthetic ST (P-ST) with the LT B subunit is providing reduced secretion (ordinate for both panels) and in increased mucosal IgA antitoxin titers after immunization. All rats received primary interperitoneal immunizations containing 200 antigen units of either conjugate followed by peroral (p.o.) boosts of differing amounts of the same vaccine. The rats were challenged with a viable human LT−/ST+ strain by instillation of that strain. The values for mucosal IgA antitoxin (AT) are circled and are shown as the mean increase in titers in immunized rats over those in unimmunized controls; AT in rats immunized with the vaccine containing the P-ST conjugate was measured and is expressed as M-ST titers. The data of panel A are expressed as total peroral (p.o.) dosages in M-ST antigen units, while the data in panel B are expressed as total peroral (p.o.) dosages in micrograms of ST, as M-ST, contained in the administered, boosts.

Figure 22:
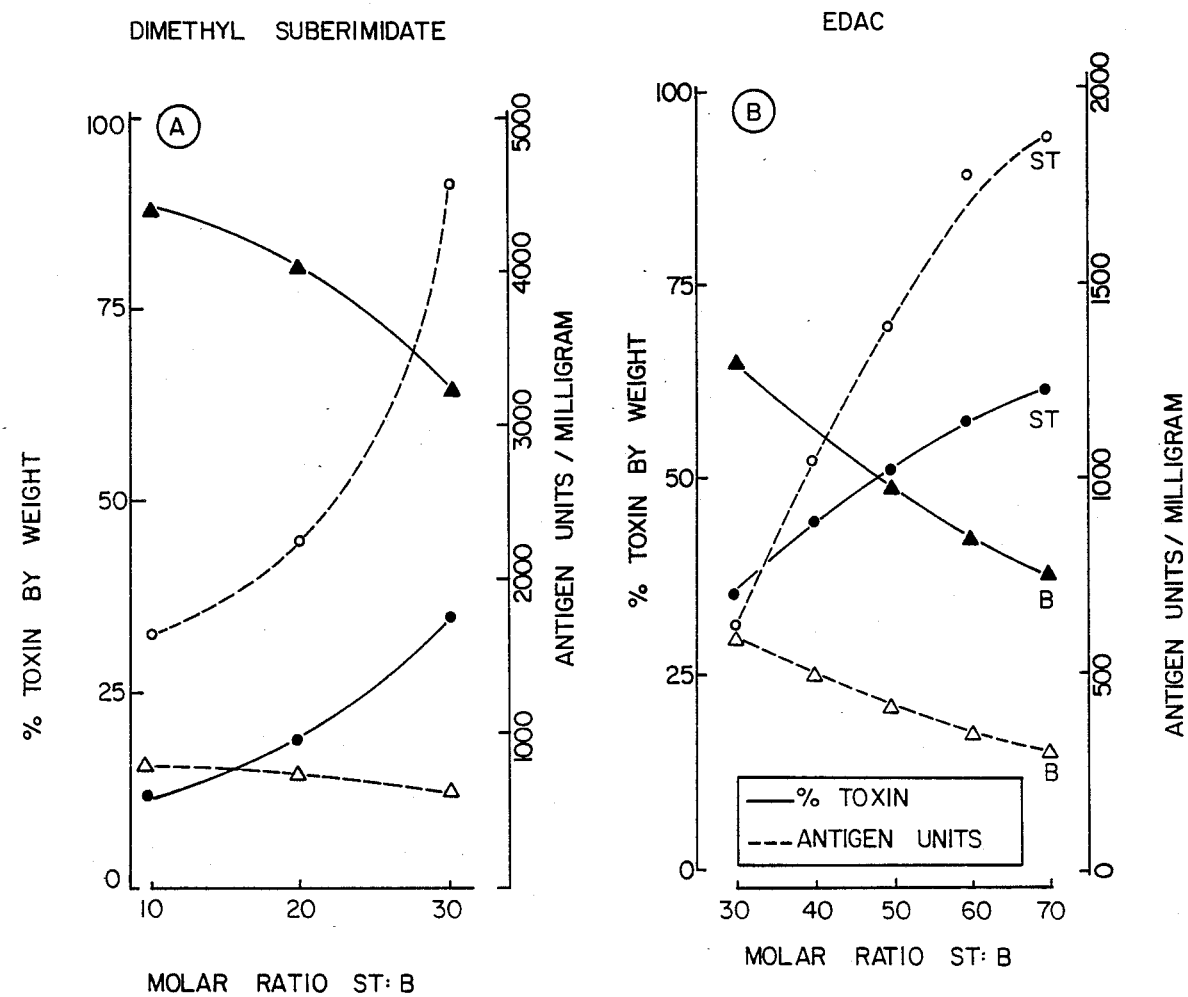

FIG. 22 contains two panels of graphs that illustrate the percentage of toxin by weight and the number of antigen units per milligram of conjugates prepared from polymeric ST (P-ST) and the LT B subunit as a function of the molar ratio of P-ST to B subunit of the conjugates. Properties of conjugates prepared using dimethyl suberimidate (DMS) are shown in panel A, while properties of conjugates prepared using EDAC [1-ethyl-3-(3-dimethylaminopropyl) carbodiimide] are shown in panel B. Data relating to the LT B subnit in both panels are shown as triangles, while data relating to P-ST are shown as circles. Filled in triangles and circles (▲, ●), and solid lines refer to toxin percentage data, while open triangles and circles (△, ○) and dashed lines refer to antigen unit data. The ratios by weight of coupling agent to B subunit were 1:1 for DMS and 1.5:1 for EDAC.

DETAILED DESCRIPTION OF THE INVENTION

I. Synthetic ST

The present invention contemplates synthetically produced polypeptides having the amino acid residue sequence of at least the carboxy-terminal fourteen amino acid residues of the heat-stable enterotoxin (ST) produced by *Eschericia coli* (*E. coli*). The synthetic polypeptides of this invention in monomeric and multimeric forms are useful as immunogens or portions thereof of vaccines that can be used in protecting against diarrheal infections produced by *E. coli* producing such toxins as well as against infections produced by other bacteria such as *Klebsiella pneumoniae* that produce similar toxins. The monomeric and multimeric synthetic ST polypeptides and antibodies raised to them are also useful in diagnostics for assaying for the presence of ST-producing organisms, such as *E. coli*.

When used as a vaccine for immunizations, the synthetic ST polypeptides may be used alone, as is the case for the polymeric ST (P-ST) multimer, or used linked to a carrier as a conjugate as in the case for the monomeric ST (M-ST) and ST multimers. The synthetic ST immunogen is present in an effective amount in such a vaccine, and is dispersed or dissolved in a physiologically tolerable diluent.

Particularly useful conjugate carriers include the heat-labile enterotoxin of *E. coli* (LT) as well as the smaller, B subunit of that toxin (LT B). Additionally useful carrier include porcine immunoglobulin G (PIG), keyhole limpet hemocyanin (KLH), tetanus toxoid, poly-L-(Lys:Glu), peanut agglutinin, olvalbumin, soybean agglutinin, bovine serum albumin (BSA), human serum albumin, and the like.

Physiologically tolerable (acceptable) diluents include water, saline, phosphate buffered saline (PBS), and the like, and typically further include an adjuvant. Complete Freund's adjuvant (CFA), incomplete Freund's adjuvant (IFA) and alum are typically used adjuvants that are well known in the art, and are available commercially from several sources.

The ST immunogen contained in a vaccine is present in an "effective amount", which amount depends upon a number of factors as is well known in the immunological arts. Included among those factors are the body weight and species of animal to be immunized, the carrier when used and the agent utilized to couple the ST to the carrier, the adjuvant when used, the duration of protection desired, and the immunization protocol being utilized.

For example, in some challenge studies rats received about 1500 to about 2500 antigen units (defined in Section III B, hereinafter) when immunized with an ST conjugate in a protocol wherein one intraparenteral injection was followed by two peroral boosts. In another challenge study, rabbits received about 2500 to about 3000 antigen units of an ST-containing conjugate and were protected.

The weight of synthetic ST in such vaccines depends upon the antigenicities of the ST preparation utilized and of the ST-containing conjugate. Thus, using the knowledge that rats were protected from challenge when immunized with a total of about 1500 to about 2500 antigen units of ST-containing vaccine, about 1500 to about 2500 micrograms of an M-ST—LT B conjugate per rat was administered, while about 100 to about 300 micrograms of P-ST—LT B conjugate per rat were administered to achieve a similar result. A total of about 600 micrograms of uncoupled (non-conjugated) P-ST were utilized in rabbits to provide an antiserum titer sufficient to indicate protection from challenge.

It is thus seen that the amount of ST needed to provide an "effective amount" can vary widely. However, one skilled in the art can obtain that effective amount using routine laboratory procedures from the discussion and citations that follow.

Synthetic ST embodying the present invention exhibits antigenicity, as a monomer alone or bound to a protein carrier as a conjugate or as a multimer alone or bound to a carrier as a conjugate, that is at least about 10 percent of that exhibited by biologic, native ST obtained from *E. coli* which infect humans and other animals. It is known that the monomeric naturally occurring, biologic ST contains six Cys residues which form three intramolecular, intrapolypeptide disulfide bonds of cystine residues. The presence of cystine disulfide bonds has been shown by others, Chan et al., supra., to be necessary for the functioning of naturally occurring ST.

Two of the six Cys residues of ST may theoretically combine in fifteen different ways to form a disulfide bond of one cystine residue. Six possible combinations of paired Cys residues remain for the formation of a second disulfide bond, and thereafter only one combination is left for the third disulfide bond. Thus, there are a total of ninety (15×6×1) theoretically possible secondary structural isomers of each primary amino acid residue sequence of ST that contain six Cys residues and two or three disulfide bonds.

However, because of the practical difficulty of forming a cystine disulfide bond between pairs of contiguous Cys residues of which there are two pairs in the ST molecule, and redundant possible structures, there are considerably fewer than ninety secondary structural isomers containing two or three disulfide bonds. The specific pairs of Cys residues which form the disulfide bonds present in naturally occurring biologic ST are not known.

It has now been found that an immunologically active synthetic ST can be prepared having a primary amino acid residue sequence that is substantially the same as that of naturally occurring biologic ST, but whose secondary structure, as determined by disulfide bond formation, is different from that of naturally occurring ST. Antigenic activity is found with monomeric synthetic ST molecules that contain but one intrapolypeptide cystine disulfide bond among the pairs of Cys residues present. Enhanced antigenicity is provided to the synthetic monomeric ST by formation of two disulfide bonds between two intrapolypeptide pairs of Cys residues, while maximum antigenic activity is provided by the formation of three intrapolypeptide disulfide bonds between three pairs of Cys residues. For multimeric forms of synthetic ST, at least one intramolecular, intrapolypeptide cystine disulfide bond or one intramolecular, interpolypeptide cystine disulfide bond is present, as is discussed hereinafter.

The synthetic ST utilized herein is described as being in monomeric and multimeric forms. Monomeric synthetic ST contains at least the fourteen amino acid residues (14-mer) shown below in Formula I, including the various R-groups described. Multimeric synthetic ST contains a plurality of at least 14-mer synthetic ST repeating units. In one embodiment, the synthetic ST repeating units of the multimer are bonded together heat-to-tail; i.e., the amino-terminal amine of one repeating unit is bonded by an amide bond to the carboxy-terminal carboxyl of a second synthetic ST repeating unit to form a multimer containing at least two ST repeating units.

ST multimers containing ST repeating units bonded together head-to-tail will sometimes be referred to hereinafter as dimer, trimer, tetramer, and the like ST multimers to indicate the number of ST repeating units contained in the multimer. A dimer ST multimer will also sometimes be indicated by the shorthand formula ST/ST, a timer ST multimer by the shorthand formula ST/ST/ST, and the like, with each "ST" representing at least the 14-mer polypeptide whose sequence is shown in Formula I.

Another embodiment of this invention is an ST multimer that is referred to herein as "polymeric synthetic ST", as a "synthetic ST polymer" or as "P-ST". In that embodiment, the individual ST polypeptide repeating units are bonded together by interpolypeptide cystine disulfide bonds formed between and among the Cys residues of the ST repeating units. Each of the ST repeating units of polymeric syntehtic ST also contains at least the fourteen amino acid residues illustrated in Formula I.

The multimeric forms of ST of this invention may also be described in terms frequently used in polymer chemistry. Using such terminology, the head-to-tail multimeric ST, whose repeating units having an ST amino acid residue sequence are bonded together by an amide bond between the carboxy-terminal carboxyl group of one repeating unit and the amino-terminal amine group of a second repeating unit may also be described as a straight-chain ST oligopolymer (oligomer), or as a block oligomer whose repeating blocks have the amino acid residue sequence of an ST polypeptide. The beforedescribed polymeric ST whose repeating units having an ST amino acid residue sequence are bonded together by interpolypeptide cystine disulfide bonds is believed to be describable as a cross-linked or network polymer whose plurality of repeating units have the amino acid residue sequence of an ST polypeptide and whose cross-links are supplied by the interpolypeptide cystine disulfide bonds.

While retaining the above terminology, the above-described multimers containing repeating units having substantially only one ST amino acid residue sequence may be termed straight-chain ST homo-oligopolymers or cross-linked (network) homopolymers, respectively. The multimers may also contain repeating units having different amino acid residue sequences or lengths, in which case those multimers may be termed straight-chain ST co-oligopolymers or cross-linked (network) copolymers.

It must be understood that the above-described multimeric forms of synthetic ST represent only two of many possible ST multimers. For example, when the multimer referred to as a head-to-tail multimer or straight-chain homo-oligopolymer having two repeating units is prepared by the oxidation of a 36-residue first polypeptide having an amino acid residue sequence corresponding to that of two ST polypeptides, some polymeric ST having interpolypeptide cystine disulfide bonds (a network homopolymer) is also formed. The repeating units of that network homopolymer contain two of the 18-mer amino acid residue sequences of ST in the repeating unit. A copolymer may be prepared by the oxidation of 18-mer ST first polypeptides along with the above 36-mer multimeric ST first polypeptides to provide a network or cross-linked material whose repeating units have an ST polypeptide amino acid residue sequence.

The word "synthetic" is utilized herein to mean that the ST polypeptide molecule or polypeptide repeating unit has been built up by chemical means (chemically synthesized) rather than by a biological means (biologically synthesized) such as that of the naturally occurring ST-producing *E. coli* or by genetic engineering techniques. The synthetic polypeptides are therefore free from naturally occurring proteins and fragments thereof. The well known solid phase chemical synthesis in which blocked amino acid residues are added in a serial manner to provide a polypeptide is the preferred method of synthesis, and is discussed hereinafter.

A synthetic polypeptide according to this invention includes the amino acid sequence as a monomer, alone, or as a repeating unit in a multimer, taken from left to right and in the direction from amino-terminus to carboxy-terminus, represented by the sequence of Formula I:

Formula I $$R_m^{13}-\overset{R_a^1}{\overset{|}{\text{Cys}}}(R_g^7)\overset{R_b^2}{\overset{|}{\text{Cys}}}(R_h^8)\text{GluLeu}\underset{R_c^3}{\underset{|}{\text{Cys}}}(R_i^9)\overset{R_d^4}{\overset{|}{\text{Cys}}}(R_j^{10})\text{Tyr(Asn)}$$

$$\text{ProAla}\overset{R_e^5}{\overset{|}{\text{Cys}}}(R_k^{11})\text{Ala(Thr)Gly}\overset{R_f^6}{\overset{|}{\text{Cys}}}\ (R_l^{12})\text{Asn(Tyr)}$$

wherein the three specific amino acid residues in parentheses are each an alternative to the immediately preceding amino acid residue in the sequence;

a, b, c, d, e and f (a-f) and g, h, i, j, k and l (g-l) are integers each having a value of zero or one, with the proviso that if the value of any of a-f or g-l is zero, the corresponding $R_a{}^1$, $R_b{}^2$, $R_c{}^3$, $R_d{}^4$, $R_e{}^5$ or $R_f{}^6$ ($R_{a-f}{}^{1-6}$-) group or $R_g{}^7$, $R_h{}^8$, $R_i{}^9$, $R_j{}^{10}$, $R_k{}^{11}$ or $R_l{}^{12}$ ($R_{g-l}{}^{7-12}$-) group is absent, and when an $R_{a-f}{}^{1-6}$-group is absent the sulfur atom of the Cys residue having an absent $R_{a-f}{}^{1-6}$-group forms a cystine disulfide bond, while if the value of any one of a-f or g-l is one, the corresponding $R_{a-f}{}^{1-6}$- or $R_{g-l}{}^{7-12}$-group is present;

the $R_{a-f}{}^{1-6}$-groups when taken individually, are the same or different moieties bonded to the sulfur atom of the Cys residue and are selected from the group consisting of hydrogen, an alkyl group containing 1 to about 4 carbon atoms, a substituted alkyl group containing 2 to about 20 carbon atoms, an acyl group containing 1 to about 8 carbon atoms, and a substituted acyl group containing 2 to about 10 carbon atoms;

$R_{g-l}{}^{7-12}$ are the same or different alternative amino acid residues to each immediately preceding Cys residue; and at least two of a-f and two of g-l are zero and two Cys residues are present with the proviso that the synthetic polypeptide contains at least one intramolecular cystine disulfide bond formed from the at least two Cys residues present.

When in monomeric form, the above at least one disulfide bond is an intramolecular, intrapolypeptide cystine disulfide formed between the at least two Cys residues present in the antigenic polypeptide. When the antigenic polypeptide is in a multimeric form that contains a plurality of polypeptide repeating units, the above at least one disulfide bond may be an intramolecular, intrapolypeptide cystine disulfide formed between the at least two Cys residues present in each polypeptide repeating unit, or that disulfide bond may be an intramolecular, interpolypeptide cystine disulfide bond formed between one of the at least two Cys residues present in a first repeating unit and another one of the at least two Cys residues present in a second repeating unit. It is therefore seen that an intramolecular cystine disulfide bond is present in both monomeric and multimeric forms of ST. In the monomeric ST, that cystine disulfide bond is an intrapolypeptide bond, while in multimeric ST the disulfide may be an interpolypeptide or an intrapolypeptide bond.

In more preferred practice for the monomeric and multimeric forms of synthetic ST, with reference to the above antigenic synthetic polypeptide of Formula I:

"e" is zero when "a" is zero,
"d" is zero when "b" is zero, and
"f" is zero when "c" is zero; and
each of "g" and "k" is zero when "a" is zero,
each of "h" and "j" is zero when "b" is zero, and
each of "i" and "l" is zero when "c" is zero.

The sequence shown in Formula I without the three specific alternative amino acids and substituent and alternative R-groups corresponds to the carboxy-terminal fourteen amino acid residue sequence of ST Ib and is homologous to amino acid residues numbered 59-72 of ST Ia from the amino-terminus. The fourteen amino acid residues comprising amino acids 59-72 of ST Ia differ from the sequence illustrated above in Formula I without its alternative amino acids and R-groups at position 65 wherein an asparagine (Asn) residue replaces the tyrosine (Tyr) residue at the position numbered 11 from the amino-terminus of ST Ib (residue position 8 from the carboxy-terminus), and at position 72 (carboxy-terminus) wherein a tyrosine residue replaces the asparagine residue shown.

Thus, the Tyr residue to the immediate right of the forth Cys residue from the amino-terminus (Tyr-65) may be replaced by the Asn residue that is parenthesized in the above formula. A similar replacement of a Tyr residue for Asn residue may also occur at the carboxy-terminus, as is shown by the parenthesization of the final Tyr residue.

The analogous fourteen amino acid residue sequence from ST Ic is the same as that of ST Ib except for position 69 in ST Ic wherein a threonine (Thr) residue replaces an alanine (Ala) residue of ST Ib. That replacement is also illustrated in the above formula by the parenthesized Thr residue.

It is particularly preferred that at least one of the four amino-terminal amino acid residues present in the sequence of the eighteen residue ST Ib molecule also be present in its natural positional sequence in the synthetic ST. It is still more preferred that all four of those additional amino acids be present in synthetic ST in the same, natural positional sequence that they are present in ST Ib.

The preferred four additional amino acids at amino-terminus of the synthetic ST molecule correspond to amino acid numbers 55 through 58 of ST Ia and are identical to those four amino acids in ST Ib. Three of the four amino acids of ST Ic differ from those of either ST Ia or ST Ib at positions 55 through 58 of ST Ia. Thus, using the above parenthesized alternative naming system, the 4-amino acid polypeptide (4-mer) at the amino-terminus of the synthetic ST of Formula I in a most preferred embodiment has a sequence, taken from left to right and in the direction from amino-terminus to carboxy-terminus, represented, as shown below in Formula II:

   Formula II wherein the parenthesized amino acid may replace the immediately preceding amino acid residue.

The monomeric synthetic polypeptide contains at least one intramolecular, intrapolypeptide disulfide bond, more preferably two intramolecular, intrapolypeptide disulfide bonds and most preferably three intramolecular, intrapolypeptide disulfide bonds. The disulfide bonds are believed to be formed between the pairs of Cys residues of $R_a{}^1$ and $R_e{}^5$, and $R_b{}^2$ and $R_d{}^4$ as well as between the Cys residues of $R_c{}^3$ and $R_f{}^6$, when a-f have the value of zero.

However, the Cys residues of $R_a{}^1$ and $R_b{}^2$ as well as those of $R_c{}^3$ and $R_d{}^4$ are adjacent, contiguous pairs. Consequently, synthetic ST polypeptides containing one disulfide bond can have substantially similar secondary structures and antigenicities regardless of whether that single disulfide bond is formed between the Cys residues of $R_a{}^1$ and $R_e{}^5$ or of $R_b{}^2$ and $R_e{}^5$. Similar results pertain to secondary structures formed due to disulfide formation between the Cys residues of $R_a{}^1$ and $R_d{}^4$ rather than $R_b{}^2$ and $R_f{}^6$, and the like.

The first polypeptide that is synthesized prior to the oxidative formation of an intramolecular intrapolypeptide disulfide bond contains at least two Cys residues, so the value of at least two of g-l are zero and the corresponding $R_g$-$j^{7-12}$ groups are absent. In view of the similarity of secondary structur that is provided by formation of an intramolecular, intrapolypeptide cystine disulfide bond between one of two contiguous Cys residues and another Cys residue, a proviso is added for preferred monomeric and multimeric synthetic ST that at least one pair of non-contiguous Cys residues from the Cys residues preceding the $R_g$-$j^{7-12}$ groups is present. That pair is selected from the group consisting of Cys residues that precede $R_g^7$, $R_h^8$ and $R_i^9$, $R_j^{10}$, $R_g^7$, $R_h^8$ and $R_k^{11}$, and $R_i^9$, $R_j^{10}$ and $R_l^{12}$. In terms of the amino acid residue positions in ST Ib, the pairs of non-contiguous Cys residues in monomeric synthetic ST are selected from the group consisting of those numbered 5 or 6 and 9 or 10, 5 or 6 and 14, and 9 or 10 and 17 from the amino-terminus of the ST Ib 18-mer polypeptide.

Multimeric synthetic ST molecules that are bonded together head-to-tail preferably contain at least one intramolecular, intrapolypeptide cystine disulfide bond per repeating unit. The intrapolypeptide cystine disulfide bonds present in each repeating unit of such multimers are preferably between the same Cys residues as those present in the monomeric molecules. The presence of two intrapolypeptide bonds between Cys residues of each repeating unit is still more preferred, while the presence of three intrapolypeptide cystine disulfide bonds per repeating unit is mot preferred.

For the polymeric synthetic ST molecules wherein the polypeptide ST repeating units are bonded together by intramolecular, interpolypeptide cystine disulfide bonds, it is not believed necessary that the two Cys residues present be non-contiguous. It is preferred, however, that those Cys residues be non-contiguous as discussed above.

In addition to its primary amino acid residue sequence, a monomeric synthetic ST molecule containing one intrapolypeptide cystine disulfide bond among its six Cys residue is also conveniently characterized by its antigenic activity being at least about 10 percent of the antigenic activity of biologic ST containing three disulfide bonds. Differences in thin layer chromatographic and electrophoretic mobilities between monomeric synthetic ST molecules containing three intramolecular, intrapolypeptide disulfide bonds and literature values for biologic ST can also be useful in characterizing synthetic ST molecules containing one intramolecular, intrapolypeptide disulfide bond when such a synthetic ST can form three intramolecular, intrapolypeptide cystine disulfides.

Since similar pairings of Cys residues other than those that are particularly preferred can also occur for monomeric synthetic ST molecules containing two intramolecular, intrapolypeptide disulfide bonds, such ST molecules are also conveniently characterized by having an antigenic activity that is at least about 10 percent of that of biologic ST containing three disulfide bonds. Thin layer chromatographic and electrophoritic mobilities are again useful in characterizing monomeric synthetic ST molecules containing two intramolecular, intrapolypeptide disulfide bonds when the third disulfide can also be formed.

The antigenicity of a synthetic ST as a percentage of the antigenicity of biologic ST is discussed in detail hereinafter in Section II. Broadly, however, the percentage of antigenicity of a synthetic ST is a relative measure of the amount of anti-biologic ST antibody that recognizes a synthetic ST compared to biologic ST recognized by the same anti-biologic ST antibodies. Antigenicity calculations are based upon the weight of ST antigen used, and are independent of whether the antigen assayed is monomeric or multimeric.

Suitable antigenicity has also been found for synthetic ST molecules wherein the sulfur atoms of Cys residues comprise portions of linkages other than cystine disulfide linkages. Because of that fact, the Cys residues of the above sequence of Formula I for synthetic ST are shown as bonded to $R_{a\text{-}f}^{1\text{-}6}$ groups whose identities are discussed hereinbelow.

It is noted however, that because at least one intramolecular, intrapolypeptide cystine disulfide bond is required for antigenic activity in the monomeric sytnethic ST, and biological activity when that is desired, all six of the $R_{a\text{-}f}^{1\text{-}6}$ groups may not be present in one synthetic ST molecule. Rather, only four of those groups may be present in any one molecule. Thus, for example, where the Cys residues of $R_a^1$ and $R_e^5$ are combined to form an intramolecular, intrapolypeptide cystine disulfide bond, the values of "a" and "e" are zero (below), the $R_a^1$- and $R_e^5$-groups are absent and only $R_b^2$, $R_c^3$, $R_d^4$, and $R_f^6$ may be present in a monomeric synthetic ST molecule.

To account for the presence of one, two or three intramolecular disulfide bonds of cystine residues formed among the six Cys residues, each of the R-groups 1–6 has also been labeled with a subscript letter a–f. Each subscript letter represents an integer having a value of zero or one. For more preferred embodiments, the proviso is added that "e" is zero when "a" is zero, "d" is zero when "b" is zero, and "f" is zero when "c" is zero, with the further proviso that at least one of "a", "b" or "c" must be zero, with the still further proviso that a disulfide bond is present between the respective pairs of Cys residues for which one subscript value of zero requires another subscript value to also be zero.

Each of the $R_{a\text{-}f}^{1\text{-}6}$-groups present in the synthetic ST may be hydrogen. In such a case, the Cys residue to which $R_{a\text{-}f}^{1\text{-}6}$-group is bonded is unsubstituted inasmuch as hydrogen is a normal group bonded to the sulfur atom of a Cys residue. The presence of hydrogen bonded to the sulfur atom of a cysteine is denoted herein by the designations Cys or CysH.

The $R_{a\text{-}f}^{1\text{-}6}$-groups may also be alkyl groups that contain 1 to about 4 carbon atoms. Exemplary of such $R_{a\text{-}f}^{1\text{-}6}$-groups are methyl, ethyl, propyl, i-propyl, n-butyl, i-butyl, and the like.

The $R_{a\text{-}f}^{1\text{-}6}$-groups may further be substituted alkyl groups containing 2 to about 20 carbon atoms wherein the substituents include aryl, substituted aryl, hydroxy, amino, carboxy, carboxamido, halo, substituted vinyl, substituted thio groups, and the like. Exemplary of such substituted alkyl groups are benzyl, alpha-tolyl, 2-hydroxyethyl, 2-hydroxypropyl, 2-aminoethyl, carboxymethyl ($—CH_2CO_2H$), carboxamido methyl ($—CH_2CONH_2$), p-chlorobenzyl, ethylene bis-acrylyl, 2-thioethane carboxy ($—SCH_2CH_2CO_2H$), and the like.

Included among the substituted alkyl groups from which the $R_{a\text{-}f}^{1\text{-}6}$-groups may be selected is a linking group useful for bonding the synthetic ST to another molecule such as an antigen carrier like the B subunit of an *E. coli* heat-labile (LT) toxin. Exemplary of such linking groups are diacrylates such as ethylene bis-acrylate which can react one double bond with a sulfur atom of a Cys group through a Michael addition reaction while leaving the second double bond free for bonding to a carrier; thioacetic acid, thiopropionic acid, cysteine and N-2-hydroxyethyl-2-thiosuccinimide which can form mixed disulfide bonds with a Cys residue sulfur atom and can react with another molecule such as a carrier through their carboxyl groups, the cysteine amino group or the hydroxyethyl group, respectively.

An $R_{a-f}^{1-6}$-group, in less preferred practice, can be an acyl group containing 1 to about 8 carbon atoms, or a substituted acyl group containing 2 to about 10 carbon atoms. Exemplary acyl groups containing 1 to about 8 carbon atoms include formyl, acetyl, propionyl, hexanoyl, benzoyl and the like. Exemplary substituted acyl groups containing 2 to about 10 carbon atoms include 2-methoxyacetyl, 3-ethoxypropionyl, 4-chlorobenzoyl, 3-carboxypropionyl (a maleic anhydride adduct), and the like. Acyl and substituted acyl groups are less preferred because their thioester bonds are not particularly stable in aqueous media.

The $R_{a-f}^{1-6}$-groups may be present separately in a synthetic ST molecule, or mixtures of $R_{a-f}^{1-6}$-groups may be present in one ST molecule. When all of the subscript letters a–f of a monomeric synthetic ST molecule have a value of zero, the $R_{a-f}^{1-6}$-groups are absent, and three intramolecular, intrapolypeptide cystine disulfide bonds are present.

The subscript letters a–f may also all have values of zero and the $R_{a-f}^{1-6}$-groups be absent in a polymerized synthetic ST molecule (P-ST) wherein intramolecular, interpolypeptide cystine disulfide bonds between synthetic ST polypeptide repeating units are present. Intramolecular, intrapolypeptide disulfide bonds within the synthetic ST repeating units may also be present in P-ST. On the average, the repeating units of such a polymer contain at least about two such interpolypeptide cystine bonds per repeating unit. Consequently, in preferred practice at least two of a–f and two of g–l have a value of zero for such polypeptide repeating units, and at least two $R_{a-f}^{1-6}$-groups and two corresponding $R_{g-l}^{7-12}$-groups are absent due to the formation of the at least two interpolypeptide cystine disulfide bonds.

Antigenicity and biological activity can also be obtained using synthetic ST molecules containing at least one intramolecular, intrapolypeptide cystine disulfide bond between the pairs of Cys residues such as those shown in Formula I as bonded to $R_a^1$ and $R_e^5$, $R_b^2$ and $R_d^4$, or $R_c^3$ and $R_f^6$, corresponding to the positions numbered 5 and 10, 6 and 14, and 9 and 17 from the amino-terminus of the ST Ib molecule, respectively, when the Cys residues not included in the disulfide bond are replaced by the same or different alternative amino acid residues. The preferred alternative amino acid residues to the Cys residues of Formula I provide no ionic charge to the synthetic polypeptide when the synthetic polypeptide is dissolved in an aqueous solution of physiological pH values; i.e., the preferred alternative amino acid residues are free from ionic charges when part of the polypeptide and in aqueous solution.

The alternative amino acid residues to the non-disulfide-bonding Cys groups are illustrated in the above Formula I by the parenthesized groups $R_g^7$, $R_h^8$, $R_i^9$, $R_j^{10}$, $R_k^{11}$ and $R_l^{12}$ each of which can replace the preceding Cys residue, and wherein the subscripts g–l are integers having the value of zero or one. In preferred synthetic ST polypeptides, if "a" is zero, "g" and "k" are each zero; if "b" is zero, "h" and "j" are each zero; and if "c" is zero, "i" and "l" are each zero.

The amino acid residues alanine (Ala) and serine (Ser) are exemplary of preferred alternative amino acids that are useful for replacing Cys residues. Biological and antigenic activities provided by synthetic ST molecules having Cys residues replaced by Ser residues are illustrated hereinafter.

The above disclosure as to groups $R_a^1$–$R_f^6$ and $R_g^7$–$R_l^{12}$ is equally applicable to synthetic ST polypeptides containing the fourteen amino acid residues shown in Formula I and to the more preferred synthetic ST polypeptide containing 18-amino acid residues whose sequence, taken from left to right and in the direction from amino-terminus to carboxy-terminus, is represented by Formula III, below:

Formula III $$\text{Asn(Ser)Thr(Ser)Phe(Asn)TyrCys}(\overset{R_a^1}{|})(R_g^7)\text{Cys}(\overset{R_b^2}{|})(R_h^8)\text{Glu}$$

$$\text{LeuCys}(\overset{R_d^4}{|})(R_i^9)\text{Cys}(R_j^{10})\text{Tyr(Asn)ProAlaCys}(\overset{R_e^5}{|})(R_k^{11})\text{Ala(Thr)Gly}$$
$$\underset{R_c^3}{|}$$

$$\text{Cys}(\overset{R_f^6}{|})(R_l^{12})\text{Asn(Tyr)}$$

wherein the parenthesized amino acid residues, and $R_a^1$–$R_f^6$ and $R_g^7$–$R_l^{12}$ are as defined hereinbefore.

Both the preferred synthetic polypeptide of Formula I and the more preferred synthetic polypeptide of Formula III may also include an additional group $R_m^{13}$ bonded to the amine of amino-terminal residue of the polypeptide, wherein "m" is an integer having the value of zero or one, with the proviso that if the value of "m" is zero, $R_m^{13}$ is absent and the amino-terminal amine is unsubstituted. If the value of "m" is one, $R_m^{13}$ may be a peptide containing 1 to about 58 amino acid residues, a linking group, and the acyl portion of a carboxylic acid containing 1 to about 20 carbon atoms forming an amide bond with the amine of amino-terminal residue.

When $R_m^{13}$ includes additional amino acid residues bonded to the amino-terminus of the synthetic polypeptide of the fourteen residue polypeptide of Formula I, the additional amino acid residues in one preferred embodiment have the sequence, from the amino-terminus to the carboxy-terminus, shown before in Formula II. Addition of the amino acid residue sequence of Formula II to the preferred fourteen amino acid residue sequence provides the sequence of the more preferred eighteen amino acid residue polypeptide of Formula III which itself corresponds to the carboxy-terminal amino acid residue sequences of ST Ia and ST Ic and the entire ST Ib sequence written together as one sequence.

In preferred practice for the fourteen residue polypeptide, the value of "m" is one and $R_m^{13}$ is a chain containing the four amino acid residue sequence of Formula II. In still more preferred practice, the alternative, parenthesized, amino acid residues of Formula II are absent and $R_m^{13}$ is a peptide chain containing the amino acid residue sequence of the four amino-terminal residues of ST Ib; i.e. AsnThrPheTyr, from left to right and in the direction from amino-terminus to carboxy-terminus.

Bonding of 58 or 54 amino acid residues to the fourteen or eighteen residue, synthetic ST polypeptides, respectively, can provide a synthetic polypeptide sequence corresponding to the sequence of native ST Ia or ST Ic. However, since the preferred fourteen, and more preferred eighteen, amino acid residue sequences of Formulas I and III, respectfully, can provide antigenic and biological activities substantially the same as or better than those of the native ST, synthetic polypeptides containing amino acid sequences longer than about the eighteen amino acid residues of Formula III so as to conform to the entire sequence of ST Ia and ST Ic are not necessary, nor are they desired. However, additional amino acid residues may be usefully bonded to the amino-terminus of the polypeptides of Formulas I and III.

Thus, it can be desirable to include an additional Cys residue at the polypeptide amino-terminus to use as a means of affixing the synthetic polypeptide to another molecule, such as a carrier or a linking group. When used under such conditions, it is convenient to use a sulfur atom blocking group other than a conventional solid phase blocking group lest the added amino-terminal Cys form a cystine disulfide bond with a Cys residue internal to the sequence. One way that a Cys sulfur atom may be blocked during synthesis and selectively deblocked is through the use of an isothiourea analogue of Cys which on cleavage results in the formation of a Cys residue.

In another preferred embodiment, a plurality of 14-mer or 18-mer synthetic ST polypeptides may be bonded together in a head-to-tail manner to form one multimeric ST embodiment of this invention. This multimer contains at least two of the antigenic ST polypeptides and preferably two to three of such repeating units, bonded together through an amide bond formed between the amino group of the amino-terminus of one polypeptide and the carboxyl group of the carboxy-terminus of the second polypeptide. An exemplary head-to-tail multimeric ST containing thirty-six amino acid residues, and having the amino acid residue sequence of two ST Ib polypeptides as repeating units is described in detail hereinafter.

Each of the additional ST repeating units can have the sequence shown in Formula I, hereinbefore. Multimeric synthetic ST molecules that contain a plurality of synthetic ST repeating units bonded head-to-tail can be prepared by the solid phase synthetic method described hereinafter in Section II. Because of the difficulties involved with synthesizing large polypeptide molecules, it is preferred that such head-to-tail multimers contain about 2 to about 3 ST repeating units.

In still another preferred embodiment, the $R_m^{13}$ group may be synthetic polypeptide whose amino acid residue sequence corresponds to a protein or polypeptide other than ST. For example, determinant amino acid residue sequences from a toxin such as that of the E. coli LT B subunit may be utilized to provide a combined immunogen or antigen against both toxins. Useful amino acid residue sequences that correspond to determinants of the LT B subunit have been found to exist at positions 37 through 62 [LT B-(37–62)] and at positions 27–36 [LT B-(27–36)] from the amino-terminus of the LT B whose complete amino acid residue sequence was reported by Dallas et al., Nature, 288: 499–501 (1982). Those amino acid residue sequences are shown below from left to right and in the direction of amino-terminus to carboxy-terminus:

LT B-(37–62) MetValIleIluThrPheMetSerGly GluThrPheGlnValGluValProGlySerGln-HisIleAspSerGlnLys, and LT B-(27–36) TyrThrGluSerMetAlaGlyLysArgGlu.

The carboxy group of the carboxy-terminal residue of either of the above polypeptides may be bonded to the amine of the amino-terminal residue of ST by an amide bond therebetween. Such bonding provides another example of head-to-tail bonding as is useful in some multimeric ST embodiments, as described before. The LT B-(27–36) and LT B-(37–62) polypeptides may also be bonded together head-to-tail to provide an $R_m^{13}$ having the entire sequence from position 27 through 62 of the LT B subunit to the amino-terminus of ST.

It is particularly convenient to synthesize an unoxidized first ST polypeptide having the above LT B polypeptide bonded to the amino-terminal ST residue using the before discussed stepwise, solid phase technique. That first polypeptide is then oxidized to provide the amino-terminal, $R_m^{13}$-group substituted ST. Such ST molecules will be referred to hereinafter as LT B-(27–36)—ST or LT B-(37–62)—ST to indicate the presence of either of the LT Bsubunit-related polypeptides as bonded to an ST.

Each of the above LT B-(27–36)—ST and LT B-(37–62)—ST polypeptides was coupled separately to an equal weight of tetanus toxoid using glutaraldehyde in a matter similar to that dicussed in Section VI A hereinafter. Vaccines prepared from 400 micrograms of the purified conjugates was injected into separate rabbits in complete Freund's adjuvant followed fourteen days later with boosts of the same amount of immunogen in incomplete Freund's adjuvant, and seven days thereafter with boosts of the same amount of immunogen in alum. Seven days thereafter (day 28), the rabbits were bled and antibodies to ST and to the B subunit were collected. Titers of those antibodies against native B subunit and synthetic ST provided values of 10 and 160–320, respectively, for the LT B-(27–36)—ST immunogen, and values of 160 and 1280, respectively, for the LT B-(37–62)—ST immunogen. Thus, the conjugates of both linked polypeptides are immunogenic, as well as antigenic (Table 2).

The $R_m^{13}$ group may also be linking group in addition to an added Cys residue. Included among such linking groups are the reaction products of the synthetic polypeptide and: (i) omega-aminomonocarboxylic acids containing about 3 to about 6 carbon atoms such as beta-alanine and 6-aminohexanoic acid, (ii) a dicarboxylic acid or acid chloride or acid anhydride containing about 3 to about 8 carbon atoms such as maleic acid, fumaric acid, succinic anhydride, phthalic anhydride, and the like, (iii) a blocked mercaptan-containing carboxylic acid including 2 to about 4 carbon atoms in the acid chain such as an isothiourea a derivative of thioglycolic or thiopropionic acids, (iv) a dialdehyde containing about 2 to about 8 carbon atoms such as gluteraldehyde or p-phthaldehyde, and the like.

Thus, linking groups containing free amino, carboxyl, mercapto and aldehydo groups can be provided for use in bonding the synthetic polypeptide to another molecule such as a carrier.

$R_m^{13}$ may also be the acyl portion of a monocarboxylic acid containing 1 to about 20 carbon atoms forming an amide bond with the amine of the amino-terminal residue of the synthetic polypeptide. Exemplarly of such monocarboxylic acid groups are acetic, propionic, hexanoic, lauric, myristic, stearic, oleic acids, and the like. A long chain fatty acid $R_m^{13}$ group such as stearoyl is usefully bonded to a synthetic ST for passive hemagglutination assays, while short chained $R_m^{13}$ groups such as acetyl bonded to ST provide antigenic activities that are slightly reduced compared to the underivatized eighteen residue polypeptide.

Thus, the synthetic ST polypeptides of Formulas I and III containing the $R_m^{13}$-group can be represented by the amino acid residue sequences shown in Formulas I-A and III-A below, taken from left to right and in the direction from amino-terminus to carboxy-terminus:

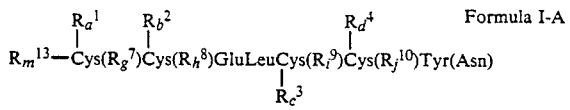

Formula I-A

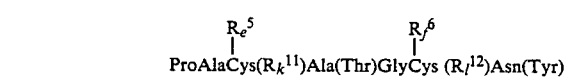

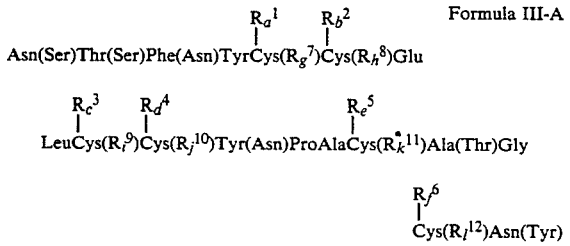

Formula III-A wherein each specific amino acid residue in parentheses is an alternative to the immediately preceding amino acid residue, and $R_{a\text{-}f}^{1\text{-}6}$-, $R_{g\text{-}l}^{7\text{-}12}$- and $R_m^{13}$-groups are as before described.

An embod

A typical 14-residue first monomeric polypeptide so produced is represented by the amino acid residue sequence, taken from left to right, and in the direction from amino-terminus to carboxy-terminus, shown in Formula V, below:

Cys($R_g^7$)Cys($R_h^8$)GluLeuCys($R_i^9$)Cys($R_j^{10}$)          Formula V
    Tyr(Asn)ProAlaCys($R_k^{11}$)Ala(Thr)GlyCys($R_l^{12}$)Asn(Tyr)

wherein each of the three specific amino acid residues in parentheses is an alternative to the immediately preceding amino acid residue, and $R_{g\text{-}l}^{7\text{-}12}$ are as defined hereinbefore.

A typical 18-amino acid residue-containing synthetic first monomeric polypeptide so produced is represented by the amino acid residue sequence, taken from left to right in the direction from amino-terminus to carboxy-terminus, shown in Formula VI, below:

Asn(Ser)Thr(Ser)Phe(Asn)TyrCys($R_g^7$)Cys($R_h^8$)Glu   Formula VI
    LeuCys($R_i^9$)Cys($R_j^{10}$)Tyr(Asn)ProAlaCys($R_k^{11}$)Ala(Tyr)

GlyCys($R_l^{12}$)Asn(Tyr)

wherein each of the six specific amino acid residues in parentheses is an alternative to the immediately preceding amino acid residue, and $R_{g\text{-}l}^{7\text{-}12}$ are as defined hereinabove.

A first, monomeric polypeptide whose amino acid sequence corresponds to the sequences shown in Formulas I or III may also be prepared in which at least two of a-f and g-l are zero, so that at least two Cys (CysH) residues are present as discussed previously. Such polypeptides may also include the previously discussed $R_m^{13}$ group.

The first, monomeric polypeptide can be utilized in the oxidation step in the state of purity obtained after the above lyophilization or its purity can be increased by passage through chromatographic columns containing Sephadex G-10 or G-50 resins (Pharmacia, Piscataway, N.J.) and/or DEAE-Sephacel (Pharmacia) following the method of Staples et al., supra. In either case, it is important that the first, monomeric polypeptide so made be protected from premature oxidation. Consequently, manipulations on the first, monomeric polypeptide subsequent to its cleavage from the resin support and removal of protecting groups from functional group-containing amino acid residues are carried out under non-oxidizing conditions.

After oxidation of the Cys sulfhydryl groups to form the intramolecular cystine disulfide bonds, described hereinafter, there remained no free sulfhydryl groups. The presence or absence of free sulfhydryl groups, Cys mercapto groups, was determined by the method of Ellman, *Arch. Biochem. Biophys.*, 82: 70–77 (1959).

The crude, oxidized monomeric polypeptide product was purified by gel filtration on Sephadex G-10 (Pharmacia) followed by ion exchange chromatography on DEAE-Sephacel (Pharmacia). Amino acid analysis, gel and paper electrophoresis and other chromatographic data all indicated a homogenous product. The overall yield was approximately 25% of theory. Synthetic ST preparations prepared on 5 separate occasions were examined for biologic potency and antigenicity. All yielded substantially the same responses described herein for the preparation described.

The polymeric ST multimers whose plurality of ST repeating units are bonded together by intramolecular, interpolypeptide cystine disulfide bonds were prepared from the monomeric polypeptide products prepared above, following the oxidation procedure described hereinafter.

A first ST multimeric dimer (ST/ST) that is bonded together in a head-to-tail manner, was prepared by the above solid phase method. Here, a first ST/ST multimer, each of whose repeating units had the ST Ib 18-mer sequence, was prepared by serial addition of thirty-six appropriately blocked amino acid residues, following the above procedure for the 18-mer first ST polypeptide, and then repeating the same sequence for the next eighteen residues until the 36-mer first polypeptide was prepared.

OXIDATION PROCEDURE FOR MONOMERIC ST

A first polypeptide having the 18-residue sequence of ST Ib was prepared as discussed above, and had the amino acid residue sequence, taken from left to right in the direction from amino-terminus to carboxy-terminus, shown in Formula VII, below:

AsnThrPheTyrCysCysGluLeuCysCysTyrProAlaCys AlaGlyCysAsn Formula VII

This first polypeptide (50 milligrams) was added with gentle agitation to an aqueous 0.1 molar ammonium carbonate-containing solution (pH value 7.8–8.3) to provide a final concentration of 1 milligram of deblocked first polypeptide per milliliter of solution. Continued gentle stirring over a period of 5–15 minutes at room temperature provided a clear solution of the first polypeptide.

Gentle agitation at room temperature was continued for a total period of 8 hours during which time molecular oxygen ($O_2$) in the air was contacted with the solution as oxidizing agent to oxidize the six Cys residues and form three intramolecular, intrapolypeptide cystine disulfide bonds. The loss of free sulfhydryl groups was followed with Ellman reagent [Ellman, *Arch. Biochem. Biophys.*, 82: 70–77 (1959)], and was found to be 15%, 40%, 60% and 98% complete at 0.5, 1.5, 2.5 and 8.0 hours, respectively.

The resulting, oxidized polypeptide was collected by lyophilization. It could be used in crude from, but was purified by column chromatography.

The crude material was first passed through a Sephadex G-50 (Pharmacia) column (1.5×80 centimeters) equilibrated with 0.1 molar ammonium acetate. Fractions of 3.5 milliliters/20 minutes were collected with materials being found in fractions 12–15 and 22–28. The contents of these fractions were collected by lyophilization and provided 10 and 36 milligrams, respectively. The material in fractions 22–28 was monomeric synthetic ST as indicated by its elution being in the identical position found by chromatography of biologic ST. Polymeric synthtic ST whose preparation is discussed further hereinafter was also obtained by this separation.

The discussion hereinbelow relates to monomeric ST, and is followed by a discussion of the preparation of multimeric synthetic ST molecules under the sub-heading "Preparation of Multimeric ST".

The partially purified monomeric synthetic ST could again be used as is, but was purified still further by chromatography on a DEAE-Bio Gel A (Bio Rad, San Raphael, CA) column (1.0×25 centimeters). Elution was carried out using a stepwise gradient with the principal amount of material eluting between 50 and 100 millimolar sodium chloride. That material was collected by lyophilization.

The lyophilized material was redissolved in water and desalted on a Sephadex G-25 (Pharmacia) column. The resulting material was collected by lyophilization to yield 28 milligrams of pure, synthetic ST, representing a yield of 56 percent based upon the weight of the crude, first polypeptide. Amino acid analysis of the synthetic ST so prepared gave the following values based on an 18-residue polypeptide (theoretical in parentheses):

| | |
|---|---|
| aspartic acid | 1.93 (2.0) |
| threonine | 1.98 (2.0) |
| glutamic acid | 0.97 (1.0) |
| proline | 1.05 (1.0) |
| glycine | 1.00 (1.0) |
| alanine | 2.00 (2.0) |
| leucine | 1.05 (1.0) |
| tyrosine | 1.89 (2.0) |
| phenylalanine | 0.96 (1.0) |
| cysteine (as cysteic acid) | 5.80 (6.0) |

Figure 1:
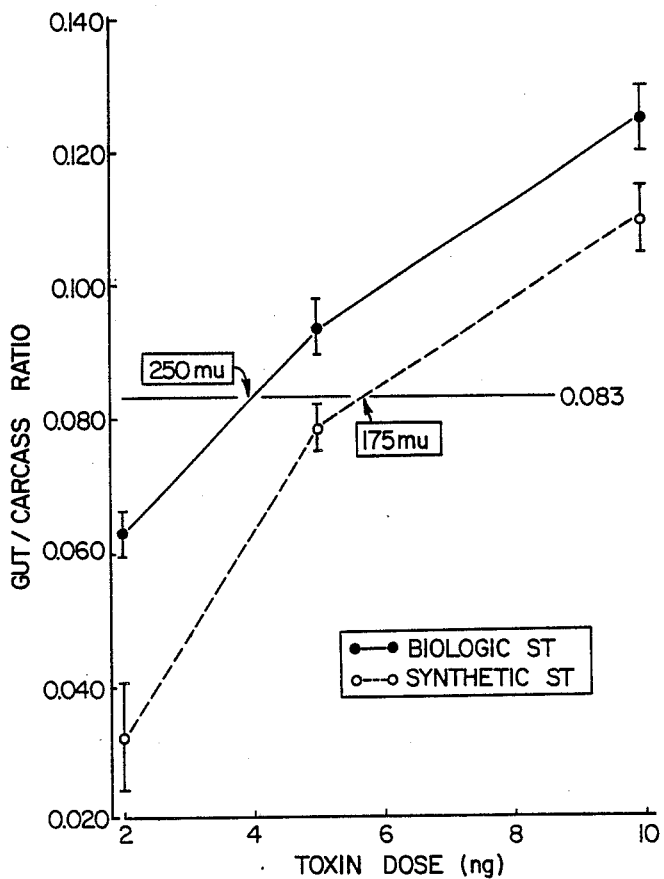
FIG. 1 illustrates the potency of synthetic and biologic ST in inducing fluid secretion in the suckling mouse assay. One mouse unit (MU) is defined as that amount of toxin which yields an intestinal (gut) weight-:carcass weight ratio of at least 0.083. Values of MU shown are per microgram of toxin. The abscissa shows toxin dosage in nanograms (ng).
Figure 2:
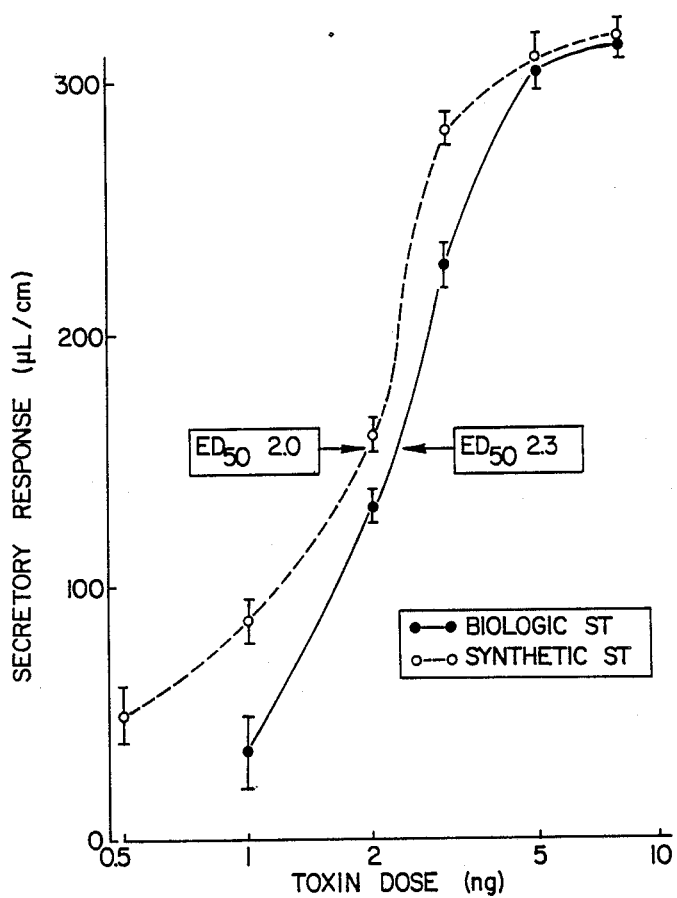
FIG. 2 illustrates fluid secretion following instillation of the toxins for 18 hours into ligated ileal loops of fasting rats. Values of the ordinate are in microliters of fluid per centimeter of intestinal length. Values of the abscissa are in nanograms of toxin dosage. The $ED_{50}$ signifies that dosage in nanograms which evokes one-half of the maximum secretory response.

The biological activity of this synthetic ST was determined by the suckling mouse assay of Giannella, *Infect. Immunity*, 14: 95–99 (1976), and was found to be substantially the same as biologic ST as is shown in FIG. 1. Substantial identity of secretory responses in ligated ileal loops between synthetic and biologic ST molecules is shown in FIG. 2.

Figure 3:
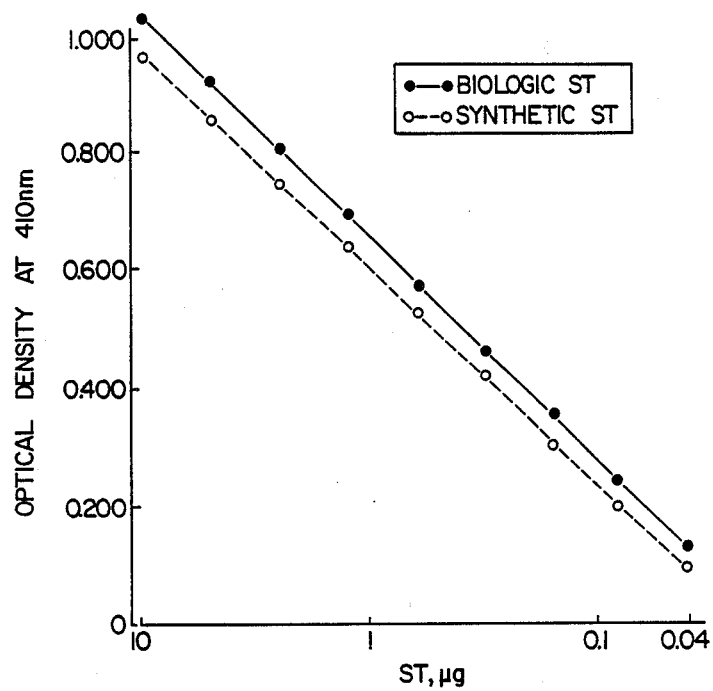
FIG. 3 illustrates the antigenicity of synthetic and biologic ST determined by a double sandwich ELISA technique using hyperimmune antisera to biologic ST. The antigenicity of the two ST toxins was substantially the same when tested against hyperimmune antisera to synthetic ST. The ordinate is in units of optical density, while the abscissa is in nanograms of ST as antigen.
Figure 4:
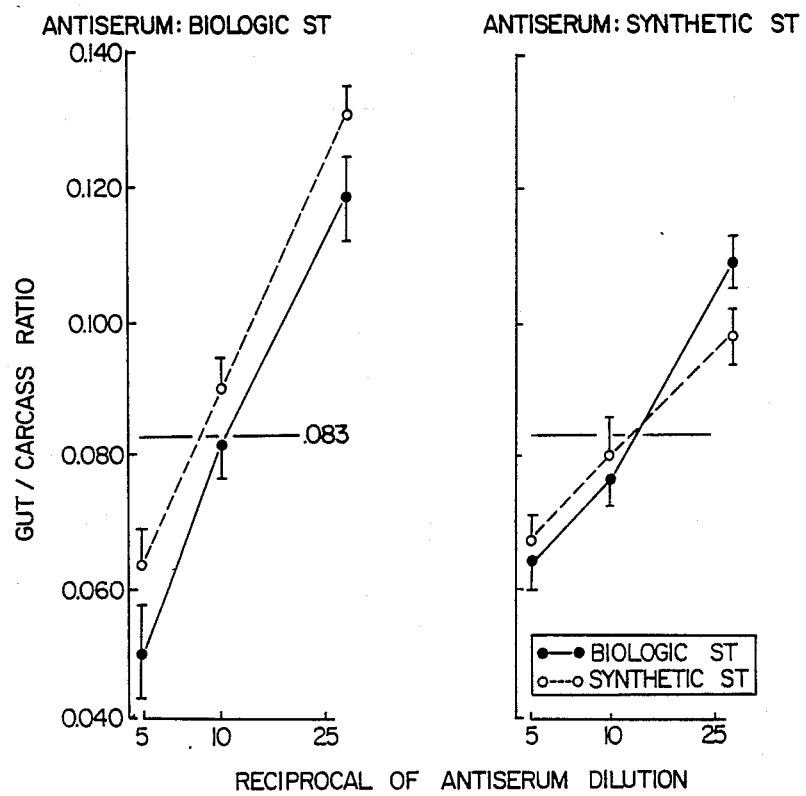
FIG. 4 illustrates the neutralizing effect of hyperimmune antisera to either synthetic or biologic ST on the secretory effect of toxins in the suckling mouse assay.
Figure 5:
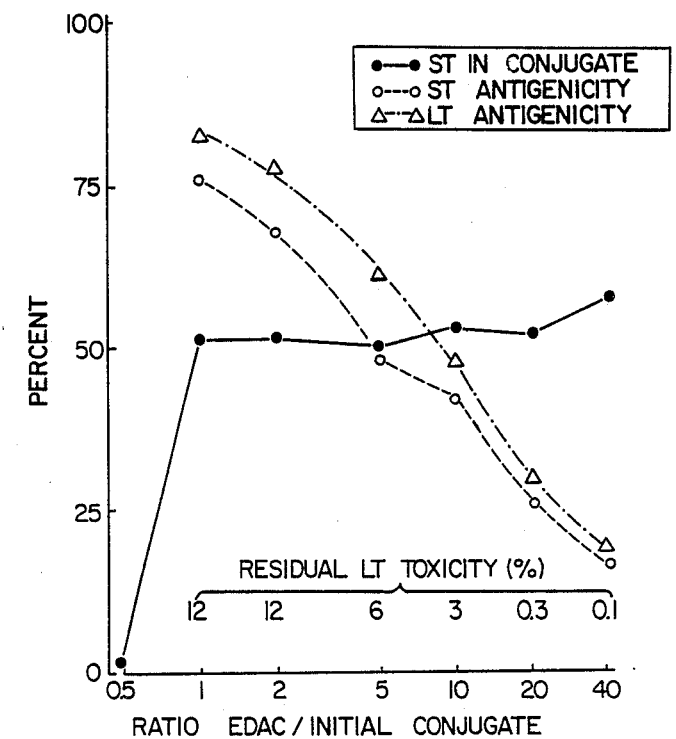
FIG. 5 shows the composition and properties of conjugates derived from conjugating an initial molar ratio of synthetic ST to the LT holotoxin of 100:1 in the presence of varying concentrations of the carbodiimide reagent 1-ethyl-3-(3-dimethylaminopropyl) carbodiimide (EDAC). Values for the percent of ST in the final conjugates (ordinate) are based on weight of Lowry protein [Lowry et al., *J. Biol. Chem.*, 193: 265–275 (1951)]. The second, inset, abscissa shows residual LT holotoxin toxicity in the conjugate as a percentage of the toxicity of non-conjugated LT holotoxin.
Figure 6:
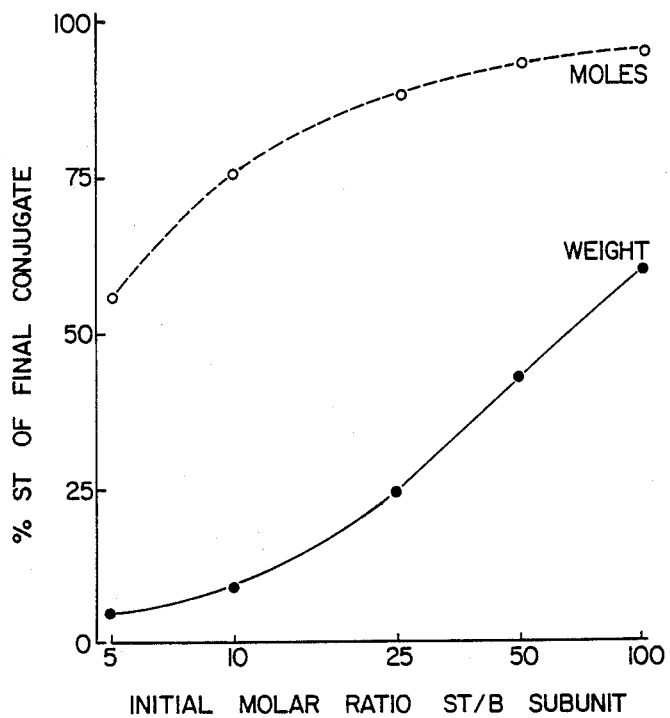
FIG. 6 illustrates the effect of the initial molar ratio of synthetic ST to LT B subunit on the amount of ST incorporated into the final conjugate as determined using a tracer dose of radioiodinated ST. The EDAC to conjugate ratio was 2:1.
Figure 7:
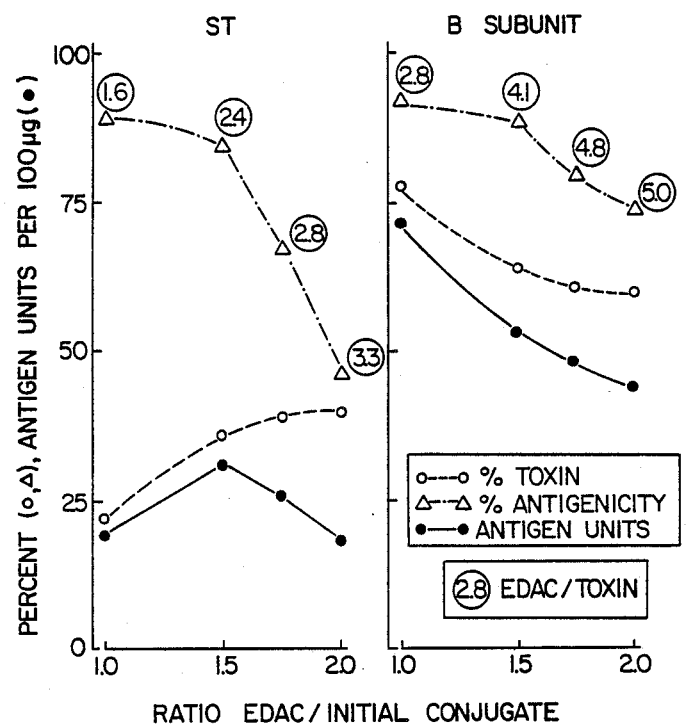
FIG. 7 illustrates the effect of varying the EDAC to conjugate ratio on the composition and antigenicity of conjugates obtained from an initial molar ratio of synthetic ST to B subunit of 50:1. Data for ST are shown in the left panel, while data for the B subunit are shown in the right panel. Antigen units, expressed per 100 micrograms of conjugate, were derived by multiplying the percentage of toxin present (by weight) times the percentage of antigenicity. Circled numbers indicate the ratio of EDAC to each specific toxin.
Figure 8:
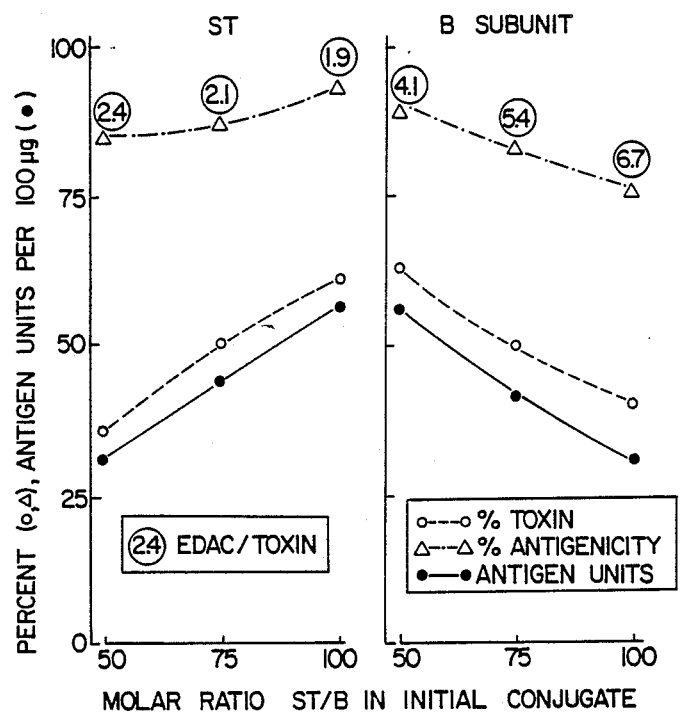
FIG. 8 illustrates the effect on composition and antigenicity of the conjugates of varying the initial molar ratio of synthetic ST to B subunit. The data are expressed as per FIG. 7. Circled numbers indicate the ratio of EDAC to each specific toxin. The EDAC to conjugate ratio was 1.5:1.

The more important antigenicity of synthetic ST was compared to that of biologic ST by reactivity to antibodies to biologic ST using the ELISA technique of Klipstein et al., *Infect Immunol.*, 37: 550–557 (1982). These results are illustrated in FIG. 3 which shows that the antigenicity of the synthetic ST of this preparation was about 70% that of biologic ST. However, FIG. 4 illustrates that seroneutralization on secretory effects by hyperimmune sera were almost identical.

LOCATION OF INTRAMOLECULAR DISULFIDE BONDS IN MONOMERIC ST

The three intramolecular, intrapolypeptide disulfide bonds were found to form at different rates. This finding permitted identification of the location of the pairs of Cys residues which combine to form the disulfide bonds.

Thus, further preparations of the above first polypeptide were oxidized under similar conditions and the free sulfhydryl groups were alkylated with iodoacetic acid or idoacetamide at various times during the oxidation reaction. The resulting partially oxidized-partially alkylated polypeptides were then sequenced using a Beckman Model 890 Sequencer (Beckman Instruments Co.) to determine which Cys residues were alkylated at which times during the oxidation reaction. The ratio of alkylated Cys residues at given positions in the partially alkylated-partially oxidized ST compared to the all alkylated-unoxidized ST reflected the location and order of formation of the disulfide bonds.

A ten-fold molar excess of alkylating agent was used over the moles of Cys residue. The oxidation-alkylation reaction mixture was stirred for a period of ten minutes subsequent to the addition of the alkylating agent, followed by addition of a ten fold excess of dithiothreitol over alkylating agent and a further stirring period of one hour to consume the alkylating agent.

The intramolecular, intrapolypeptide cystine disulfide bonds in the monomeric synthetic ST were found to be formed between the first and fifth, second and fourth, and third and sixth Cys residues from the amino-terminus; those Cys residues correspond to the residue of ST Ib numbered 5 and 10, 6 and 14, and 9 and 17, respectively, from the amino-terminus. Those Cys residues also correspond to the Cys residues bonded to $R_a{}^1$ and $R_e{}^5$, $R_b{}^2$ and $R_d{}^4$, and $R_c{}^3$ and $R_f{}^6$, respectively, whose positions from the carboxy-terminus in the 18-residue polypeptide herein prepared are analogous to the carboxy-terminal positions in the 14-residue polypeptide shown in Formula I.

The rate of formation was found to be in the order of the Cys residues of $R_b{}^2$ and $R_d{}^4$, followed by Cys residues of $R_c{}^3$ and $R_f{}^6$, and then followed by the Cys residues of $R_a{}^1$ and $R_e{}^5$. Using numbering from the amino-terminus of ST Ib, the order of disulfide bond formation was between the Cys residues numbered 6 and 14, then 9 and 17, followed by 5 and 10.

The primary and secondary structure of the monomeric synthetic ST so prepared, was, from amino-terminus to carboxyl-terminus, therefore:

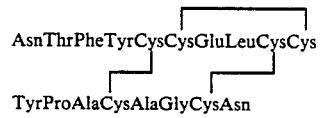

wherein the lines connecting the Cys residues represent the intramolecular, intrapolypeptide cystine disulfide bonds formed between those residues.

The rate of intramolecular, intrapolypeptide cystine disulfide bond formation as a function of pH value using the above human ST first polypeptide and oxidation with molecular oxygen contacted with a gently stirring solution containing 1 milligram per milliliter of the first polypeptide is shown below:

| pH value | Moles of —S—S— formed/hour |
|---|---|
| 5.0 | 0.30 |
| 6.0 | 0.45 |
| 7.0 | 0.90 |
| 8.0 | 1.50 |
| 9.0 | 1.20 |
| 10.0 | 0.75 |

Stirring speed and temperature also effect the rate of oxidation. Increases in either or both provide a more rapid rate of oxidation and disulfide bond formation.

A study was also carried out to assess the effect of the pH value at which the oxidation of the first polypeptide was conducted. Here, the above 18-mer first polypeptide was agin utilized, and was oxidized at room temperature, at a concentration of 1.0 milligrams per milliliter, and until no free sulfhydryl groups could be detected with Ellman reagent, as discussed before. The first polypeptides were dissolved in an aqueous solution containing 0.1 molar ammonia. After dissolution, the pH values of the solutions were lowered using a solution of 50 percent aqueous acetic acid. Antigenicities after lyophilization and without purification were determined relative to the antigenicity of biologic ST using the before-discussed ELISA technique. The results are shown below:

| pH value | Antigenicity (% of biologic ST) |
|---|---|
| 8.5 | 75 (39) |
| 8.0 | 60 (32) |
| 7.8 | 300 (159) |
| 7.7 | 250 (132) |
| 7.6 | 150 (79) |
| 7.4 | 23 (12) |
| 7.2 | 46 (24) |

COMPARISON OF PHYSICAL PROPERTIES OF MONOMERIC SYNTHETIC AND BIOLOGIC ST

Thin layer chromatography using cellulose coated plastic sheets (Eastman Kodak, Inc., Nutley, NJ) and a solvent of butanol:acetic acid:water (200:30:75 parts by volume, respectively) provided an $R_F$ value of 0.307 for the above prepared synthetic ST having three; intrapolypeptide disulfide bonds. Staples et al., supra, reported an $R_F$ value of 0.8–0.9 using the same solvent system and cellulose coated glass plates (Eastman).

Paper electrophoresis at pH 2.1, 500 volts for 90 minutes at room temperature provided an $R_F$ value of 0.80 relative to lysine for the above synthetic ST. Staples et al., supra, using thin layer electrophoresis on cellulose at pH 1.9 reported a mobility for biologic ST that was about the same as that of glutamic acid. Conversion of glutamic acid mobility under the Staples et al. condition to that of lysine under the conditions used for the synthetic ST provides a relative $R_F$ of 0.50 for biologic ST.

Preliminary results from optical rotatory dispersion determinations using the above synthetic ST and its biologic counterpart showed that the two molecules are different.

MONOMERIC SYNTHETIC ST MOLECULES CONTAINING TWO DISULFIDE BONDS

Synthetic 18-residue polypeptides analogous to human ST Ib molecules were prepared in a manner substantially the same as that described above, except that pairs of Cys residues were replaced in the first polypeptide and resulting, oxidized, monomeric ST molecules by alternative $R_{g-l}^{7-12}$-groups which provide no ionic charge to the synthetic ST polypeptide when that polypeptide is dissolved in aqueous solution at physiological pH values. The synthetic ST molecules so prepared were then assayed for their antigenic and biological activities. The $R_{g-l}^{7-12}$-groups used in these determinations were the amino acid serine (Ser).

The first polypeptide from which these synthetic ST Ib analogues were prepared had the amino acid sequence, taken from left to right in the direction from amino-terminus to carboxy-terminus, shown in Formula VIII, below:

Formula VIII

AsnThrPheTyrCys($R_g^7$)Cys($R_h^8$)GluLeuCys($R_i^9$)Cys($R_j^{10}$)
TyrProAlaCys($R_k^{11}$)AlaGlyCys($R_l^{12}$)Asn wherein each of the $R_{g-l}^{7-12}$-groups was an alternative Ser residue to the immediately preceding Cys residue.

For this group of immunological assays as well as for all of the other such assays, the haptenic synthetic ST Ib and biologic ST Ib molecules were first coupled to porcine immunoglobulin G (PIG) as a carrier in substantially the same amounts and under substantially the same conditions, as discussed in Section IV, hereinafter. Antisera were then raised to the immunogens so produced. The abilities of those two antisera to recognize each of the ST molecules were measured and compared by the before-discussed ELISA technique of Klipstein et al., *Infect. Immun.*, 37: 550–557 (1982). Recognitions of purified synthetic ST and biologic ST by their own antisera were set at 100% and the amounts of recognition for each of the other ST molecule was then calculated accordingly. The suckling mouse assay was used for determining biological activity.

Thus, for these comparative determinations, pairs of $R_{g-l}^{7-12}$ were utilized in which the value of four of g–l was zero, while the value of two of g–l was one. The pairs of alternative $R_{g-l}^{7-12}$-groups utilized were those whose preceding pairs of Cys residues are shown in Formula I for the 14-residue polypeptide to be bonded to the groups $R_a^1$ and $R_e^5$, $R_e^3$ and $R_f^6$, and $R_b^2$ and $R_d^4$. These groups correspond to the Cys residues numbered 5 and 10, 6 and 14, and 9 and 17, respectively, from the amino-terminus of the ST Ib amino acid sequence. The $R_{g-l}^{7-12}$-groups for which g–l were one were therefore $R_g^7$ and $R_k^{11}$, $R_i^9$ and $R_l^{12}$, and $R_h^8$ and $R_j^{10}$, respectively, of the amino acid sequence of Formula VIII. The results for these comparisons are shown in Table 1 below along with standards of biologic ST Ib, the above-prepared synthetic ST Ib and porcine ST Ia.

TABLE 1

Relative Antigenic and Biological Activities

| ST Assayed | Assay: Anti-Syn. ST[1] (Percent) | Anti-Biol.-ST[2] (Percent) | Suckling Mouse (Percent) |
|---|---|---|---|
| $R_g^7 + R_k^{11}$ Ser | 45 | 62 | 66 (8.2 ng[3]) |
| $R_i^9 + R_l^{12}$ Ser | 21 | 43 | 46 (12.0 ng[3]) |
| $R_h^8 + R_j^{10}$ Ser | 41 | 74 | 92 (6.0 ng[3]) |
| Biologic Ib | 35 | 100 | 100 (5.7 ng[3]) |
| Synthetic Ib | 100 | 263 | 120 (5.3 ng[3]) |
| Porcine Ia | 3 | 450[4] | 10 (55 ng[3]) |

[1]Percent recognition of assayed ST by antiserum raised to synthetic ST.
[2]Percent recognition of assayed ST by antiserum raised to biologic ST.
[3]Nanograms required to provide a gut: whole body ratio of 0.083.
[4]This value appears to be anomolously high by a factor of about 1.5 to about 2.

The results in the above Table illustrate several features of the present invention. First, substantial immunologic activity, e.g. antigenicity, can be obtained without the presence of three disulfide bonds in the ST molecule. Second, and a related feature, all of the Cys residues are not needed and some may be replaced by other amino acid residues. Third, biological activity which can lead to diarrhea in a vaccinated animal can be reduced while substantial antigenic activity is maintained.

A fourth feature of this invention that the above results illustrate is that the biologic ST Ib molecule and the synthetic ST Ib molecule containing three disulfide bonds are immunologically different entities, thereby underscoring the before-noted differences in chromatographic, electrophoretic and optical rotary dispersion chracteristics of the two molecules. Thus, antibodies to biologic ST recognized the synthetic ST 263% better than they recognized the biologic ST to which they were raised. Similarly, antibodies raised to the synthetic ST recognized biologic ST only 35% as well as they recognized the synthetic ST.

The difference between the synthetic and natural ST molecules is further underscored by the ST Ia (porcine) which was hardly recognized by antibodies to the synthetic ST, but was recognized about 10- to about 100-times better by antibodies raised to biologic ST than was biologic ST itself, taking into account the fact that the 450% value may be anomolously high. Even if the value of 450% is too high by a factor of about 5, the antibodies raised to biologic ST Ib recognized porcine ST Ia at least about 20-times better than did antibodies to the synthetic ST Ib. If the biologic and synthetic ST Ib molecules were the same, antibodies to each would be expected to recognize the porcine ST Ia with about the same efficiency. Since that was decidely not the case, the biologic ST Ib and synthetic ST Ib molecules must be different although both contain identical primary amino acid sequences and both contain three intramolecular disulfide bonds.

OTHER PREPARATIONS OF MONOMERIC ST

Additional first polypeptides and ST molecules have been prepared (i) via different oxidation routes, (ii) having different amino acid sequences from the ST Ib, (iii) replacements of different $R_g$-$i^{7-12}$-groups, (iv) alkylated Cys $R_a$-$f^{1-6}$-groups and (v) $R_m^{13}$ groups bonded to the N-terminal amino acid residue of the 18-residue ST Ib molecule. Many of these materials have been assayed for antigenic and/or biological activities by the above ELISA and suckling mouse techniques, respectively using antisera to the synthetic ST prepared in (3), below. The results of several of these preparations and assays are listed below in Table 2.

TABLE 2
Other Preparations

| Oxidations[1] | ELISA[2] (Percent) | Suckling[3] Mouse (Percent) |
|---|---|---|
| (1) Room temperature; 1.0 mg/ml; 0.1 $\underline{M}$ NH$_4$HCO$_3$; pH 8.0; 6 hrs. | 95 | 120 (5.3 ng) |
| (2) 4° C.; 1.0 mg/ml; 0.1 $\underline{M}$ NH$_4$HCO$_3$; pH 8.0; 6 hrs. | 87 | 80 (6.9 ng) |
| (3) Room temperature; 1.0 mg/ml; 0.1 $\underline{M}$ NH$_3$; pH 10.3; 1.0 hr.; lyophilized; 4° C.; 1.0 mg/ml; buffered saline; pH 7.2; 8 hrs. | 27 | 85 (6.5 ng) |
| (4) Room temperature; 1.0 mg/ml; 0.1 $\underline{M}$ NH$_3$; pH 10.3; adjusted with acetic acid to pH 8.0 after 5 minutes; 1 equivalent K$_3$Fe(CN)$_6$; 3 hrs. | less than 2 | N.D.[4] |
| (5) Room temperature; 2.0 mg/ml; 0.1 $\underline{M}$ NH$_3$; pH 10.3; 1 hr.; lyophilized; 4° C.; 2.0 mg/ml; buffered saline; 8 hrs. | 13 | 55 (10 ng) |
| (6) Room temperature; 1.0 mg/ml; 1.0 mg/ml; performic acid | much less than 1 | N.D. |
| (7) Room temperature; 1.0 mg/ml; 0.1 $\underline{M}$ NH$_3$; pH 10.3; adjusted immediately upon solution with acetic acid to pH 8.0; 22 hrs. | 53 | N.D. |
| (8) Room temperature; 1.0 mg/ml; 0.1 $\underline{M}$ NH$_3$; pH 10.3; 22 hrs. | 26 | N.D. |
| (9) Room temperature; 1.0 mg/ml; 0.1 $\underline{M}$ NH$_4$HCO$_3$; pH 8.0; 8 hrs.; Sephadex G-10 and DEAE-Bio Gel A; lyophylize. | 100 | N.D. |
| (10) Room temperature; 1 mg/ml; 8 $\underline{M}$ urea; pH 8.0; 8 hr. | 7 | N.D. |
| Alkylation | | |
| (11) Oxidize as per (1); alkylate with average of 4 moles iodoacetic acid after an average of one disulfide formed. | 12 | N.D. |
| (12) Oxidize as per (1); alkylate with average of 2 moles of iodoacetic acid after an average of two disulfides formed. | 14 | N.D. |
| Acyl ST ($R_m^{13}$) | | |
| (13) An N—acetyl group was added to the amino-terminus of the 18-amino acid residue of the first polypeptide prior to removal of the peptide blocking groups, followed by deblocking and oxidation as in (7). | 53 | N.D. |
| (14) LT B-(37–62)–ST; oxidized as per (1). | 147 | N.D. |
| (15) LT B-(27–36)–ST; room temperature; 0.1 mg/ml; 0.5 $\underline{M}$ NH$_4$HCO$_3$; pH 8.0; over night | 24 | N.D. |
| (16) LT B-(27–36)–ST; room temperature; 1.0 mg/ml; 0.5 $\underline{M}$ NH$_4$HCO$_3$; pH 8.0; over night | 121 | N.D. |
| (17) LT B-(27–36)–ST; room temperature; 5.0 mg/mlg 0.5 $\underline{M}$ NH$_4$HCO$_3$; pH 8.0; over night. | 92 | N.D. |
| Alternative sequences | | |
| (18) Carboxy-terminal 14 amino acids of ST Ib, oxidized as per (9). | 6[5] | N.D. |
| (19) Carboxy-terminal 15 amino acids of ST Ib, oxidized as per (9). | 55 | N.D. |
| (20) Cys residues preceding Formula VIII $R_h^8$ and $R_i^9$ replaced by Ser, oxidized as per (9). | 71 | N.D. |
| (21) Cys residues preceding Formula VIII $R_i^9$ and $R_k^{11}$ replaced by Ser, oxidized as per (9). | 152 | N.D. |
| (22) Cys residues preceding Formula VIII $R_j^{10}$ and $R_k^{11}$ replaced by Ser, oxidized as per (9). | 27 | N.D. |

[1]A first polypeptide corresponding to the sequence of Formula VIII wherein g-1 were zero was used for each of (1)–(17). First polypeptides corresponding to the ST Ib carboxy-terminal 14-amino acids and 15-amino acids were used in (18) and (19), respectively. First polypeptides corresponding to the noted substitutions to the sequence in Formula VIII were used for (20)–(22) and were then oxidized. Reaction conditions are provided in the order of temperature; concentration of first polypeptide in milligrams/milliliter; molar concentration of added ingredients; pH value at which oxidation was initiated; and duration of the oxidation procedure. Each solution was stirred gently to contact the solution with atmospheric molecular oxygen as oxidizing agent, unless otherwise specified. Preparations were assayed without further purification.
[2]The ELISA was conducted as per Table 1 with antisera raised to the ST prepared as in (3) as the basis for comparisons. That ST preparation was purified prior to coupling, while preparation (3) shows the results for the unpurified preparation.
[3]The suckling mouse assay was conducted as per Table 1 with percentages being based upon the value for biologic ST, the values in parentheses being nanograms of ST providing a gut: whole body ratio of 0.083.
[4]N.D. = Not determined.
[5]It is believed that the antigenicity value obtained is anomolously low.

The above results illustrate that the highest antigenic activity (ELISA) is achieved under oxidation conditions in which the first synthetic polypeptide is present in solution at a concentration of less than about 2 milligrams per milliliter, oxygen in the air is the oxidizing agent, the pH value is below about 10, and particularly where the pH value is about 7.5 to about 8.0, the temperature of the reaction is about zero to about 25° C. and the oxidation reaction time is less than about 24 hours.

PREPARATION OF MULTIMERIC ST

A. Multimeric Synthetic ST Dimer (ST/ST)

A first polypeptide having the 36-residue sequence of two ST Ib molecules joined head-to-tail by an amide bond was prepared by the stepwise, solid phase synthesis described before. The amino acid residue sequence of that material, taken from left to right and in the direction of amino-terminus to carboxy terminus, is shown in Formula IX, below:

Formula IX
AsnThrPheTyrCysCysGluLeuCysCysTyrProAlaCys
AlaGlyCysAsnAsnThrPheTyrCysCysGluLeuCysCysTyr
ProAlaCysAlaGlyCysAsn.

That molecule was then dissoled at a concentration of 1 milligram per milliliter in a 0.05 molar ammonium bicarbonate buffer having a pH value of 8.0. The resulting solution was stirred gently in the presence of atmospheric molecular oxygen as oxidant until free sulfhydryl groups could not be detected with Ellman reagent, supra; i.e., overnight. The ST/ST molecule so prepared were separated from the remaining materials in the reaction medium by column chromatography, freeze dried and were then used without further purification. Amino acid analysis of the 36-mer first polypeptide was consistent with the sequence shown in Formula IX.

The resulting ST/ST without further purification had an antigenicity to antibodies raised against natural, monomeric ST of 233 percent compared to the antigenicity of the natural ST Ib to those same antibodies. The biological activity of this ST/ST was less than one percent of that of natural ST Ib in the suckling mouse assay, supra, up to the limits of the assay, here 640 nanograms.

Synthetic trimer (ST/ST/ST), tetramer (ST/ST/ST/ST), and longer head-to-tail multimers of synthetic ST can be similarly prepared. Synthetic dimer and trimer ST molecules are particularly preferred because of the difficulties that attend in producing synthetic polypeptides that contain more than a total of about sixty amino acid residues.

Results using the synthetic dimer (ST/ST) in the preparation of a vaccine are discussed in more detail hereinafter in Section V.

B. Multimeric Synthetic ST Polymer

The 18-mer first synthetic ST Ib polypeptide prepared as described previously was used illustratively for the preparation of synthetic ST polymers whose plurality of synthetic ST repeating units are linked together by intramolecular, interpolypeptide cystine disulfide bonds.

In an illustrative preparation, the polymeric synthetic ST (hereinafter sometimes referred to as P-ST) was prepared by dissolving the above prepared, first synthetic ST polypeptide (18-mer) in 0.1 molar ammonium bicarbonate buffer having a pH value of 8.0 to provide a solution having a concentration of about 1 milligram per milliliter of a first synthetic ST polypeptide. Volumes of such solutions of 10 to 100 milliliters have been used. The solution so prepared was stirred gently at room temperature in an open beaker to provide oxidation of the Cys mercaptans. Analysis of the reaction medium after an oxidation period of about 16-24 hours using Ellman reagent, supra, indicated that no free sulfhydryl groups were present.

The oxidized reaction medium was lyophilyzed and the resulting, dried material was resuspended in a 0.1 molar ammonium bicarbonate (pH 8.0-8.5) buffer, and was placed upon a Sephadex G-50 chromatography column equilibrated with same buffer for separation. A typical separation of polymeric synthetic ST (P-ST) from monomeric syntehtic ST (M-ST) is illustrated in the graph of FIG. 17 using such a column.

The ordinate of the graph is in units of optical density read at 278 nanometers. The abscissa shows numbered fractions of 4.5 milliliters each of eluate collected from the column. The eluate from fractions numbered 5-9 was collected as containing the P-ST, while fractions numbered 10-17 were collected as containing synthetic monomeric ST (M-ST).

Fractionation of P-ST so obtained using a column containing Bio Rad P-30 (Bio Rad, San Raphael, CA) as the separating resin indicated that the vast majority of the P-ST isolated using the Sephadex G-50 column had an average molecular weight of at least about 40,000 daltons (40 kd P-ST). Further fractionation of the 40 kd P-ST using Bio Gel A-1.5 m resin (Bio Rad) indicated that most of that material had an average molecular weight of about 400,000 daltons, with some material having a molecular weight of greater than about 1,500,000 daltons (1500 kd P-ST). Still further molecular weight fractionation using a column containing Bio Gel A-5 m resin (Bio Rad) resolved the 1500 kd P-ST into one fraction that included P-ST having a molecular weight of greater than about 15,000,000 daltons (15,000 kd P-ST) and a second fraction having an average molecular weight of about 4,000,000 daltons (4000 kd P-ST).

The above molecular weights are approximations based upon a presumed globular shape for the P-ST and a knowledge of the void volume and exclusion limits of the column, but without the use of internal standards having known molecular weights. Each of the above-obtained fractions was lyophilized after elution from the column.

The results desribed hereinafter (Sections V and VI) using P-ST are for lypophilized, Sephadex G-50 purified preparations that contain mostly polymer whose average molecular weight is at least about 40,000 daltons; i.e., the 40 kd P-ST. Work is presently underway relating to the antigenicity, immunogenicity and biologic activity of fractions of P-ST having varying molecular weights.

Typical preparations of 40 kd P-ST have an antigenicity to antibodies against natural ST Ib of between 900 and 1500 percent of the antigenicity of the natural material (ST Ib), and have a biological activity in the suckling mouse assay, supra, of about 20 percent or less than that of natural ST Ib.

GENERAL SYNTHETIC PROCEDURE

A general synthetic procedure for preparing a monomeric or multimeric synthetic ST molecule having at least about 10 percent of the antigenicity of biologic ST based upon the above results and several other determinations is as follows:

(1) A monomeric, first synthetic polypeptide is prepared in the substantial absence of oxidizing agent. The first synthetic polypeptide includes the amino acid residue sequences of Formula I, Formula III, Formula V, Formula VI or Formula IX, at least two Cys residues whose $R_{a\text{-}j}^{1\text{-}6}$-groups are hydrogen; i.e., two CysH residues, and is free from any intramolecular, cystine disulfide bonds, and may contain an $R_m{}^{13}$-group wherein "m" has a value of one.

(2) The first polypeptide so prepared is provided, and is dissolved or dispersed in an aqueous composition at a concentration of less than about 5 milligrams per milliliter, more preferably at a concentration of less than about 2 milligrams per milliliter, and most preferably at a concentration of about 1 milligram per milliliter to about 0.1 milligrams per milliliter. The pH value of the composition into which the first polypeptide is dissolved or dispersed is preferably alkaline and less than about 10.5, and more preferably is about 7.5 to about 10.5.

(3) The first polypeptide-containing composition is thereafter contacted with molecular oxygen in the air as an oxidizing agent. The pH of the solution during oxidation is preferably about 7.0 to about 9.5, and more preferably about 7.5 to about 9, and most preferably about 7.5 to about 8.0. The solution is preferably contacted with the oxidant by gentle stirring in a vessel open to the air.

(4) Contact between the composition and the air is maintained for a period of about 1 to about 24 hours, and more preferably for about 2 to about 8 hours, to form at least one intramolecular, intrapolypeptide or interpolypeptide cystine disulfide bond from the at least two Cys (CysH) residues present. For monomeric synthetic ST and head-to-tail ST multimers, the at least one cystine disulfide bond is an intramolecular, intrapolypeptide bond, while for the polymeric synthetic ST (P-ST) the at least one cystine disulfide is an intramolecular, interpolypeptide bond. It is preferred that each ST repeating unit of P-ST form an average of about two interpolypeptide cystine disulfide bonds so that P-ST molecules having more than two ST repeating units are formed.

In preferred practice for monomeric synthetic ST, the disulfide bond is formed between the Cys residues preceding the pairs $R_g{}^7$ and $R_k{}^{11}$, $R_h{}^8$ and $R_j{}^{10}$, and $R_i{}^9$ and $R_l{}^{12}$ of Formulas I, III, V or VI, which correspond to the positions of the residues numbered 5 and 10, 6 and 14, and 9 and 17 from the amino-terminus of the ST Ib molecule, respectively. In more preferred practice, contact between molecular oxygen and the solution is maintained for a period sufficient to form two disulfide bonds, preferably between the above-mentioned pairs of Cys residues, and still more preferably for a period sufficient to form three disulfide bonds, again preferably between said pairs of Cys residues.

The oxidation is preferably carried out at a temperature of about 0° C. to about 25° C.

(5) Upon completion of the oxidation reaction, the synthetic ST is typically collected as by lyophilization, and purified as by column chromatography.

III. USES OF MONOMERIC SYNTHETIC ST

The monomeric synthetic ST prepared as discussed above was linked to a carrier molecule or used alone in ELISA measurements in studies carried out under the direction of Dr. Frederick A. Klipstein of the University of Rochester Medical Center, Rochester, N.Y. The results of experimental determinations and the procedures for carrying out these determinations are discussed herein and in Section IV, hereinafter. Unless otherwise stated, the studies discussed in Sections III and IV were carried out with the monomeric synthetic ST (M-ST) of this invention.

A. Properties

ST Ib purified to homogeneity from human *E. coli* $LT^{31}/ST^+$ strain 18D (O42:H47) has an estimated molecular weight of 1,972 and consists of ten different amino acids arranged in a sequence of 18 amino acids [Staples et al., supra] whose primary structure was shown by Chan et al., supra, to be AsnThrPheTyrCys-CysGluLeuCysCysTyrProAlaCysAlaGlyCysAsn. A synthetic molecule with this primary structure was prepared (Section II) and the biological properties of this polypeptide were compared with that of pure ST obtained by bacterial growth of strain 18 D (biologic ST).

Capacity To Induce Fluid Secretion

Synthetic and biologic ST were substantially equally potent in their abilities to induce fluid secretion in the suckling mouse assay (FIG. 1) and rat ligated ileal loops (FIG. 2). The slight variations observed in the minimum effective dosages of the two toxins in each assay model were within the range of experimental variation, and, in fact, several subsequently prepared preparations of synthetic ST evoked an identical response to that of the native or biologic ST in the suckling mouse assay. Exposure to 100° C. for 30 minutes did not affect the potency of either toxin in either animal assay system.

Previous observations have shown that destruction of the disulfide bridges of biologic ST by treatment with reducing reagents such as 2-mercaptoethanol or dithiothreitol abolished its biologic activity, Staples, et al., supra. Exposure of synthetic ST to $5 \times 10^{-4}$ molar dithiothreitol for 60 minutes also abolished its secretory activity in the suckling mouse assay.

Immunological Relationship

The antigenicities of synthetic and biologic ST were similar when each was tested by enzyme linked immunosorbent assay (ELISA) using hyperimmune antisera to biologic ST. When those concentrations which yielded an optical density of 0.600 at 410 nanometers were compared, the antigenicity of synthetic ST was observed to be 70% that of biologic ST (FIG. 3), but the antigenicity of the toxins was identical when both were tested using hyperimmune antisera to synthetic ST. These results were substantially improved in later preparations as illustrated in Table 1, above, with the synthetic ST being about 3-fold better than biologic ST Ib in this same ELISA assay.

In order to evaluate the neutralizing effect of hyperimmune antisera to either synthetic or biologic ST on the secretory effect of the toxins in the suckling mouse assay, three mice for each datum point were given 100 microliters intraintestinally containing 2 mouse units (MU), twice the minimum effective dosage (see Materials and Methods Section IV A) of each toxin that had been incubated with the designated antiserum dilution for 3 hours at 37° C. (FIG. 4). The number of mouse units neutralized by 1 milliliter of anitserum was derived from multiplying the projected antiserum dilution required to neutralize (i.e., yield a gut:carcass ratio of at least 0.083) the secretory effect times the 10-fold dilution factor times the factor of 2 in order to adjust for the 2 mouse units used.

Hyperimmune antisera to each of the toxin preparations seroneutralized the secretory effect in the suckling mouse assay of synthetic and biologic ST to the same approximate degree: one milliliter of hyperimmune rabbit antiserum to biologic ST neutralized 160 MU of synthetic and 190 MU of biologic ST, while one milliliter of goat hyperimmune antiserum to synthetic ST neutralized 220 MU of synthetic and 240 MU of biologic ST.

Immunization of Rats

Immunization with the synthetic ST yielded serum antitoxin titers of 1:32 (four-fold greater than that of the controls) and mucosal IgA titers of 1:64 (five-fold greater than that of the controls). Fluid secretion was reduced by a significant degree that was comparable to an amount previously observed in rats immunized with semipure biologic ST [Klipstein, et al., Infect. Immun., 34: 637-639 (1981)] in rats challenged with either synthetic or biologic ST and with the viable ST-producing strain (Table 3), below.

TABLE 3

Results Of Challenge In Immunized Rats

| ST immunogen | Challenge [a] | | |
|---|---|---|---|
| | ST(B) toxin | ST(S) toxin | LT−/ST+ |
| Synthetic(S) | 54 ± 2 | 66 ± 2 | 55 ± 1 |
| Biologic (B)[b] | 83 ± 9 | ND[c] | 69 ± 2 |

[a] Mean ± standard error of the mean percent reduced secretion in immunized rats as compared to similarly challenged unimmunized animals.
[b] Data taken from Klipstein et al., Infect. Immun., 34:637-639 (1981).
[c] Not determined.

The above results show that immunization with a synthetically-produced ST toxin whose structure is based on that of human ST provides protection against challenge with ST-producing enterotoxigenic strains of E. Coli of human origin.

Further details of the studies discussed in this section (III A) may be found in Klipstein et al., *Infect. Immun.*, 39: 117–121 (1983), whose disclosures are incorporated herein by reference.

B. ST-LT Conjugates

The results discussed in this section relate to conjugate compositions and their properties obtained by cross-linking, under various conditions, synthetic ST (Section II) to either the LT holotoxin or its nontoxic component, the B subunit as a carrier which is responsible for binding of the toxin to specific receptors on the mucosal surface. The efficacy of a vaccine consisting of synthetic ST cross-linked to the B subunit for arousing specific serum and mucosal antitoxin responses to each of the component toxins is also demonstrated, thus providing strong protection in immunized rats against challenge with either toxin form or heterologous viable ETEC which produce either ST or LT.

Conjugation of ST to LT

Synthetic ST was conjugated to the LT holotoxin from an initial molar ratio of ST to LT of 100:1 using ratios of 1-ethyl-3-(3-dimethylaminopropyl) carbodiimide (EDAC) to total conjugate protein which varied between 0.5:1 to 40:1 (FIG. 5). Coupling of the maximum amount of ST to LT occurred at an EDAC to conjugate ratio of 1:1; however, an unacceptable degree of residual LT toxicity persisted at this ratio. Increasing the EDAC to conjugate protein ratio resulted in a progressive decrease in residual LT toxicity but this was accompanied by a corresponding reduction in the antigenicity of both toxins in the conjugate.

An EDAC to conjugate ratio of 20:1 resulted in a conjugate with an acceptable degree of reduced LT toxicity (0.3%), but the antigenicity of both component toxins was reduced to less than 25% at this ratio, indicating that this conjugate would be an ineffectual antigen. These observations led to substitution of the nontoxic B subunit for LT, thereby circumventing the problem of residual LT toxicity.

Conjugation of ST to B Subunit

Synthetic ST was conjugated to B subunit from an initial molar ratio of ST to B subunit of 100:1, using EDAC to conjugate protein ratios which varied between 0.5:1 and 40:1. The pattern of ST incorporation and the changes in antigenicity were similar to those noted for ST conjugation to LT except that the maximum amount of ST was coupled at an EDAC to conjugate ratio of 2:1. The toxicity of the conjugate obtained at this ratio was confined to that of the ST present; it was reduced to 0.3% of unattenuated toxin.

An EDAC to conjugate ratio of 2:1 was employed, therefore, in studies which utilized radiolabelled ST to determine the influence of the initial molar ratio of ST to B subunit on the amount of ST incorporated into the conjugate. Ten nanomoles of ST (5 nanomoles of cold, unlabelled ST plus 5 nanomoles of radiolabelled ST) were mixed with from 2 to 0.1 nanomoles of B subunit yielding initial ST to B subunit molar ratios of from 5:1 to 100:1 (FIG. 6). Increasing the initial ST to B subunit ratio resulted in progressively greater amounts of ST coupled to the B subunit. Although an initial ST:B subunit ratio of 25:1 yielded a final conjugate which contained more than 90% ST on a molar basis, the proportion of ST was only 25% on a weight basis; the latter value increased when larger initial molar ratios were used.

Antigenicity of the Conjugates

The effect of the EDAC concentration on the composition and antigenicity of the individual toxins in the final conjugates was assessed by conjugating a 50:1 molar ratio of ST to B subunit using EDAC to conjugate ratios which varied between 1:1 and 2:1 (FIG. 7). Maximum conjugation of ST occurred at an EDAC to conjugate ratio of 2:1; however ratios of greater than 1.5:1 resulted in a precipitous fall in ST antigenicity and a moderate decline in B subunit antigenicity. The maximum number of ST antigen units (derived by multiplying the percentage of toxin present times the percentage of its antigenicity) was achieved at an EDAC to conjugate ratio of 1.5:1.

An EDAC to conjugate ratio of 1.5:1 was used, therefore, in studies which determined the effect of the initial molar ratio of ST to B subunit on the composition and properties of the final conjugate. Increasing the initial molar ratio of ST to B subunit from 50:1 to 100:1 resulted in a progressively greater proportion of ST in the final conjugate (FIG. 8).

Since changes in the initial molar ratio were achieved by keeping the amount of ST (300 nanomoles) constant and reducing the amount of B subunit added (from 6 to 3 nanomoles), the ratio of EDAC to ST decreased while the ratio of EDAC to B subunit rose as initial molar ratios increased. This change accounted for the fact that the ST antigenicity rose slightly while that of the B subunit fell moderately. The net effect of these two factors (composition and antigenicity) was that increasing the initial molar ratio resulted in progressively greater amounts of ST antigen units, with a corresponding fall in B subunit antigen units, in the final conjugate.

Properties of The Vaccine Used For Immunization

It was previously shown that the B subunit is a weaker antigen than the LT holotoxin on a molar basis [Klipstein et al., *Infect. Immun.*, 31: 144–150 (1981)] and preliminary studies indicate that it is a weaker antigen in terms of antigen units than either the LT holotoxin or synthetic ST. This led to selection of a vaccine which contains more B subunit than ST antigenicity.

The antigen was produced by conjugating an initial ST to B subunit molar ratio of 50:1 using an EDAC to conjugate ratio of 1.5:1. The conjugate contained 36% (by weight) ST which had 85% retained antigenicity and 0.13% persistent toxicity, and 64% (by weight) B subunit which retained 89% of its antigenicity. When tested directly (i.e., in samples not adjusted to contain 100% of each toxin), the vaccine contained 37 ST and 59 B subunit antigen units per 100 micrograms and had a residual ST toxicity of 0.06%.

Results of immunization

Rats immunized with the above vaccine were given 1,000 micrograms primary immunization by the intraparenteral (i.p.) route followed by the two 3,000 microgram peroral (p.o.) boosts. Previous studies have shown that in rats immunized with LT by this approach, the degree of the antitoxin response and of protection correlate with the total p.o. dosage [Klipstein et al., *Infect. Immunol.*, 31: 144–150 (1981); Klipstein et al., *Infect. Immunol.*, 37: 1086–1092 (1982); Klipstein et al., *Infect. Immunol.*, 31: 252–260 (1981)]. This immunization schedule amounted to 2,200 ST and 3,450 B subunit antigen units.

Serum IgG antitoxin titers to ST were increased 4-fold and those to the B subunit were increased 5-fold over values in control, unimmunized rats. Mucosal secretory IgA antitoxin titers to both ST and B subunit were 7-fold greater in immunized rats than in controls. Immunized rats were significantly protected against challenge with LT or with either synthetic or biologic ST as well as against heterologous viable organisms which produce these toxins either singly or together as shown in Table 4, below.

TABLE 4

Results of Challenge in Rats Immunized With Cross-Linked ST-B Subunit Vaccine
Percent Reduced Secretion After Challenge With:[a]

| LT toxin | LT+/ST− | LT+/ST+ | ST(B) toxin[b] | ST(S) toxin[b] | LT−/ST+ |
|---|---|---|---|---|---|
| 94 ± 3 | 61 ± 2 | 68 ± 2 | 97 ± 3 | 78 ± 1 | 76 ± 2 |
| 0.5 ng[c] | 5 ng[c] | 5 ng[c] | 10[8,d] | 10[8,d] | 10[8,d] |

[a]Values are the mean ± standard error of the mean. Reduced secretion of more than 50% represents a significant (P less than 0.001) difference between immunized and unimmunized rats
[b]ST(B) signifies biologic ST, and ST(S) signifies synthetic ST.
[c]Amount of challenging toxin in nanograms (ng).
[d]Number of challenging organisms.

The above findings that synthetically produced, purified ST can be used to provide an effective, nontoxic antigen when it is cross-linked to the LT toxin B subunit surmounts a major obstacle in the development of a safe, practical vaccine that provides protection against ETEC strains which produce either the ST or LT form of toxin. Previous results showed that cross-linking a semipure preparation of biologic ST to LT yielded an antigen in which the ST acquired antigenicity as a function of coupling to the large molecular weight LT molecule, and in which, under the proper conjugation conditions, most of the antigenicity of the component toxins was maintained while their toxic properties were greatly reduced [Klipstein et al., *Infect. Immunol.*, 37: 550–557 (1981)].

Although that vaccine with biologic ST provided strong protection in immunized animals against challenge with ETEC strains which produce either toxin form, the heterogeneous composition of the semipure ST toxin component clearly precluded its adoption for human use. The complicated and tedious methodology involved in processing biologic ST to total purity renders large scale, much less commercial scale, production of this material difficult. The above findings indicate that synthetically-produced ST, which can readily be made in large quantities, provides an equally effective vaccine.

The reaction conditions for conjugates derived from synthetic ST which yield maximal incorporation of ST with the carrier together with optimal properties in terms of residual antigenicity and toxicity differ from those previously observed for conjugation of semipure biologic ST to LT. In both circumstances, (1) a critical amount of the conjugating reagent carbodiimide was necessary for coupling the maximum amount of ST to the carrier, (2) the proportion of ST present in the final conjugate was dependent on the initial molar ratio of ST mixed with LT, and (3) increasing the ratio of carbodiimide to either toxin in the conjugate resulted in a progressive decline both in the antigenicity and in toxicity of the cross-linked toxins. In the case of semipure biologic ST, conjugation conditions were identified which yielded a conjugate with maximal incorporation of ST to LT and at the same time retained most of the antigenicity but markedly reduced the toxicity of both of the cross-linked toxins.

Such did not occur, however, when synthetic ST was conjugated to LT. Maximum coupling of synthetic ST to LT occurred at a much lower carbodiimide to conjugate ratio under which conditions the residual LT toxicity of this conjugate was unacceptably high. A reduction in LT toxicity to acceptable levels was achieved only at carbodiimide to toxin ratios which severely compromised the antigenicity of both of the cross-linked toxins. These findings led to circumventing this problem by substituting the nontoxic B subunit for the LT holotoxin as the carrier.

The proportion of antigenicity (expressed as antigen units) for each of the component toxins present in the final conjugate derived by cross-linking synthetic ST to the B subunit can be altered by varying the conditions of the conjugation reactions. Thus, in the presence of the proper concentration of carbodiimide, a low initial molar ratio of ST to B subunit yielded a conjugate with predominantly ST antigenicity whereas a high initial molar ratio yielded one in which B subunit antigenicity is greatest.

Preliminary observations suggested that synthetic ST is a more effective antigen than the B subunit. This led to selection of a cross-linked antigen for evaluation by immunization in rats that contained roughly one-third ST and two-thirds B subunit antigenic activity. When given in large p.o. doses, that vaccine aroused at least a 4-fold serum and mucosal antitoxin response against both component toxins, thus providing significant protection against challenge by either the ST or LT toxins and heterologous viable bacteria which produce either toxin form.

Since all ETEC strains evoke diarrhea through the elaboration of the LT or ST toxins, either singly or together, the arousal of a sufficiently strong antitoxin response to each of these toxins provides uniformly effective protection against all ETEC strains irrespective of the somatic serotype, specific fimbrial antigen or type of toxin produced. Such was shown to be the case in the above study among rats immunized with the cross-linked ST-B subunit vaccine.

Immunization with LT given exclusively by the parenteral route aroused only a serum IgG antitoxin response which provided only transient protection in rats, whereas p.o. booster immunization yielded extended protection due to the arousal of mucosal secretory Ig antitoxin. [Klipstein et al., Infect. Immun., 37: 1086-1092 (1982) and Klipstein et al., Infect. Immun., 27: 81-86 (1982)].

Mucosal secretary IgA antitoxin titers to both ST and the B subunit in rats immunized perorally with the cross-linked vaccine in the above study exceeded those previously found necessary to provide extended protection in rats immunized with just LT. This makes it clear that the cross-linked vaccine should be given by the p.o. route. The above data are insufficient to determine whether primary immunization by the parenteral route is a prerequisite for subsequent effective p.o. immunization since such has been found to be the case for rats immuzined with LT [Klipstein et al., Infect. Immun., 31: 144-150 (1981); Klipstein et al., Infect. Immun., 37: 1086-1092 (1982); and Klipstein et al., Infect. Immun., 27: 81-86 (1980)] and rats and dogs immunized with cholera toxoid [Pierce et al., Infect. Immun., 21: 185-193 (1978); Pierce et al. J. Infect. Dis., 135: 888-896 (1977)].

Further details of the studies discussed in this section (III B) may be found in Klipstein et al., J. Infect. Dis., 147: 318-326 (1983), whose disclosures are incorporated herein by reference.

C. Synthetic ST Immunizations in Rats

Immunogenicity of ST and the B subunit

Figure 9:
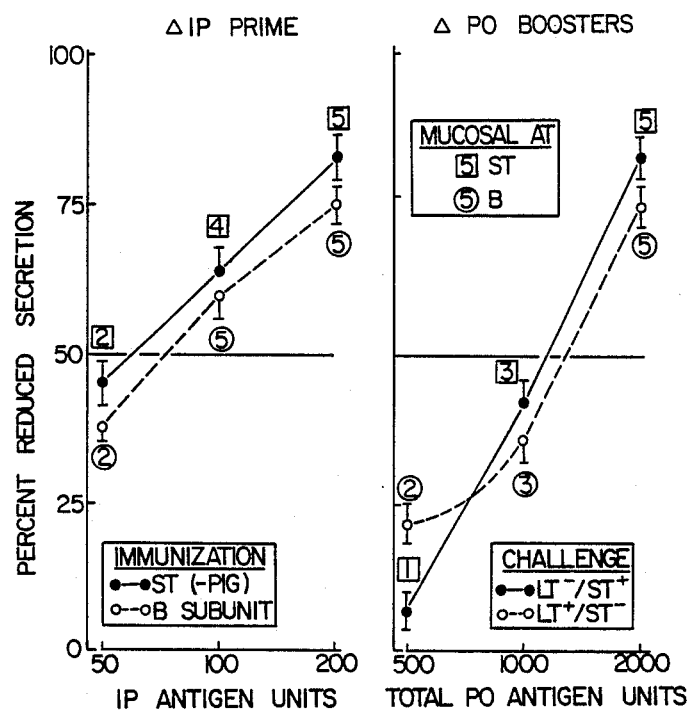
FIG. 9 illustrates protection attained in rats immunized with graded antigen unit dosages of either the B subunit or synthetic ST coupled to porcine immunoglobulin G (PIG). Rats given varying dosages for intraparenteral (i.p.) primary immunization (left panel) all received a total peroral (p.o.) booster dosage of 2,000 antigen units; those given variable p.o. boosters (right panel) all received i.p. primary immunization with 200 antigen units. Mucosal IgA antitoxin (mucosal AT) values in each panel are the increase in the reciprocal of the geometric mean titer in immunized rats over that of unimmunized controls. Numbers within squares designate the ST mucosal AT values while numbers within circles designate the mucosal AT values for the LT B subunit.

Rats were immunized with graded antigen unit dosages of either the B subunit or synthetic ST coupled to porcine immunoglobulin G (PIG; Materials and Methods section C) as is shown in FIG. 9. Those rats given variable dosages of the i.p. primary immunization all received two p.o. booster immunizations of 1000 antigen units each, and those given variable dosages for the p.o. boosters all received i.p. primary immunization with 200 antigen units. Rats immunized with ST were challenged with human LT−/ST+ strain Tx 452 and those immunized with the B subunit were challenged with human LT+/ST− strain PB 258.

Increasing the antigen unit dosages of either the i.p. primry immuniztion or the p.o. boosters of either antigen resulted in parallel increases in antitoxin titers and in the degree of protection against challenge with the respective organisms. Values for serum IgG antitoxin titers rose proportionately but were consistently one or two-fold less than mucosal IgA antitoxin titers.

Dosages of either antigen of 100 antigen units for i.p. primary immunization and a total of 2000 antigen units for the p.o. boosters (i.e., 2 boosters of 1000 antigen units each) were required to achieve at least 4-fold increases in mucosal IgA antitoxin titers and significant protection (i.e., greater than 50% reduced secretion) against challenge with the respective LT- pr ST-producing strain.

Protection against an LT+/ST+ strain

In order to determine the minimum antigen unit dosage of ST or B subunit necessary to achieve strong protection against a strain which produces both LT and ST, rats were immunized with each toxin separately, using an i.p. primary immunization of 200 antigen units followed by variable antigen unit dosages of the p.o. boosters, and were challenged both with the respective LT- or ST-producing strains and with human LT+/ST+ strain H 10407 (FIG. 10).

Strong protection against the LT+/ST+ strain was achieved only by a total p.o. booster dosage of 2000 antigen units. In each instance, the degree of protection against the LT+/ST+ strain was less than that for the strain which produced only the single homologous toxin.

Conjugation conditions for the vaccine

The preceding observations indicate that the optimal vaccine should contain equal antigenic proportions of each component toxin. It was shown in Section B, hereinabove, that when the ratio of carbodiimide to total conjugate protein is kept constant at 1.5:1 by weight, increasing the initial molar ratio of ST mixed with the B subunit yields a final conjugate with progressively more ST and less B subunit antigenicity.

When the initial molar ratio of ST to B subunit was varied between about 60:1 to about 75:1, it was found that a ratio of about 70:1 resulted in a conjugate which consisted of 50% of each toxin component by weight and contained 460 ST and 440 B subunit antigen units per milligram (FIG. 11). All subsequent conjugates discussed in this section were prepared in this manner. In five consecutive lots, mean antigen units per milligram were 474 for ST and 460 for the B subunit using the above ratios.

Properties of the vaccine (i) Immunogenicity.

In order to confirm the fact that the immunogenicity of the toxin components cross-linked in vaccine form is the same as that of the individual components, rats were immunized by i.p. primary immunization of 200 ST antigen units followed by graded p.o. booster dosages of ST given either in vaccine form or coupled to the immunologically nonspecific carrier PIG. The results are shown in FIG. 12. As seen in FIG. 12, the antitoxin response and degree of protection against the human LT−/ST+ strain were substantially identical in rats immunized with either form of ST conjugate.

(ii) Toxicity.

Assay of graded amounts (by protein content) of ST alone or of the vaccine in suckling mice showed that the vaccine contained 0.14 mouse units of ST activity per microgram, which represented 0.08% of the value of 175 mouse units per microgram of ST alone (FIG. 13). When graded amounts of either ST alone or the vaccine were tested in rat ligated ileal loops, the $ED_{50}$ of the vaccine, 2.6 micrograms, was 0.08% that of the value of the 2.0 nanograms for ST alone (FIG. 14). The B subunit alone had an $ED_{50}$ of 95 nanograms in ligated ileal loops which was 0.2% of the value of 0.19 nanograms for the LT holotoxin. Whether this secretory activity was due to the B subunit itself or a manifestation of slight, otherwise undetected contamination with LT is uncertain.

In order to determine whether the B subunit component was contributing to the residual secretory activity of the vaccine in the rat ligated ileal loop assay, graded dosages of vaccine were tested after heat inactivation of the B subunit (or its LT contaminant) by exposure to 65° C. for 1 hour. The secretory response to heated and unheated vaccine was the same, excluding a role for the B subunit in this response. These observations indicate that the toxicity of a dosage of vaccine containing 1000 antigen units of each component toxin would consist of the equivalent of 1.7 micrograms of unattenuated ST.

(iii) Protection against human and porcine strains.

Rats were immunized by primary i.p. immunization with vaccine containing 200 antigen units of each component toxin and two p.o. boosts, each of which had 1000 antigen units of each toxin component. This raised serum IgG antitoxin titers to both toxin components by 3-fold and mucosal IgA antitoxin titers by 5-fold to ST and by 6-fold to the B subunit. The immunized rats were significantly protected (P less than 0.001) against challenge with viable human or porcine strains which produce LT or ST toxin, either singly or together, as is shown in Table 5, below.

TABLE 5

Results of Challenge In Rats Immunized With the Cross-Linked Vaccine

| Source | Toxicity | Strain | Serotype | % Reduced Secretion |
|---|---|---|---|---|
| Human | $LT^+/ST^-$ | PB 257 | O15:H$^-$ | 74 ± 1 |
| Porcine | $LT^+/ST^-$ | P 263 | O8:H19 | 72 ± 3 |
| Human | $LT^+/ST^+$ | H 10407 | O78:H11 | 61 ± 1 |
| Porcine | $LT^+/ST^+$ | P 1362 | O149:H?[b] | 73 ± 2 |
| Human | $LT^-/ST^+$ | Tx 452 | O78:H12 | 79 ± 2 |
| Porcine | $LT^-/ST^+$ | P 987 | O9:H$^-$ | 81 ± 2 |

[a]Mean ± standard error of the mean percent reduced secretion in immunized rats as compared to similarly challenged unimmunized animals. Values of more than 50% represent a significant (P less than 0.001) difference between the two groups.
[b]The complete identification of this serotype is uncertain.

Primary parenteral immunization was given to an additional group of rats by the subcutaneous (s.c.) route using alum as the adjuvant, prepared as described previously for LT immunization [Klipstein et al., *Infect. Immun.*, 37: 1086–1092 (1982)]. Since this approach has been found to require twice the dosage used for the i.p. route for effective LT primary immunization, the s.c. dosage of the vaccine given was doubled to 400 antigen units; the p.o. dosage was unchanged at 1000 antigen units. This raised at least 5-fold mucosal IgA antitoxin titers to both toxin components and provided significant protection against challenge, with secretion reduced by 77±3% against the human $LT^+/ST^-$ strain and by 71±2% against the human $LT^-/ST^+$ strain.

The above results indicate that, when evaluated in the manner of Klipstein et al., *Infect. Immun.*, 31: 144–150 (1981), the antigenicity of synthetically-produced ST is substantially the same as that of the B subunit. Essential to this comparison was the expression of dosage of conjugated toxin in terms of antigen units rather than on a weight basis.

This information led to modifying the conjugation conditions used previously to cross-link synthetic ST to the B subunit, Section B above, in order to produce a vaccine that contains equal antigenic proportion of ST and B subunit. The antigenicity of the synthetic ST component in vaccine form was shown to be identical to that of this toxin when given coupled to a nonspecific immunoglobulin carrier. Immunization of rats with vaccine, given at those antigen unit dosages found effective for each of the component toxins given seprately, raised a strong antitoxin response to each of the component toxins and provided significant protection against viable ETEC strains that produce LT or ST, either singly or together. Observations derived from immunizations with each toxin component given separately indicated that the protection afforded by the vacine against the $LT^+/ST^+$ strain was attributable to both toxin components.

Frantz and Robertson have reported that antisera to porcine ST reacts with ST from ETEC strains of porcine, bovine, and human origin [*Infect. Immun.*, 33: 193–198 (1981)]. The above results indicate that cross-protection can be achieved by immunization with either toxin irrespective of its source. Thus, immunization with the cross-linked vaccine containing a B subunit derived from porcine LT and synthetic ST based on the structure of human ST provided equally strong protection against human and porcine LT- and ST-producing strains.

Immunization was given in the above study by means of parenteral primary immunization followed by p.o. boosters because it was previously found in the rat animal model that, (1) parenteral priming is a prerequisite for strongly effective p.o. booster immunization, (2) only p.o. immunization raises mucosal IgA antitoxin titers, and (3) extended protection is achieved only when a sufficient p.o. dosage is given that raises mucosal IgA titers by at least 4-fold. Immunization with the cross-linked vaccine by this approach yielded increases of this magnitude in mucosal IgA antitoxin titers to both of the component toxins. The subcutaneous (s.c.) route and alum adjuvant were shown to be equally effective for immunization.

Further details of the studies discussed in this section (III C) may be found in Klipstein et al., *Infect. Immun.*, 40: 924–929 (1983), whose disclosures are incorporated herein by reference.

D. Synthetic ST Immunization in Rats and Rabbits

The above discussed results (Section III C) were obtained in the rat using i.p. immunizations followed by p.o. boosters. The results discussed below were obtained in both rats and rabbits using the peroral route of administration for both the primary and booster immunizations.

The results below indicate that the peroral route of immunization is equally as effective as is the i.p. route. In addition, it is noted that the vaccine did not cause diarrhea in any animal when given by the p.o. route, nor did it cause fluid secretion when instilled into rabbit ligated ileal loops.

Rat Studies (i) i.p./p.o. immunization.

Rats received primary immunization with 200 AU (antigen units; see Materials and Methods Section IV D) of vaccine given i.p. with Freund's complete adjuvant (FCA) followed by two p.o. boosters of 1000 AU each. This dosage was selected because it has been shown (Section C, supra) to be the minimal amount necessary to provide significant (P less than 0.001) protection against challenge with viable strains which produce either toxin form. This immunization raised 4-fold increases in serum, and at least 6-fold increases in mucosal, antitoxin titers to each toxin component of the vaccine (Table 6, below) and it provided protection index (PI) values of 3.4 against challenge with LT and 4.0 against challenge with ST (FIG. 15).

TABLE 6

Antitoxin Response And Degree Of Protection In Immunized Rats

| Route of Immunization | Antitoxin to B[a] | | Antitoxin to ST | | PI | |
|---|---|---|---|---|---|---|
| | Serum | Mucosal | Serum | Mucosal | vs LT | vs ST |
| i.p./p.o. | 4 | 6 | 4 | 7 | 3.4 | 4.0 |

[a]Values are the fold increase in the reciprocal of the geometric mean titer in immunized over control animals.
[b]PI = protection index.

(ii) Other Immunization Approaches

In order to determine the effectiveness of other parenteral routes, adjuvants and p.o. delivery systems, additional groups of four rats each were given primary immunization with 400 AU of vaccine by the subcutaneous (s.c.) route using alum as the adjuvant, prepared as described previously for LT [Klipstein et al., *Infect. Immun.*, 37: 1086-1092 (1982)]; this was followed by two p.o. boosters, each of 1000 AU, given either 2 hours after p.o. cimetidine or in the form of pH-dependent microspheres without pretreatment with cimetidine. When challenged with LT−/ST+ strain Tx 452, each of these alternative approaches to immunization yielded the same significant (P less than 0.001) degree of reduced secretion as that achieved by using the i.p. route with FCA followed by p.o. boosters given after cimetidine. These results are shown in Table 7, below.

TABLE 7

Effectiveness of Alternative Routes, Adjuvants And Delivery Systems Of The Vaccine in Rats

| Primary Route/Adjuvant | Booster Route/Protection | Protection vs LT−/ST+[a] |
|---|---|---|
| i.p./FCA | p.o./cimetidine | 79 ± 2 |
| s.c./alum | p.o./cimetidine | 71 ± 2 |
| s.c./alum | p.o./microspheres | 67 ± 2 |

[a]Mean ± SEM percent reduced secretion in immunized animals as compared to similarly challenged unimmunized controls. Values of more than 50% represent a significant (P less than 0.001) difference between the two groups.

Rabbit Studies (i) i.m./p.o. immunization

Four rabbits received primary immunization with 500 AU of vaccine given intramuscularly (i.m.) with FCA, followed by two p.o. boosters of 1000 AU each. This raised more than 5-fold increases in serum, and 4-fold increases in mucosal antitoxin titers to each component of the vaccine. PI values were more than 9 against challenge with either LT or ST. These data are shown in FIG. 16, and in Table 8, below.

TABLE 8

Antitoxin Response And Degree Of Protection In Immunized Rabbits

| Route of Immunization | Antitoxin to B[a] | | Antitoxin to ST | | PI | |
|---|---|---|---|---|---|---|
| | Serum | Mucosal | Serum | Mucosal | vs LT | vs ST |
| i.m.[c]/p.o. | 5 | 4 | 6 | 4 | 9.3 | 10.0 |
| p.o./p.o. | 3 | 5 | 2 | 4 | 8.6 | 8.1 |

[a]Values are the fold increase in the reciprocal of the geometric mean titer in immunized over control animals.
[b]PI = protection index.
[c]i.m. = intramuscular.

(ii) p.o./p.o. immunization

Four rabbits received immunization with 1000 AU of vaccine given p.o. on three occasions. This raised 4-fold increases in mucosal, but not in serum, antitoxin titers and provided strong protection, with PI values of more than 8 against challenge with either toxin form. These data are also shown in Table 8, above.

Toxicity of the Vaccine

Previous studies (Section III C) have shown that the toxicity of the ST component of the vaccine is reduced to 0.15% of unattenuated toxin. A dosage of 1000 AU of vaccine would thus contain the equivalent of 1.7 micrograms of unattenuated ST (0.15% times the 50% ST component of 2.2 milligrams). The toxicity of this dosage of the vaccine and of larger amounts of unattenuated ST was evaluated in unimmunized animals. (i) The p.o. administration of 1000 AU of vaccine to eight rabbits and 20 rats produced no adverse effects such as diarrhea, and the instillation of this dosage of vaccine into four ligated ileal loops in two rabbits failed to evoke any fluid response. (ii) The p.o. administration of 250 micrograms of unattenuated ST to two rabbits and rats did not cause diarrhea. The instillation of 25 micrograms of unattenuated ST did not cause any fluid secretion in ligated ileal loops of four rabbits; a dosage of 50 micrograms was required to yield a positive fluid:length ratio of 1.1±0.3 (mean±SEM).

The results of the above study establish the effectiveness of immunization with a vaccine made using a synthetic ST of this invention in an experimental animal model, rabbits, in addition to rats. Protection in both animal models was demonstrated by use of the ligated ileal loop technique. The applicability of this technique to protection under conditions in which the entire intact intestine is acutely colonized by enterotoxigenic strains of *E. coli* has been confirmed in rats immunized with LT [Klipstein et al., *Infect. Immun.*, 28: 163-170 (1980)].

The same p.o. dosage of vaccine (1000 AU), given after primary parenteral immunization, resulted in a considerably stronger degree of protection, as manifested by PI values, in rabbits than in rats. This difference may in part be attributable to the longer interval between immunizations used for rabbits (14 days versus four days in rats), and perhaps to differences in sensitivity to toxin challenge. It also probably indicates that rabbits are more responsive to immunization with the vaccine than rats. This dosage used was the minimum found required to achieve significant protection against viable enterotoxigenic strains in rats (Section C, supra).

The fact that this dosage was also effective in providing strong protection in a larger experimental animal points to utility in animal husbandry and humans. This is also suggested by the observations of Svennerholm et al. who found that a p.o. immunization dosage of 500 micrograms of cholera toxin B subunit is sufficient to arouse a significant intestinal IgA antitoxin response in human volunteers [*Lancet*, 1: 305–308 (1982)].

The results of the present study indicate that exclusive p.o. immunization of rabbits with the synthetic ST-B vaccine achieved the same strong degree of protection as that achieved by p.o. booster immunizations following parenteral primary immunization.

Further details of the studies discussed in this section (III D) may be found in Klipstein et al., *Infect. Immun.*, 40: 888–893 (1983), whose disclosures are incorporated herein by reference.

E. Cross Reactivity With Klebsiella ST Enterotoxin

Diarrheal epidemics among nursery children have implicated *Klebsiella pneumoniae* as the causing agent. The enterotoxigenicty of several Klebsiella strains has been established by assay of cell-free culture filtrates in rabbit ileal loops, in Y1 adrenal cell or Chinese hampster ovary tissue culture assays for the heat-labile toxin (LT) and in the suckling mouse assay, supra, for the heat-stable toxin (ST). The Klebsiella LT and ST enterotoxins identified in these assays have not been purified, and their relationship to similar toxins produced *E. coli* is unknown.

Klipstein et al., *J. Infect. Dis.*, 42: 838–841 (1983) report upon the purification of Klebsiella ST toxin to apparent homogeneity, and upon its immunological relationship to *E. coli* ST. The disclosures of that publication are incorporated herein by reference.

Natural enterotoxins were obtained from Klebsiella strains TS 9 (serotype 19), were isolated from the small bowel of a Puerto Rican patient having tropical sprue whose culture filtrate had previously been shown to evoke a positive response in a suckling mouse assay, and were also obtained from the *E. coli* strain 18 D (042:H47), an ST-only producing strain isolated from the stool of a child with acute diarrea. The toxins were purified by the methods described by Staples et al., *J. Biol. Chem.*, 255: 4716–4721 (1980) for the purification of human ST from *E. coli* strain 18 D.

After three consecutive chromagraphic separation procedures used for purification, the resulting toxin had been purified by a factor of 148 over the originally obtained material, and thin layer chromotagraphy of the purified material showed a single band. The purified Klebsiella ST was equally potent as *E. coli* ST in the suckling mouse assay, within the limits of experimental variation for that assay. In addition, treatment of the Klebsiella ST with $5 \times 10^{-4}$ molar dithiothreitol for 60 minutes abolished its secretory activity in the suckling mouse assay, as occurs with *E. coli* ST. Using a double sandwich ELISA as discussed in Section III A above, IV A hereinafter and in Klipstein et al., *Infect. Immun.* 39: 117–121 (1983), the antigenicity of the Klebsiella ST was found to be 69 percent that of *E. coli* ST.

Because of the functional similarities between *E. coli* ST and Klebsiella ST, it was of interest to determine whether a vaccine effective against *E. coli* ST would also offer protection against Klebsiella ST. The vaccine containing a conjugate of the *E. coli* LT B subunit and synthetic ST that is described in Section III D hereinabove was utilized for these immunizations.

Sprague-Dawley rats weighing between 150 and 175 grams were given primary immunization with the vaccine containing 200 antigen units of both ST and LT B subunit by the intraperitoneal route with complete Freund's adjuvant. This was followed at four day intervals by two per oral booster immunizations of 1000 antigen units each, given two hours after the per oral administration of cimedeine (TAGAMET ®) available from Smith Kline and French Laboratories, Carolina, Puerto Rica) at a dosage of 50 milligrams per kilogram of body weight in order ablate gastric secretion.

Unimmunized control rats and immunized rats four to six days after the final booster immunization were challenged by the instillation of graded doses of the ST toxin in ligated ileal loops for 18 hours as described in Section III D hereinabove, Section IV D and in Klipstein et al., *Infect. Immun.*, 49: 888–893 (1983). Each datum point for fluid secretion (presented as the means ± standard error of the mean) was derived from challenge in four or five immunized and five control rats. The protection index (PI) was determined by dividing that dosage of toxin in immunized animals which yielded same secretion as the 50% effective dose ($ED_{50}$) in unimmunized animals by the value for unimmunized animals.

The results of this determination are shown graphically in FIG. 18 wherein the data for the challenge with *E. coli* ST in immunized rats is that shown in the lower portion of the graphs of FIG. 15, while the data relating to challenge with Klebsiella ST are those generated in this study. As can be seen the protection index (PI) against challenge with *E. coli* ST was 4.0 while that against Klebsiella ST was 2.6. The results shown in the graph of FIG. 18 illustrate that a vaccine containing a conjugated synthetic ST of this invention also offers some protection against the ST enterotoxin produced by *Klebsiella pneumoniae*.

IV. MATERIALS AND METHODS FOR MONOMERIC ST

Section A

Enterotoxin Production

The complete procedure for synthesis and purification of the synthetic ST used herein and in each following lettered section is described in detail in Section II.

Biologic ST was purified to homogeneity from culture filtrates of strain 18D by a modification [Klipstein et al. *Infect. Immun.*, 37: 550–557 (1982)] of the methods described by Staples et al., supra. The amounts of toxins were based on their protein concentration determined by the method of Lowry et al., *J. Biol. Chem.*, 193: 265–275 (1951).

Assay of Secretory Potency

The ability of graded dosages of the toxins to cause secretion was tested in the suckling mouse and rat ligated ileal loop assays using published methods [Giannella, *Infect. Immun.*, 14: 95–99 (1976) and Klipstein et al., *Infect. Immun.*, 34: 637–639 (1981)]. One mouse unit (MU) in the suckling mouse assay is defined as that amount of toxin which yields an intestinal (gut):carcass weight ratio of at least 0.083.

Production of Hyperimmune Antiserum

Hyperimmune antiserum was raised in goats and rabbits to biologic ST as described previously [Klipstein et al., *Infect. Immun.*, 37: 550–557 (1982)]. Synthetic ST was coupled to porcine immunoglobulin G (PIG) by mixing ST to PIG at a molar ratio of 100:1, using a ratio by weight of 1-ethyl-3-(3-dimethylaminopropyl)carbodiimide to total conjugate protein of 2:1, in 0.1 molar phosphate buffer, pH 7.0, for 18 hours, at 4° C. This conjugate contained 47% ST by weight and 98% ST by moles. The conjugated ST retained 73% of its antigenicity, determined by enzyme-linked immunosorbent assay (ELISA) using hyperimmune goat and rabbit antisera to biologic ST in a previously described double sandwich technique [Klipstein et al., *Infect. Immun.*, 37: 550–557 (1982)]. The conjugate thus contained 343 antigen units (derived by multiplying the percentage of ST present by weight times the percentage of its antigenicity) per milligram of protein. Animals were immunized intramuscularly with Freund's complete adjuvant (FCA) for the primary immunization and Freund's incomplete adjuvant for the booster immunization given one month later. Goats received 1,100 followed by 2,300 ST antigen units, and rabbits received 300 followed by 500 St antigen units.

Immunization and Challenge of Rats

Weanling Sprague-Dawley rats were immunized with the synthetic ST-PIG conjugate by means of an intraperitoneal primary immunization of 350 ST antigen units given with Freund's complete adjuvant followed at 4 day intervals by two peroral booster immunizations containing 700 ST antigen units each, which were given 2 hours after the peroral administration of cimetidine in order to ablate gastric acidity. They were challenged 5 days after the final boost by the installation for 18 hours into a single ligated ileal loop of concentrations which evoke maximum secretion in unimmunized rats: 5 nanograms of either synthetic or biologic ST and 0.1 milliliter of a broth culture containing $10^9$ viable organisms per milliliter of ST-producing human *E. coli* strain Tx 452 (078:H12). Five unimmunized and three immunized rats were challenged with each test material. Values are expressed as the means ± standard error of the mean percent reduced secretion in immunized rats are compared to that in unimmunized controls; in each instance more than 50% reduced secretion represents a significant difference (P less than 0.001) between the two groups as determined by Student's t-test for two independent means.

Antitoxin response to immunization

At the time of challenge, serum and mucosal washings were processed as described previously [Klipstein et al., *Infect. Immun.*, 37: 1086–1092 (1982)] and assayed by a double sandwich ELISA in which goat hyperimmune antiserum to synthetic ST was used for the solid phase and synthetic ST was employed as the antigen. Klipstein et al., *Infect. Immun.*, 37: 1086–1092 (1982) found that rats similarly immunized with LT, only serum antitoxin of the immunoglobulin G (IgG) and mucosal antitoxin of the immunoglobulin A (IgA) class can be detected; therefore, antitoxin to synthetic ST was evaluated for only these two immunoglobulin classes using rabbit anti-rat IgG together with goat anti-rabbit antiserum conjugated to alkaline phosphatase for serum samples and goat anti-rat secretory IgA together with rabbit anti-goat antiserum conjugated to alkaline phosphatase (Miles Research Laboratories, Elkhart, Ind.) for mucosal samples. Values reported are for the geometric mean titer in 9 immunized and 5 unimmunized control rats.

Section B

Enterotoxin preparations

Purified LT holotoxin was prepared by the methods described by Clements and Finkelstein, *Infect. Immun.*, 24: 760–769 (1979) from *E. coli* strain 711 (F1LT), a transformed K-12 derivative bearing LT gene(s) of the Ent plasmid from porcine strain P307. The B subunit was separated from the LT holotoxin by the chromatogrphic techniques described by Clements et al., *Infect. Immun.*, 29: 91–97 (1980). The homogeneity of the LT toxin and its B subunit was confirmed by polyacrylamide gel electrophoresis as described by Clements and Finkelstein, supra.

Biologic ST, obtained by growth of human *E. coli* strain 18D (042:H47), was purified by the methods described by Staples et al, supra, with the modification that final purification to homogeneity was achieved by elution from thin layer chromatography as described by Klipstein et al., *Infect. Immun.*, 37: 550–557 (1982). Synthetic ST, consisting of the same sequence of 18 amino acids described by Chan et al., supra, for pure ST obtained by growth of strain 18D, was prpeared using a Beckman model 990 B peptide synthesizer (Beckman Instruments Co., Irvine, CA) by methods reported in Section II. The synthetic toxin was shown to be substantially identical to that obtained by culture techniques (biologic ST) in terms of secretory potency in the suckling mouse assay and antigenicity as determined by enzyme-linked immunoadsorbent assay (ELISA) and by seroneutralization of secretory activity in the suckling mouse assay by hyperimmune antiserum to either the synthetic or biologic toxin in Section III, hereinbefore.

The amount of toxins used, stated as weight, was based on protein concentrations determined by the method of Lowry et al., supra. Molar equivalents were derived from published values of a molecular weight of 91,450 daltons for LT by Clements et al., *Infect. Immun.*, 29: 91–97 (1980), 57,400 for the polymeric 5 B subunits by Gill et al., *Infect. Immun.*, 33: 677–682 (1981), and 1,972 daltons for ST by Staples, et al., supra.

Radioiodination of ST

Synthetic ST was radioiodinated by the chloramine-T method of Hunter, *Proc. oc. Exp. Biol. Med.*, 133: 989–992 (1970) using procedures described previously for pure biologic ST by Klipstein et al., *Infect Immun.*, 37: 550–557 (1982). The radiolabelled toxin contained $3 \times 10^5$ counts per minute and 71 mouse units per microgram (versus 175 mouse units per microgram for unlabelled toxin) as determined by the suckling mouse assay in which one mouse unit is defined as that amount which yields an intestinal weight:carcass weight ratio of at least 0.083.

Conjugation

ST was conjugated either to LT or to the B subunit by adding 1-ethyl-3-(3-dimethylaminopropyl)carbodiimide (EDAC) (Sigma Chemical Co., St. Louis, MO) to mixtures of the toxins in 0.1 molar phosphate buffer at a pH 7.0 for 18 hours at 4° C. The conjugate was then exhaustively dialysed against water for 48 hours at 4° C. using a 12,000 molecular weight cut off dialysis bag which retained all of the LT (or B subunit) and conjugated ST but not unconjugated ST or EDAC. Repeated determinations showed that dialysis against water of either LT or the B subunit alone resulted in a 10% loss due to precipitation. Therefore, the amount of ST conjugated was based on the incremental increase in Lowry protein present in the dialysand that was in excess of 90% of the amount of either LT or B subunit initially added. The amount of radioiodinated ST conjugated was ascertained by comparing the radioactivity of the final conjugates to that initially added using an autogamma counter sold under the trademark PRIAS ® PGD by Packard Instrument Co., Downers Grove, IL.

Properties of the conjugate

Unless otherwise specified, the concentration of each conjugate was adjusted to represent 100% of the specific toxin tested in studies which compared the properties of conjugated toxins to those of unattenuated toxin. LT toxicity was compared by assaying serial 2-fold dilutions of LT alone and in conjugated form in the Y1 adrenal cell assay of Sack et al., *Infect. Immun.*, 11: 334–336 (1975). ST toxicity was compared by establishing the minimal effective dosage of serial dilutions of synthetic ST alone or in conjugated form in the suckling mouse assay of Klipstein et al., *Infect. Immun.*, 37: 550–557 (1982).

Antigenicity was determined by means of ELISA. Monospecific goat hyperimmune antiserum to either LT or the B subunit of cholera [Clements et al., *Infect. Immun.*, 29: 91–97 (1980)] were used with rabbit anti-goat antiserum conjugated to alkaline phosphatase (Miles Research Laboratories, Elkhart, Ind.). For ST, hyperimmune antiserum to pure biologic ST raised in goats and rabbits as described previously [Klipstein et al., *Infect. Immun.*, 37: 550–557(1982)] as used in a double sandwich technique along with rabbit anti-goat antiserum conjugated to alkaline phosphatase; values for the conjugates were compared to that of synthetic ST in this assay. Starting at 10 micrograms, serial 2-fold dilutions were made of the conjugates and appropriate toxin. That concentration at which these preparations yielded an absorbance of 0.600 at 410 nanometers was used to compare the antigenicity of the toxin in conjugated and unattenuated form.

Immunization procedures

Rats were given primary immunization intraperitoneally (i.p.) using Freund's complete adjuvant followed by two peroral (p.o.) boosters at 4 day intervals. Peroral immunization was given via an intragastric tube 2 hours after the p.o. administration of cimetidine (sold under the trademark TAGAMET® by Smith, Kline and French Laboratories, Carolina, Puerto Rico), at a dosage of 50 milligrams/kilogram of body weight in order to ablate gastric secretion.

Challenge procedures

Rats were challenged 1 week after the final boost by the instillation of test material into a single 10-centimeter ligated loop of distal ileum for 18 hours as described previously [Klipstein et al., *Infect. Immun.*, 31: 144–150 (1981) and 32: 1100–1104 (1981)]. Previous studies have established a correlation between significant protection in this assay system and that achieved in immunized rats challenged by intestinal contamination of the intact intestine [Klipstein et al., *Infect. Immun.*, 28: 163–170 (1980)]. Challenge dosages were those which evoked maximum secretion in unimmunized animals: 0.5 nanograms LT, 5 nanograms of either synthetic or biologic ST, and 0.1 milliliter of broth cultures containing $10^9$ viable organisms per milliliter of LT+/ST− strain PB-258 (015:H−), LT+/ST+ strain H-10407 (078:H11), and LT−/ST+ strain Tx 452 (078:H12). Each datum point was determined in from 3 to 5 immunized rats and the values reported are the mean ± standard error of the mean (SEM) degree of reduced secretion in immunized rats as compared with the value in 5 similarly challenged unimmunized rats. Reduced secretion of 50% was significant for each challenge material at a P value of less than 0.001 as determined by Student's t-test for two independent means.

Antitoxin response

Serum and musosal antitoxin titers to the synthetic ST and B subunit components of the vaccine were determined in the serum and mucosal washings of immunized rats by ELISA using techniques described in previous studies which showed that the antitoxin response of rats immunized with LT by the parenteral/peroral approach is confined to that associated with serum IgG and musocal IgA [Klipstein et al., *Infect. Immun.*, 37: 1086–1092 (1982)]. For this reason, only antitoxins of these immunoglobulin classes were assayed in the present study. For antitoxin to the B subunit, the B subunit was used as the solid phase; for antitoxin to synthetic ST, hyperimmune antiserum to synthetic ST developed in a goat was used as the solid phase and synthetic ST was used as the antigen in a double sandwich technique. For serum samples, rabbit anti-rat IgG and goat anti-rabbit antiserum conjugated to alkaline phosphatase were added; for muscosal washings, goat anti-rat secretory IgA and rabbit anti-goat antiserum conjugated to alkaline phosphatase (Miles Research Laboratories, Elkhart, Inc.) were used. The values reported are for the increase in the reciprocal of the geometric mean titer in samples from 5 immunized over those in 5 unimmunized control rats. Antitoxin titers in control animals were 1:2 against either ST or B subunit in all samples except that the serum titer against ST was 1:4.

Section C

Preparation of the vaccine

Purified LT holotoxin was prepared from *E. coli* strain 711 (FILT), a transformed K-12 derivative bearing LT gene(s) of the Ent plasmid from porcine strain P307, and separated into its subunits by chromotographic techniques as discussed above, in Section B. The homogeneity of the LT holotoxin and its B subunit was confirmed by polyacrylamide gel electrophoresis as also discussed in Section B. Synthetic ST, consisting of the same primary structure of 18 amino acids described by Chan et al., supra, for pure ST obtained by purification of cultures of strain 18D, was prepared as per Section II, supra.

The amount of toxins used was based on their protein concentrations determined by the method of Lowry et al., supra; their molar equivalents were derived from published values of a molecular weight of 57,400 daltons for the polymeric form of five B subunits and 1,972 daltons for ST, as discussed in Section B, above.

ST was conjugated to the B subunit by adding 1-ethyl-3-(3-dimethylaminopropyl) carbodiimide (Sigma Chemical Co., St. Louis, MO) at a ratio by weight of 1.5:1 to the total protein of mixtures of varying molar ratios of the toxins in 0.1M phosphate buffer at pH 7.0 for 18 hours at 4° C.; the conjugate was then exhaustively dialyzed against water and processed thereafter as described previously in Section B, above.

Properties of the vaccine

The antigenicity of the component toxins in the vaccine was determined by means of enzyme-linked immunosorbent assay (ELISA) as described above in Section B. For the B subunit, monospecific goat hyperimmune antiserum to the B subunit of human LT was used with rabbit anti-goat antiserum conjugated to alkaline phosphatase (Miles Research Laboratories, Elkhart, Ind.). For ST, hyperimmune antiserum to synthetic ST raised in goats and rabbits (Section IV, A, above) was used in a double sandwich technique along with rabbit anti-goat antiserum conjugated to alkaline phosphatase. Starting at 10 micrograms, serial 2-fold dilutions were made of the conjugates and the appropriate toxin. The concentrations at which the conjugate and toxin yielded an adsorbance of 0.600 at 410 nanometers were compared and the value for the conjugate was expressed as a percentage of that of the unattenuated toxin. The percentage antigenicity times 1000 yielded the value for antigen units per milligram in the vaccine.

Residual toxicity in the vaccine was determined by comparing the values for ST and the vaccine of (i) the minimal effective dosage in the suckling mouse assay in which one mouse unit is defined as that amount which yields an intestinal weight/carcass weight ratio of at least 0.083, and (ii) the $ED_{50}$ (that dosage which yields one-half maximum secretion) in ligated ileal loops of unimmunized rats.

ST conjugation

In those instances where rats were immunized with synthetic ST alone, the toxin was coupled to porcine immunoglobulin G (PIG) at a molar ratio of toxin to PIG of 100:1 and a carbodiimide to total conjugate protein ratio of 1:1 by weight. This conjugate contained 46% ST by weight and had 470 ST antigen units per milligram.

Immunization procedures

Unless specified otherwise, rats were given primary immunization intraperitoneally (i.p.) using Freund's complete adjuvant following by two peroral (p.o.) boosters at 4 day intervals. Peroral immunization was given via an intragastric tube 2 hours after the p.o. administration of cimetidine (sold under the trademark TAGAMET® by Smith, Kline and French Laboratories, Carolina, Puerto Rico), at a dosage of 50 milligrams/kilogram body weight in order to ablate gastric secretion.

Challenge procedures

Rats were challenged 4 to 6 days after the final boost by the instillation into a single 10-centimeter ligated loop of distal ileum for 18 hours of 0.1 milliliters of broth cultures containing $10^9$ variable organisms per milliliter. Each datum point was determined in 3 to 5 immunized rats and the values reported are for the mean ± standard error of the mean of the degree of reduced secretion in immunized rats as compared with 5 unimmunized rats challenged with the same organisms. Reduced secretion of more than 50% is referred to as strong protection since it was significant in each instance at a P value of less than 0.001 as determined by Student's t-test for two independent means.

Antitoxin response

Serum and mucosal antitoxin titers were determined by ELISA by techniques described in Section B, above. For antitoxin to the B subunit, the B subunit was used as the solid phase; for antitoxin to ST, goat hyperimmune antiserum to synthetic ST was used as the solid phase and synthetic ST was used as the antigen in a double sandwich technique. Since previous studies have shown that immunization with LT given by the i.p./p.o. approach arouses only serum IgG and mucosal IgA antitoxin titers [Klipstein et al., *Infect. Immun.*, 37: 1086–1092 (1982)], only antitoxin of these immunoglobulin classes was evaluated. For serum samples, rabbit anti-rat IgG and goat anti-rabbit antiserum conjugated to alkaline phosphatase were added; for mucosal washings, goat anti-rat secretory IgA and rabbit anti-goat antiserum conjugated to alkaline phosphatase (Miles Research Laboratories, Elkhart, Ind.) were used. The values reported are for the increase in the reciprocal of the geometric mean titer in 5 immunized over that in 5 unimmunized control rats.

Section D

Preparation of the vaccine

Purified LT holotoxin was prepared from *E. coli* strain 711 (F1LT), a transformed K-12 derivative bearing LT gene(s) of the Ent plasmid from porcine strain P307, and separated into its subunits by chromatographic techniques as discussed in Section B, above. The homogeneity of the LT holotoxin and its B subunit was also confirmed by polyacrylamide gel electrophoresis as discussed in Section B. Synthetic ST, consisting of the same primary structure of 18 amino acids as the polypeptide described by Chan et al., supra, and contained three intramolecular cystine disulfide bonds. The synthetic ST was that material whose specific preparation was given in Section II, above. The conjugation procedure used was the same as that discussed in Section III C, above, with the exception that the molar ratio of synthetic ST to B subunit was 70:1.

Properties of the vaccine

Vaccine properties were determined as discussed in Section III C. The concentrations at which the vaccine and unattenuated ST and B subunit yielded an absorbance of 0.600 at 410 nanometers were compared and the value for each component of the vaccine was expressed as a percentage of that of the same toxin in unattenuated form. The percentage antigenicity times 1000 yielded the value for antigen units (AU) per mg in the vaccine. The vaccine used contained 450 AU of each component toxin per milligram of protein, and immunization dosages described as 1000 AU contained this amount of antigenicity for each toxin component in 2.2 milligrams of vaccine.

Immunization procedures

Unless specified otherwise, rats were given primary immunization intraperitoneally (i.p.) using Freund's complete adjuvant (FCA) followed four days later by two p.o. boosters given at four day intervals. Peroral immunization was given via an intragastric tube 2 hours after the p.o. administration of cimetidine (sold under the trademark TAGAMET® by Smith, Kline and French Laboratories, Carolina, Puerto Rico), at a dosage of 50 milligrams/kilogram body weight, in order to ablate gastric secretion. When given p.o. in microsphere form, 1000 AU of the vaccine was encapsulated by known techniques using hydroxypropyl methylcellulose phthalate (Compound HP-50, Sinetsu Chemical, Tokyo, Japan) as the pH-sensitive coating.

Rabbits were given primary immunization either by the intramuscular (i.m.) route using FCA or by the p.o. route using an intragastric tube; this was followed two weeks later by two p.o. boosters given at two week intervals. All p.o. immunizations were preceeded 2 hours before by an i.m. injection of 30 milligrams of cimetidine.

Antitoxin response

At the time of challenge, serum and mucosal washings from challenge loops were processed [Klipstein et al., *Infect. Immun.*, 37: 1086–1092 (1982)] and antitoxin titers were determined by ELISA using reported techniques discussed in Section B, above. For antitoxin to the B subunit, the B subunit was used as the solid phase; for antitoxin to ST, goat hyperimmune antiserum to synthetic ST was used as the solid phase and synthetic ST was used as the antigen in a double sandwich technique. Since previous studies, using LT as the antigen, have shown that immunization by the i.p./p.o. approach arouses only serum immunoglobulin G(IgG) and mucosal IgA antitoxin titers [Klipstein et al., *Infect. Immun.*, 37: 1086-1092 (1982)], only antitoxin of these immunoglobulin classes were evaluated. The values reported are for the increase in the reciprocal of the geometric mean titer in four or more immunized animals over that in five unimmunized control animals, except for rabbit sera where pre- and post-immunization samples from the same animal were compared.

Challenge procedures

Immunized animals were challenged four to seven days after the final booster immunization by the instillation of graded dosages of either ST or LT into ligated ileal loops for 18 hours as described previously [Klipstein et al., *Infect. Immun.*, 31: 144-150 (1981); Sack, *Infect. Immun.*, 8: 641-648 (1973)]. The toxin was instilled in 0.5 milliliters of normal saline into a single loop in each rat and in 1.0 milliliters of Trypticase soy broth (BBL Microbiology Systems, Cockeysville, MD) in up to 10 loops in each rabbit. The values presented for each datum point of fluid secretion are the mean ± standard error of the mean (SEM) in from three to five control and immunized rats and in loops in six control rabbits and four rabbits in each immunization group. The protection index (PI) was determined by dividing that dosage of toxin in immunized animals which yielded the same secretion as the 50% effective dose ($ED_{50}$) in unimmunized animals by the value for unimmunized animals.

Rats were also challenged with 0.1 milliliter of a broth culture containing $10^9$ viable organisms of $LT^-/ST^+$ strain Tx 452 (078:H12) per milliliter. The results are expressed as the mean ± SEM percentage reduced secretion in immunized rats as compared to the value in five similarly challenged unimmunized control animals. The statistical difference between secretion in the immumized and control groups was determined by Student's t-test for two independent means.

V. USAGE OR MULTIMERIC ST

Multimeric ST molecules prepared as discussed hereinbefore were linked with a carrier molecule in determinations also carried out under the direction of Dr. Frederick A. Klipstein, supra. The results of those determinations are discussed hereinbelow.

A. Vaccines Containing Monomeric And Multimeric ST Molecules

Three vaccines were prepared. The first contained monomeric synthetic ST (hereinafter sometimes referred as M-ST), the second contained the heat-to-tail multimeric dimer ST sometimes referred herein as ST/ST, while the third vaccine contained the polymeric ST whose repeating units are linked together by intramolecular, interpolypeptide cystine disulfide bonds that is sometimes referred to as P-ST. The synthesis of each of the above materials has been described in Section II hereinbefore. Each of the ST molecules was bonded to the B subunit of *E. coli* heat-labile toxin (LT) as is discussed hereinafter in Section VI A.

Properties of Synthetic ST Preparations

When tested by the ELISA technique discussed hereinbefore using hyperimmune antisera to an M-ST conjugate, the antigenicity of non-conjugated ST/ST was 3.5-fold greater and the antigenicity of non-conjugated P-ST was 15-fold greater than that of non-conjugated M-ST. The results of these antigenicities for these determinations are illustrated in the graphs of FIG. 19.

When graded amounts of each ST preparation were tested in the suckling mouse assay, supra, values for one mouse unit were 5.7 nanograms for M-ST, 45 nanograms for ST/ST and 18.2 nanograms for P-ST. Thus, the free ST/ST had 13 percent of the secretory potency of M-ST, while P-ST had 31 percent of the secretory potency of M-ST.

Conjugation with the B Subunit

Each of the three synthetic ST preparations was cross-linked to the LT B subunit using varying initial molar ratio of ST to B subunit. The antigenicities of the conjugates so prepared are illustrated in the three graphs in FIG. 20 as a function of toxin percentage by weight and also of the initial molar ratio of the two toxins in the conjugate. It is to be understood that "cross-linking" of a toxin to a carrier is different from "cross-linking" of a polypeptide by interpolypeptide cystine disulfide bonds.

Conjugates that contained equal portions by weight of ST and B subunits were obtained from reactions in which the intial molar ratios of ST to B subunit were 45:1 for M-ST and 40:1 for ST/ST. Sufficiently large ratios of P-ST to B subunit were not utilized to yield such a conjugate.

The antigenicity of the toxins was not affected by the cross-linking reaction so that the M-ST—B subunit conjugate that contained equal proportions of each toxin component by weight had 500 antigen units of each component. In contrast, conjugates of the hyperantigenic ST preparations (ST/ST and P-ST) with approximately equal proportions of antigen units of each toxin component contained only 25 percent of ST/ST and 9 percent of P-ST by weight.

Since the proportion of weight of B subunit became reciprocally greater as the weight of ST decreased, the amount of B antigen units was greatest in those conjugates containing the least amount of ST. Among conjugates containing equal proportions of antigen units of each toxin component, the M-ST vaccine had 500 antigen units per milligram, the ST/ST vaccine contained 725 antigen units per milligram and the P-ST vaccine had 900 antigen units per milligram of each toxin component.

The residual toxicity of vaccines made from the two multimeric ST operations was 10-fold less than that of the vaccine made with M-ST. This was attributable principally to the fact that these vaccines contained smaller amounts of ST.

Although the multimeric ST preparations were less toxic initially than M-ST, their toxicities were also less strongly attenuated by the cross-linking conjugating reaction. Thus, the toxicity of each ST preparation was compared to its original value; the toxicity of M-ST was reduced 727-fold by the cross-linking reaction, that of P-ST was reduced by 256-fold and that of ST/ST was reduced by only 44-fold. Several of the properties of these vaccines are shown in Table 9 hereinbelow.

TABLE 9

Properties Of Cross-Linked Vaccines Obtained Using The B Subunit And Different Synthetic ST Preparations

| Conjugation Reaction | | Vaccine | | | | 1000 AU Vaccine | | |
|---|---|---|---|---|---|---|---|---|
| $ST^a$ | $Molar^b$ ST:B | $Wt. \%^c$ ST | B | $AU/mg^d$ ST | B | Amount $Vac^e$ | $ST^f$ | $Tox^g$ ST |
| M-ST | 45:1(0.5) | 52 | 48 | 510 | 500 | 2.00 | 1040 | 900 |
| ST/ST | 20:1(0.7) | 25 | 75 | 849 | 737 | 1.38 | 345 | 97 |

TABLE 9-continued

Properties Of Cross-Linked Vaccines Obtained Using The B Subunit And Different Synthetic ST Preparations

| Conjugation Reaction | | Vaccine | | | 1000 AU Vaccine | | |
|---|---|---|---|---|---|---|---|
| | Molar[b] | Wt. %[c] | | AU/mg[d] | | Amount | Tox[g] |
| ST[a] | ST:B | ST | B | ST | B | Vac[e] ST[f] | ST |
| P-ST | 10:1(0.9) | 9 | 91 | 1300 | 917 | 1.11  100 | 108 |

[a]ST preparations in the conjugate. M-ST = monomeric synthetic ST; ST/ST = head-to-tail dimer synthetic multimeric ST; and P-ST = polymeric ST containing interpolypeptide cystine disulfide bonds.
[b]Initial molar ratio of ST preparation to LT B subunit. Parenthesized numbers denote the weight ratio of glutaraldehyde to total protein in the reaction.
[c]Relative weight percentage of each toxin in each conjugate.
[d]Antigen units (AU) of each toxin per milligram of vaccine conjugate.
[e]Amount of vaccine conjugate in milligrams needed to provide 1000 AU of each toxin component.
[f]Amount of ST in micrograms contained in a vaccine conjugate providing 1000 AU of each toxin.
[g]Equivalent amount of unattenuated ST secretory potency in nanograms as determined by the suckling mouse assay in a vaccine conjugate containing 1000 AU of each toxin.

Immunization of Rats With ST—B Subunit Vaccines

Groups of rats were immunized with two vaccines: (i) M-ST cross-linked at an initial molar ratio of 70:1 to B subunit by the carbodiimide reaction as described hereinbefore, and in Section IV B to provide a conjugate that contained 51 percent M-ST and 49 percent B subunit by weight, and that had 450 antigen units of each toxin component per milligram; and (ii) P-ST cross-linked at an initial molar ratio of 10:1 to B subunit by the glutaraldehyde reaction (discussed in Section VI A) to provide a conjugate that contained 9 percent P-ST and 91 percent B subunit by weight, and that contained 1300 M-ST and 917 B subunit antigen units per milligram. The dosages used were based upon the amount of M-ST antigen units per milligram of each vaccine. All rats received perenteral primary immunization with 200 MST antigen units and varying dosages of peroral (p.o.) booster immunizations such that total p.o. dosages ranged between 500 and 3000 M-ST antigen units.

The response to the M-ST and P-ST conjugate-containing vaccines was identical when the total p.o. immunization total was expressed in M-ST antigen units as can be seen by an examination of FIG. 21A. When expressed as total p.o. immunizations, each vaccine raised a similar dose-dependent increase in the mucosal IgA M-ST anti-toxin response, and a similar degree of protection against a challenge with a viable LT−/ST+ of E. Coli was observed.

There was a striking difference, however, when the p.o. dosages were expressed on the basis of the amount of ST given by weight. Thus, examination of FIG. 21B illustrates that P-ST was markedly more effective; i.e., the p.o. dosage of conjugated P-ST necessary to yield 50 percent reduced secretion in challenged rats was 70 micrograms, which is 15-times less than the 1050 micrograms of conjugated M-ST needed to achieve that result.

The above results shown in Table 9 and in FIG. 21 illustrate several features of the present invention. First, both of the multimeric ST preparations had an improved antigenicity per weight over monomeric ST. In addition, both preparations showed reduced toxicity in the suckling mouse assay as free molecules and as conjugates with the LT B subunit. The highly antigenic P-ST preparation yielded a vaccine with greater antigenic potency but with substantially identical toxicity to the vaccine derived from the ST/ST. That P-ST—B subunit vaccine had nearly twice the antigenic potency of both toxin components (ST and B subunit) but only about one tenth of the residual ST toxicity of the M-ST—B subunit vaccine. Still further, the amount (380 micrograms) of P-ST needed to make a vaccine containing 1000 antigen units of each toxin component was about one-quarter of the amount (1490 micrograms) of the M-ST necessary to make such a vaccine.

It is also important to note that the antigenicity of the multimeric ST preparations as determined by ELISA correlated with their immunogenicity as determined by their effectiveness in arousing an anti-toxin response and in providing protection against the challenge in immunized experimental animals. Since the antigenicity of ST in conjugates is a function both of the proportion of ST in that conjugate and of the degree to which its antigenicity was compromised by the cross-linking conjugating reaction, expression of the dosage of the conjugate on a weight basis does not provide meaningful information unless the antigenicity is directly measured. When the antigenicity of ST is determined by a direct assay of the conjugate using an ELISA technique, and expressed in antigen units, then immunization with M-ST conjugated either to the B subunit or to an immunologically non-specific protein carrier, yields a dose-dependent response of mucosal anti-toxin levels and a degree of protection against challenge with viable toxin-produced strains Klipstein et al., Infect. Immun., 40: 924–929 (1983).

The above findings further show that immunization with either the M-ST or the P-ST vaccine raised an identical response when dosages were expressed as M-ST antigen units. Those observations also confirmed the correlation between antigenicity and immunogenicity in that P-ST was 15 times more antigenic than M-ST as determined by ELISA, and 15 times more immunogenic by weight than was M-ST in immunized rats.

The above studies also incorporated two modifications not present in previously published reports. The first was that the B subunit was obtained directly from an E. coli K-12 strain that had been modified by recombinant techniques to produce only human B subunit, rather than obtaining that subunit by dissociation procedures from the porcine LT holotoxin as has been done in the past. The second modification was that glutaraldehyde was substituted for a carbodiimide as a cross-linking reagent.

Coupling using glutaraldehyde has a number of advantages compared to couplings using carbodiimides. First, it provides effective cross-linking of ST to the B subunit without affecting the antigenicity of either toxin. Second, it yields more efficient coupling of ST to B subunit so that vaccines containing equal antigenic proportions of ST and B subunit can be derived from lower initial molar ratios of ST to B subunit, thereby significantly reducing the amount of ST needed to make the vaccine. Third, unlike carbodiimides, there is considerable experience that attests to the safety of administering glutaraldehyde conjugates to humans. [See, Cockroft et al., J. Allerg. Clin. Immunol., 60: 56–62 (1977); Levine et al., Infect. Immun., 21: 158–162 (1978); and Relyveld, Prog. Clin. Biol. Res., 47: 51–76 (1980).]

B. Further Vaccines Containing Monomeric And Polymeric ST Molecules

Further conjugates of two of the before-described three synthetic ST preparations, M-ST, and P-ST were prepared with the LT B subunit. The effects of differing initial molar ratios of the ST to B subunit, based on the molecular weight of monomeric synthetic ST (M-ST) were examined as were different coupling agents. The coupling agents utilized in this study were 1-ethyl-3-(3-dimethylaminopropyl) carbodiimide (EDAC), dimethyl suberimidate (DMS) and glutaraldehyde (GA).

Results from some of these studies are shown in the graphs of FIG. 22 for P-ST coupled with either DMS or EDAC. The results using GA are shown in the right-hand panel of FIG. 20 (panel C). As can be seen, both DMC and GA provide greater ST antigenicities (antigen units per milligram) at lower initial molar ratios of the P-ST to B subunit than are obtained using EDAC. Data for particular conjugates are shown in Table 10, below.

TABLE 10

Properties of Vaccines Prepared From The B Subunit And Different ST Preparations With Differing Coupling Agents

| Conjugation Reaction | | Vaccine | | | | 1000 AU Vaccine | | | |
|---|---|---|---|---|---|---|---|---|---|
| $ST^a$ | $Coupler^b$ | $Molar^c$ ST:B | $Wt. \%^d$ ST | B | $AU/mg^e$ ST | B | Amount $Vac^f$ | $ST^g$ | $Tox^h$ ST |
| M-ST | EDAC(1.5) | 70:1 | 51 | 49 | 492 | 467 | 2.20 | 1122 | 1276 |
| P-ST | EDAC(1.5) | 30:1 | 36 | 64 | 651 | 687 | 1.51 | 540 | 332 |
| M-ST | DMS(1.0) | 50:1 | 46 | 54 | 455 | 508 | 2.20 | 1012 | 770 |
| P-ST | DMS(1.0) | 10:1 | 12 | 88 | 1620 | 780 | 1.33 | 160 | 172 |
| M-ST | GA(0.5) | 45:1 | 52 | 48 | 510 | 500 | 2.00 | 1040 | 900 |
| P-ST | GA(0.6) | 30:1 | 30 | 70 | 4130 | 679 | 0.25 | 75 | 92 |

$^a$ST preparations used in the conjugate. M-ST = monomeric synthetic ST; and P-ST = polymeric ST containing interpolypeptide cystine disulfide bonds.
$^b$Coupling agents utilized to prepare the conjugate. EDAC = 1-ethyl-3-(3-dimethylaminopropyl) carbodiimide; DMS = dimethyl suberimidate; and GA = glutaraldehyde. Parenthesized numbers indicate the ratio by weight of coupling agent to total initial protein present in the coupling reaction medium.
$^c$Initial molar ratio of ST preparation to LT B subunit.
$^d$Relative weight of each toxin in each conjugate.
$^e$Antigen units (AU) of each toxin per milligram of vaccine conjugate.
$^f$Amount of vaccine conjugate in milligrams needed to provide 1000 AU of each toxin component.
$^g$Amount of ST by weight in micrograms contained in a vaccine conjugate providing 1000 AU of toxin.
$^h$Equivalent amount of unattenuated ST secretory potency in nanograms in a vaccine conjugate containing 1000 AU of ST toxin as determined by the suckling mouse assay.

The above data illustrate the superiority of polymeric synthetic ST (P-ST) over the monomeric synthetic ST (M-ST) on a per weight basis. That superiority does not appear to be dependent upon the coupling agent used, although the different coupling agents do show some effects. Thus, glutaraldehyde (GA) and dimethyl suberimidate (DMS) appear to provide superior conjugates of both P-ST and M-ST to the B subunit as compared to the carbodiimide (EDAC).

Experimental details regarding the above studies, in addition to those already provided, are found in Section VI B, hereinafter.

C. Immunogenicity of Non-Conjugated Polymeric ST

Each of the above-described ST preparations has been shown to be antigenic, and each is defined as having at least 10 percent of the antigenicity of the native, biologic ST on a weight basis. Those antigenicities are illustrated by ELISA determinations. In addition, the above ST preparations when coupled to a protein carrier such as the LT B subunit or porcine immunolglobulin G have been shown to be immunogenic in both rats and in rabbits. However, as far as is known, the monomeric ST (M-ST) preparations are haptenic, and are not immunogenic when used alone without a coupled carrier.

Immunization with ST as a conjugate with a carrier protein whose carrier is not an active immunogen is wasteful of resources since a portion of the conjugate is not immunologically active. The B subunit portion of ST—B subunit conjugates is of course partly immunogenic and does induce the production of antibodies. However, sufficient quantities of the holotoxin or of the B unit are not readily available to provide an economically feasible vaccine, and when produced by genetic engineering techniques, preparations of such carrier proteins may also contain unwanted protein impurities.

It would therefore be of great benefit if a totally synthetic immunogen could be prepared for a vaccine in which substantially the entire conjugate were immunologically active. The polymeric ST preparation, P-ST, because of its high average molecular weight, solubility, antigenicity and sucessful use as a coupled immunogen in a conjugate appeared to be such an immunogenically active carrier for a synthetic polypeptide corresponding in amino acid residue sequence to an immunogenic, and antigenic determinant region of the LT B subunit, such as those sequence noted in Table 2, supra. Immunogenicity studies were therefore undertaken using non-conjugated P-ST preparation as a first step toward the production of such a P-ST—LT B polypeptide conjugate.

Rabbits were immunized with non-conjugated P-ST, followed by two boosts with P-ST. ELISA determinations revealed that sera obtained from those immunizations had high titers against synthetic monomeric ST (M-ST) as an antigen. Indeed, a serum titer of 1:2500 provided one-half of the maximal saturation of the M-ST antigen.

The titers obtained are sufficient to indicate that a carrier is not needed to immunize and protect against challenge with non-conjugated P-ST. Those titers are also sufficient to suggest that P-ST can itself be used as a carrier for conjugation of an immunogenic, synthetic LT B subunit polypeptide to provide a totally synthetic immunogen, substantially all of which is immunogically active, and that provides protection against both ST- and LT-producing pathogens. It is believed that M-ST administered under the same protocol used in these studies; i.e., non-conjugated to a carrier, would induce substantially no anti-ST antibodies.

The procedures used to obtain these results are discussed in Section VI C, hereinafter.

VI. MATERIALS AND METHODS FOR MULTIMERIC ST

A. Vaccines Containing M-ST, ST/ST and P-ST Enterotoxin Preparations

Three synthetically-produced ST preparations were used. The monomeric synthetic ST (M-ST) utilized in these preparations is that material that contains the same sequence of 18 amino acid residues as that described for natural human ST Ib by Chan et al., *J. Biol. Chem.*, 256: 7744–7746 (1981), whose biologic and antigenic properties are substantially identical to those of native ST. The preparation and properties of M-ST have been discussed in Sections II and III hereinbefore. The ST/ST preparation utilized is the 36 amino acid-containing polypeptide that is the head-to-tail dimer of the 18 amino acid residue-containing human ST Ib whose preparation was discussed hereinbefore in Section II. The polymeric ST (P-ST) is that material whose plurality of ST repeating units are linked by intramolecular, interpolypeptides cystine disulfide bonds. The preparation of P-ST has also been described hereinbefore in Section II. The ST/ST and P-ST preparations were purified by passage through a Sephadex G-50 chromagotraphy column, lyophilized, and were then used without further purification.

The B subunit was obtained from cultures of *E. coli* strain pDF 87 a transformed K-12 derivative bearing the B subunit plasmid of human *E. coli* strain H 10407 [Clement et al., *Infect. Immun.*, 40: 653–658 (1983)], and was purified by the chromatographic techniques described in Clements et al., *Infect. Immun.*, 29: 91–97 (1980). The amount of toxins used was based upon their protein concentrations determined by the method of Lowry et al., *J. Biol. Chem.*, 193: 265–275 (1951); the molar equivalents were derived from published values for the native B subunit (57,400 daltons for the polymeric five subunits) and native ST (1,972 daltons), as discussed hereinbefore and in Gill et al., *Infect. Immun.*, 33: 677–682 (1981) and Staples et al., *J. Biol. Chem.*, 255: 4716–4721 (1980), respectively.

Conjugation Conditions

Three different synthetic ST preparations were cross-linked to LT B subunit by mixing varying initial molar ratios of those toxins in the presence of Sigma grade I glutaraldehyde (GA) (Sigma Chemical Co., St. Louis, MO). The ratio of GA to total protein of the toxin mixture was varied in each reaction so that the GA to B subunit ratio was kept constant at a 700:1 molar ratio. This concentration of GA has been found to provide effective cross-linking without attenuation of B subunit antigenicity. Following a two hour reaction at room temperature, the conjugates were exhaustively dialyzed against TEAN buffer (Tris, EDTA, sodium azide, sodium chloride) at four degrees C. and then processed as described hereinbefore and in Klipstein et al., *J. Infect. Dis.*, 147: 318–326 (1983).

Properties of the Conjugates

The antigenicity of the synthetic ST preparations, either alone or in conjugated form, was determined by a double sandwich enzyme-linked immunosorbant assay (ELISA) using goat and rabbit hyperimmune antisera synthetic M-ST as described in Klipstein et al., *J. Infect. Dis.*, 147: 318–326 (1983) and Klipstein et al., *Infect. Immun.*, 39: 117–121 (1983). The antigenicity of the B subunit in the conjugates was determined by ELISA using goat hyperimmune antiserum to human B subunits. The antigenicity of each toxin component of the conjugate is expressed as a percentage of that of the concomitantly-assayed respective unattenuated toxin; the percent antigenicity of each toxin component times 1000 yielded the number of its antigen units per milligram of vaccine. The antigenicity of the two multimeric ST preparations in conjugates is expressed in terms of M-ST antigen units.

Residual ST toxicity of the vaccines was determined as described previously by Klipstein et al., *Infect. Immun.*, 37: 550–557 (1982) by comparing the values for unattenuated ST. For each vaccine, the minimal effective dosage was determined in the suckling mouse assay, in which one mouse unit is defined as that amount which yields an intestinal weight to carcass weight ratio of at least 0.083.

Immunization Procedures

150–175 Gram Sprague-Dawley rats were given primary immunization intraperitoneally (i.p.) using complete Fruend's adjuvant followed by two boosters given perorally (p.o.) at 4-day intervals. Immunization p.o. was given via an intragastric tube two hours after the p.o. administration of cimetidine (TAGAMET ®) available from Smith Kline & French Laboratories, Carolina, Puerto Rico) at a dosage of 50 milligrams per kilogram of body weight to ablate gastric secretion.

Challenge Procedures

The rats were challenged four to six days after the final booster by the instillation of 0.1 milliliters of a broth culture containing $10^9$ viable organisms per milliliter of *E. coli* LT−/ST+ strain Tx 452 (O78: H12) in a single 10-centimeter ligated loop of distial ileum for 18 hours, as described hereinbefore and in Klipstein et al., *Infect. Immun.*, 34: 637–639 (1981) and in Klipstein et al., *Infect. Immun.*, 40: 924–929 (1983). Each datum point was determined in four to six immunized rats, and the results reported are for the mean (plus or minus the standard error of the mean) percentage of reduced secretion in immunized rats as compared with the value in five unimmunized control rats that were similarly challenged. A reduced secretion of greater than 50 percent represented a significant ($P$ less than 0.001) difference, as determined Student's t test for two independent means, between values in immunized and control animals.

Anti-Toxin Response

Mucosal IgA anti-toxin (mucosal AT) titers to M-ST and to the B subunit were determined by ELISA as described hereinbefore, and in Klipstein et al., *Infect. Immun.*, 37: 550–557 (1982) and in Klipstein et al., *Infect. Immun.*, 40: 924–929 (1983). Anti-toxin titers in animals immunized with P-ST vaccine were determined by a double sandwich technique in which goat hyperimmune antiserum to M-ST was used as the solid phase and M-ST was the antigen. Those results are expressed as M-ST values. The values reported are mean fold increases, rounded to the nearest integer value, in the titers of immunized rats over those of in unimmunized control rats. Anti-toxin titers in the control rats were 1:2 against both toxin components; thus, a titer of 1:64 in immunized animals represented 6-fold increase.

B. Further Vaccine Conjugates Containing Monomeric And Polymeric ST Molecules The monomeric synthetic ST (M-ST) and the polymeric synthetic ST (P-ST) preparations used in these conjugates were those whose preparations and uses have been discussed hereinbefore in Sections II, III and VI A. The LT B subunit was the material discussed in Section VI A.

Coupling of M-ST and P-ST to the B subunit using 1-ethyl-3-(3-dimethylaminopropyl) carbodiimide (EDAC) was carried out as discussed in Section IV for M-ST. Thus, the amounts of both M-ST and P-ST used were based upon both materials being monomeric.

Couplings using glutaraldehyde (GA) were carried out as described in Section VI A with the exception that the amount of GA utilized is expressed as a weight ratio of GA to total protein of the conjugate of 0.5:1 or 0.6:1, rather than the 700:1 molar ratio of GA to B subunit utilized in Section VI A.

Couplings using dimethyl suberimidate (DMS) were conducted at a DMS to total protein weight ratio of 1:1. Exemplary procedures for such couplings can be found in Carpenter et al., *J. Biol. Chem.*, 247: 5580–5586 (1972) and in Hillel et al., *Biochemistry*, 16: 3334–3342 (1977).

Antigenicities of the conjugates, the number of antigen units (AU) per milligram of conjugate, the amount of conjugate-containing vaccine to use to provide 1000 AU of the toxins and the amount of ST preparation in such a vaccine were determined as discussed in Section VI A. The secretory potency of the conjugates was determined using the before-described suckling mouse assay.

C. Immunogenicity of Non-Conjugated Polymeric ST

The polymeric synthetic ST (P-ST) used in these determinations was the material purified as discussed hereinbefore in Sections II and VI A. The immunization and ELISA protocols utilized are as follows.

Rabbits were injected intramuscularly (i.m.) on day zero with a vaccine that contained 200 micrograms of P-ST dispersed in 1.5 milliliters of complete Freund's adjuvant (CFA) and 1.0 milliliter of phosphate-buffered saline (PBS) having a pH value of 7.2. The animals received booster intraperitoneal (i.p.) injections of a vaccine that contained the same amount of P-ST contained in a 1.0 milliliters of incomplete Freund's adjuvant plus 1.0 milliliters of PBS on day 14, followed by second booster injections of a vaccine that contained the same amount of P-ST sorbed onto alum, plus 1.5 milliliters of PBS on day 27. Serum samples from the immunized rabbits were obtained by ear vein on day 34 after the first immunization.

The 18-mer monomeric synthetic ST (M-ST) whose synthesis and properties are discussed in Sections II, III and IV, and that had the amino acid residue sequence of ST Ib, supra, was used as the antigen in ELISA assays for antiserum titers. The antigen was dissolved in PBS at pH 7.2 to provide a stock solution containing 1 milligram per milliliter. That stock solution was then diluted with a 0.1 molar sodium acetate buffer having a pH value of 9.6 to provide a second stock solution containing M-ST at a concentration of 0.5 micrograms per milliliter.

50 Microliters of the second stock solution were placed into the wells of a microtiter plate, to provide 25 nanograms of the M-ST antigen to each well. The plate was then incubated in a moist chamber for a period of 2 hours at a temperature of 37° C.

The wells were then washed three times with a PBS solution that contained 0.07 percent Polysorbate 20 (TWEEN® 20; ICI United States, Inc., Wilmington, DE), followed by two washes with distilled water. 100 Microliters of 1 percent bovine serum albumin (BSA) in PBS were then added to each well to block sites of non-specific binding, and the BSA-containing solutions were incubated in the wells for 1 hour at 37° C.

Solutions containing unbound BSA were shaken from the plate. Without first drying the plate, 90 microliters of PBS were added to each well of the top row of wells, while 50 microliters of PBS were added to each well of the remainder of the plate. Thereafter, 10 microliters of anitserum were added to each of the top row of wells, and the admixture so made was mixed. 50 Microliters of antiserum-containing solution from each well was then added and mixed with the 50 microliters of PBS in the well therebelow to provide further two-fold dilutions. Similar serial two-fold dilutions were continued for the remaining wells of the plate. After all of the dilutions had been made, the diluted antiserum-containing wells were incubated at 37° C. for a period of 1 hour.

Goat anti-rabbit serum labeled with peroxidase was diluted 1:3000 by volume with PBS also containing 1 percent BSA, and 50 microliters of the resulting solution was added to each well, except for the wells of the top row that were not analyzed. The wells so prepared were incubated for a period of 1 hour at 37° C., and were then washed as described above.

A solution of ortho-phenylenediamine (OPD) was prepared by dissolving one tablet of OPD Substrate (Pittman-Moore, Inc., Washington Crossing, NJ) in 6 milliliters of distilled water to which one drop of 3 percent hydrogen peroxide was also added. 80 Microliters of the resulting solution were added to each of the microtiter plate wells. Color development in the wells was stopped after 20 minutes by the addition of 50 microliters of 4 normal sulfuric acid to each well. The amount of color present in each well was determined by measuring the optical density of the liquid therein at 492 nanometers.

The amount of antibody in the rabbit serum required to saturate one-half of the M-ST antigen on the plate was thereafter calculated using standard techniques. It was found as a result of those calculations that there was sufficient antibody to M-ST present in the immunized rabbit serum to saturate one-half of the applied M-ST antigen when that serum was diluted about 1:2500. Thus, an antiserum titer of 1:2500 was obtained by this double-sandwich ELISA determination.

VII. DIAGNOSTICS

The results discussed hereinbefore amply illustrate that the synthetic ST preparations of this invention are antigenic. For example, the monomeric synthetic ST has been shown to have an antigenicity of about 40 to about 260 percent of biologic ST when assayed using antibodies to biologic ST, and an antigenicity of about 10 to about 100 percent when measured using antibodies raised to a particular synthetic ST preparation; i.e., the purified product of preparation (3) of Table 2. Similarly, the multimeric dimer ST/ST has been shown to have an antigenicity that is about 300–350 percent of that of monomeric ST (M-ST), while the polymeric ST (P-ST) has been shown to have about 900–1500 percent the antigenicity of M-ST.

The synthetic ST molecules of this invention, and particularly the multimeric ST forms, can therefore be useful as diagnostic reagents or as part of a diagnostic system used to identify animals, including humans, that are infected with bacteria such as *E. coli* and *Klebsiella pneumoniae* that product ST toxins. Antibodies raised to the ST molecules of this invention may also be useful in such diagnostics.

Immunoassays are particularly preferred diagnostic methods of utilizing ST molecules. The ELISA determinations already discussed are exemplary of such immunoassays. Additionally, useful immunoassays include radioimmune assays and fluorescence immune assays, and the like.

One embodiment of this diagnostic system invention is particularly useful in competition assays and includes a first reagent and a second reagent in separate containers. A first reagent comprises a synthetic antigenic ST polypeptide of this invention such as M-ST or P-ST as the antigen. The second reagent comprises receptors such as antibodies that immunoreact with M-ST or P-ST and also immunoreact with biologic ST such as those discussed hereinbefore. A means for indicating the presence of an immunoreaction between the antigen and receptors is signalled by further, anti-receptor, receptors linked to a tag such as a radioactive element like $^{125}$I, a fluorescent dye like fluorescein or an enzyme like peroxidase. The indicating means is included either in a separate container as in phosphatase-linked goat-antirabbit antibodies with another separate container for its substrate, or along with the antibodies as where radioactive elements are bonded to the antibodies. The indicating means can also be separately supplied.

Admixture of predetermined amounts of the first and second reagents in the presence of a predetermined amount of a sample to be assayed such as a stool sample or a bacterial culture from a stool sample provides an amount of immunoreaction signalled by the indicating means. The amount of the immunoreaction is different from a known amount of immunoreaction when an ST is present in the assayed sample.

In usual practice, the bacterial culture is pre-incubated with the antibody and that composition is then incubated with the P-ST that is bound to the walls of an ELISA well. Rinsing of the well to remove any antibody-natural, biologic ST complex (immunoreactant) leaves an immune complex of the P-ST and antibody whose presence and amount may be signalled by the indicating means.

The use of whole, intact, biologically active antibodies is not necessary in many diagnostic systems such as the competition assay discussed immediately above. Rather, only the biologically active idiotype-containing amide portion of the antibody molecule that binds to the antigenic ST may be needed. Illustrative of the idiotype-containing polyamide portions are those known as Fab and F(ab')$_2$ antibody portions that are prepared by well-known enzymatic reactions on typically whole antibodies.

Whole, intact antibodies, Fab, F(ab')$_2$ portions and the like that contain the antibodies' idiotypic regions are denominated herein as receptors. The phrase "receptor" is used above and in the appended claims to embrace the group of such molecules as are useful in diagnostic products or techniques. However, while Fab or F(ab')$_2$ antibody portions may be utilized as the receptor of a diagnostic technique or product, use of the whole, intact antibody is usually preferred, if only because preparation of an Fab or F(ab')$_2$ portion of an antibody requires additional reaction and purification of sera.

The foregoing is intended as illustrative of the present invention but not limiting. Numerous variations and modifications may be effected without departing from the true spirit and scope of the novel concepts of the invention.

What is claimed is:

1. An antigenic synthetic polypeptide multimer comprising a plurality of polypeptide repeating units bonded together (1) head-to-tail through an amide bond formed between the amine group of the amino-terminal residue of a first polypeptide repeating unit and the carboxyl group of the carboxy-terminal residue of a second polypeptide repeating unit, or (2) by intramolecular interpolypeptide cystine disulfide bonds formed between Cys residues of said polypeptide repeating units, said synthetic multimer having at least about 10 percent of the antigenicity of that of biologic heat-stable enterotoxin of *Escherichia coli* and capable of inducing antibodies to said enterotoxin, and having thin layer chromatographic and electrophoretic mobilities different from said biologic heat-stable enterotoxin, said repeating units including the amino acid residue sequence, taken from left to right and in the direction from amino-terminus to carboxy-terminus, represented by the formula:

$$R_m^{13}-Cys(R_g^7)Cys(R_n^8)GluLeuCys(R_i^9)Cys(R_j^{10})Tyr(Asn)$$

with $R_a^1$, $R_b^2$, $R_d^4$ on respective Cys residues and $R_c^3$ below;

$$ProAlaCys(R_k^{11})Ala(Thr)GlyCys(R_l^{12})Asn(Tyr)$$

with $R_e^5$ and $R_f^6$ on respective Cys residues;

wherein the three specific amino acid residues in parentheses are each an alternative to the immediately preceding amino acid residue in said sequence;

a–f and g–l are integers each having a value of zero or one, with the proviso that if the value of any of a–f or g–l is zero, the corresponding $R_{a-f}^{1-6}$- or $R_{g-l}^{7-12}$-group is absent, and when an $R_{a-f}^{1-6}$-group is absent the sulfur atom of the respective Cys residues having an absent $R_{a-f}^{1-6}$-group forms a cystine disulfide bond, while if the value of said a–f or g–l is one, said corresponding $R_{a-f}^{1-6}$- or $R_{g-l}^{7-12}$-group is present;

said $R_{a-f}^{1-6}$-groups when taken individually, are the same or different moieties bonded to the sulfur atom of the respective Cys residues of the formula and are selected from the group consisting of hydrogen, an alkyl group containing 1 to about 4 carbon atoms, and a substituted alkyl group containing 2 to about 20 carbon atoms;

said $R_{g-l}^{7-12}$-groups are alternative Ser amino acid residues to each immediately preceding Cys residue shown in the formula;

at least two of a–f and two of g–l are zero and two Cys residues are present with the proviso that said synthetic polypeptide contains at least one intramolecular cystine disulfide bond formed from the at least two Cys residues present; and "m" is an integer having the value of zero or one with the proviso that if "m" is zero $R_m^{13}$ is absent, and if "m" is one, $R_m^{13}$ is a linking group, the acyl portion of a carboxylic acid containing 1 to about 20 carbon atoms that forms an amide bond with the amine of the amino-terminal residue, an amino acid residue, or a polypeptide chain of amino acid residues wherein the amino acid residues of said polypeptide are taken from left to right and in the direction from amino-terminus to carboxy-terminus, and selected from the group consisting of
(a) Tyr;
(b) Asn(Ser)Thr(Ser)Phe(Asn)Tyr;
(c)

$$\text{Cys}(R_g{}^7)\overset{|R_a{}^1}{\text{Cys}}(R_h{}^8)\text{GluLeuCys}(R_i{}^9)\overset{|R_d{}^4}{\text{Cys}}(R_j{}^{10})\text{Tyr(Asn)}$$
$$\overset{|}{R_c{}^3}$$

$$\text{ProAlaCys}(R_k{}^{11})\overset{|R_e{}^5}{\text{Ala(Thr)GlyCys}}(R_l{}^{12})\overset{|R_f{}^6}{\text{Asn(Tyr)}};$$

(d)

$$\text{Asn(Ser)Thr(Ser)Phe(Asn)TyrCys}(R_g{}^7)\overset{|R_a{}^1}{\text{Cys}}(R_h{}^8)\overset{|R_b{}^2}{\text{Glu}}$$

$$\text{LeuCys}(R_i{}^9)\overset{|R_d{}^4}{\text{Cys}}(R_j{}^{10})\text{Tyr(Asn)ProAlaCys}(R_k{}^{11})\overset{|R_e{}^5}{\text{Ala(Thr)Gly}}$$
$$\overset{|}{R_c{}^3}$$

$$\overset{|R_f{}^6}{\text{Cys}}(R_l{}^{12})\text{Asn(Tyr)};$$

(e)

$$\text{Asn(Ser)Thr(Ser)Phe(Asn)TyrCys}(R_g{}^7)\overset{|R_a{}^1}{\text{Cys}}(R_h{}^8)\overset{|R_b{}^2}{\text{Glu}}$$

$$\text{LeuCys}(R_i{}^9)\overset{|R_d{}^4}{\text{Cys}}(R_j{}^{10})\text{Tyr(Asn)ProAlaCys}(R_k{}^{11})\overset{|R_e{}^5}{\text{Ala(Thr)Gly}}$$
$$\overset{|}{R_c{}^3}$$

$$\overset{|R_f{}^6}{\text{Cys}}(R_l{}^{12})\text{Asn(Tyr)Asn(Ser)Thr(Ser)Phe(Asn)Tyr;}$$

(f) MetValIleIleThrPheMetSerGlyGluThrPheGlnValGluValProGlySerGlnHisIleAspSerGlnLysAsn(Ser)Thr(Ser)Phe(Asn)Tyr;
(g) TyrThrGluSerMetAlaGlyLysArgGlyAsn(Ser)Thr(Ser)Phe(Asn)Tyr;
(h) TyrThrGluSerMetAlaGlyLysArgGluMetValIleIleThrPheMetSerGlyGluThrPheGlnValGluValProGlySerGlnHisIleAspSerGlnLysAsn(Ser)Thr(Ser)Phe(Asn)Tyr;
(i) MetValIleIleThrPheMetSerGlyGluThrPheGlnValGluValProGlySerGlnHisIleAspSerGlnLys;
(j) TyrThrGluSerMetAlaGlyLysArgGly; and
(k) TyrThrGluSerMetAlaGlyLysArgGluMetValIleIleThrPheMetSerGlyGluThrPheGlnValGluValProGlySerGlnHisIleAspSerGlnLys
wherein the immediately above parenthesized amino acid residues $R_{a-f}{}^{1-6}$ and $R_{g-l}{}^{7-12}$ are as before defined;
said polypeptide having at least about 10% of the antigenicity of that of biologic heat-stable enterotoxin of *Escherichia coli* and having thin layer chromatographic and electrophoretic mobilities different from said biologic heat stable enterotoxin.

2. The synthetic polypeptide according to claim 1 wherein:

"e" is zero when "a" is zero,
"d" is zero when "b" is zero, and
"f" is zero when "c" is zero;
each of "g" and "k" is zero when "a" is zero,
each of "h" and "j" is zero when "b" is zero, and
each of "i" and "l" is zero when "c" is zero; and
an intrapolypeptide cystine disulfide bond is present between the Cys residues shown in said formula as bonded to $R_a{}^1$ and $R_e{}^5$ or $R_b{}^2$ and $R_d{}^4$ or $R_c{}^3$ and $R_f{}^6$.

3. The synthetic polypeptide according to claim 2 wherein "b" is zero and an intrapolypeptide cystine disulfide bond is present between the Cys residues shown in said formula as bonded to $R_b{}^2$ and $R_d{}^4$.

4. The synthetic polypeptide according to claim 2 wherein "b" and "c" are zero and intrapolypeptide cystine disulfide bonds are present between the Cys residues shown in said formula as bonded to $R_b{}^2$ and $R_d{}^4$, and $R_e{}^3$ and $R_f{}^6$.

5. The synthetic polypeptide according to claim 2 wherein "a", "b" and "c" are zero and three intrapolypeptide cystine disulfide bonds are present between the Cys residues shown in said formula as bonded to $R_a{}^1$ and $R_e{}^5$, $R_b{}^2$ and $R_d{}^4$, and $R_e{}^3$ and $R_f{}^6$.

6. The synthetic polypeptide according to claim 1 wherein said intramolecular cystine disulfide bond is an interpolypeptide bond and said polypeptide is one of a plurality of repeating units of a multimer.

7. The synthetic polypeptide according to claim 1 containing at least two intrapolypeptide cystine residues formed between the pairs of Cys residues shown in said formula as bonded to groups $R_a{}^1$ and $R_e{}^5$, $R_b{}^2$ and $R_d{}^4$, or $R_c{}^3$ and $R_f{}^6$.

8. The synthetic polypeptide according to claim 1 wherein "m" is zero, and $R_m{}^{13}$ is absent.

9. The synthetic multimer according to claim 1 containing about two to about three of said polypeptide repeating units, wherein said repeating units are bonded together by said amide bond and said intramolecular cystine disulfide bond is an intrapolypeptide disulfide bond.

10. The synthetic multilmer according to claim 1 having an average molecular weight of at least about 400,000 daltons, wherein said repeating units are bonded together by said intramolecular interpolypeptide cystine disulfide bonds.

11. A synthetic polypeptide having the amino acid residue sequence, taken from left to right and in the direction from amino-terminus to carboxy-terminus, represented by the formula:

AsnThrPheTyrCysCysGluLeuCysCysTyr-
ProAlaCysAlaGlyCysAsnAsnThrPheTyrCys-
CysGluLeuCysCysTyrProAlaCysAlaGlyCysAsn said polypeptide being free of sulfhydryl groups, having at least about 10% of the antigenicity of that of biologic heat stable enterotoxin of *Escherichia coli,* and thin layer chromatographic and electrophoretic mobilities different from said biologic heat-stable enterotoxin.

12. An antigenic synthetic polypeptide including the amino acid residue sequence, taken from left to right and in the direction from amino-terminus to carboxy-terminus, represented by the formula:

MetValIleIleThrPheMetSerGlyGluThrPheGlnVal-
GluValProGlySerGlnHisIleAspSerGl-
nLysAsnThrPheTyrCysCysGluLeuCysCysTyr-
ProAlaCysAlaGlyCysAsn said polypeptide being free of sulfhydryl groups, having at least about 10% of the antigenicity of that of biologic heat stable enterotoxin of *Escherichia coli* and capable of inducing antibodies to said enterotoxin, and having thin layer chromatographic and electrophoretic mobilities different from said biologic heat-stable enteroxtin.

13. An antigenic synthetic polypeptide including the amino acid residue sequence, taken from left to right and in the direction from amino-terminus to carboxy-terminus, represented by the formula:

TyrThrGluSerMetAlaGlyLysArgGluAsnThr-
PheTyrCysCysGluLeuCysCysTyr-
ProAlaCysAlaGlyCysAsn said polypeptide being free of sulfhydryl groups, having at least about 10% of the antigenicity of that of biologic heat stable enterotoxin of *Escherichia coli* and capable of inducing antibodies to said enterotoxin, and having thin layer chromatographic and electrophoretic mobilities different from said biologic heat-stable enterotoxin.

14. An antigenic synthetic polypeptide including the amino acid residue sequence, taken left to right and in the direction from amino-terminus to carboxy-terminus, represented by the formula:

$$R_m^{13}-\underset{\underset{R_c^3}{|}}{Cys}(R_g^7)\overset{\overset{R_a^1}{|}}{Cys}(R_h^8)GluLeu\overset{\overset{R_b^2}{|}}{Cys}(R_i^9)Cys(R_j^{10})Tyr(Asn)$$

$$ProAla\overset{\overset{R_e^5}{|}}{Cys}(R_k^{11})Ala(Thr)Gly\overset{\overset{R_f^6}{|}}{Cys}(R_l^{12})Asn(Tyr)$$

wherein the three specific amino acid residues in parentheses are each an alternative to the immediately preceding amino acid residue in said sequence;

a–f and g–l are integer each having a value of zero or one, with the proviso that if the value of any of a–f or g–l is zero, the corresponding $R_{a-f}^{1-6}$ or $R_{g-l}^{7-12}$-group is absent, and when an $R_{a-f}^{1-6}$-group is absent the sulfur atom of the respective Cys residues having an absent $R_{a-f}^{1-6}$-group forms a cystine disulfide bond, while if the value of said a–f or g–l is one, said corresponding $R_{a-f}^{1-6}$- or $R_{g-l}^{7-12}$-group is present;

said $R_{a-f}^{1-6}$-groups when taken individually, are the same or different moieties bonded to the sulfur atom of the respective Cys residues of the formula and are selected from the group consisting of hydrogen, an alkyl group containing 1 to about 4 carbon atoms, and a substituted alkyl group containing 2 to about 20 carbon atoms;

said $R_{g-l}^{7-12}$-groups are alternative Ser amino acid residues to each immediately preceding Cys residue shown in the formula;

at least two of a–f and two of g–l are zero and two Cys residues are present with the proviso that said synthetic polypeptide contains at least one intramolecular cystine disulfide bond formed from at least two Cys residues present; and "m" is an integer having the value of zero or one with the proviso that if "m" is zero $R_m^{13}$ is absent, and if "m" is one, $R_m^{13}$ is a linking group, the acyl portion of a carboxylic acid containing 1 to about 20 carbon atoms that forms an amide bond with the amine of the amino-terminal residue, an amino acid residue or a polypeptide chain of amino acid residues wherein the amino acid residues of said polypeptide are taken from left to right and in the direction from amino-terminus to carboxy-terminus, and selected from the group consisting of (a) Tyr;

(b)

$$\overset{\overset{R_a^1}{|}}{Cys}(R_g^7)\overset{\overset{R_b^2}{|}}{Cys}(R_h^8)GluLeu\overset{\overset{}{}}{Cys}(R_i^9)\overset{\overset{R_d^4}{|}}{Cys}(R_j^{10})Tyr(Asn)$$
$$\underset{R_c^3}{|}$$

$$ProAla\overset{\overset{R_e^5}{|}}{Cys}(R_k^{11})Ala(Thr)Gly\overset{\overset{R_f^6}{|}}{Cys}(R_l^{12})Asn(Tyr);$$

(c)

$$Asn(Ser)Thr(Ser)Phe(Asn)Tyr\overset{\overset{R_a^1}{|}}{Cys}(R_g^7)\overset{\overset{R_b^2}{|}}{Cys}(R_h^8)Glu$$

$$Leu\overset{\overset{}{}}{Cys}(R_i^9)\overset{\overset{R_d^4}{|}}{Cys}(R_j^{10})Tyr(Asn)ProAla\overset{\overset{R_e^5}{|}}{Cys}(R_k^{11})Ala(Thr)Gly$$
$$\underset{R_c^3}{|}$$

$$\overset{\overset{R_f^6}{|}}{Cys}(R_l^{12})Asn(Tyr);$$

(d)

$$Asn(Ser)Thr(Ser)Phe(Asn)Tyr\overset{\overset{R_a^1}{|}}{Cys}(R_g^7)\overset{\overset{R_b^2}{|}}{Cys}(R_h^8)Glu$$

$$Leu\overset{\overset{R_c^3}{|}}{Cys}(R_i^9)\overset{\overset{R_d^4}{|}}{Cys}(R_j^{10})Tyr(Asn)ProAla\overset{\overset{R_e^5}{|}}{Cys}(R_k^{11})Ala(Thr)Gly$$

$$\overset{\overset{R_f^6}{|}}{Cys}(R_l^{12})Asn(Tyr)Asn(Ser)Thr(Ser)Phe(Asn)Tyr;$$

(d) MetValIleIleThrPheMetSerGlyGluThr
PheGlnValGluValProGlySerGlnHisIleAsp-
SerGlnLysAsn(Ser)Thr(Ser)Phe(Asn)Tyr;

(f) TyrThrGluSerMetAlaGlyLysArgGlyAsn-
(Ser)Thr(Ser)Phe(Asn)Tyr;

(g) TyrThrGluSerMetAlaGlyLysArgGlyAsn-
(Ser)Thr(Ser)Phe(Asn)Tyr;

(h) TyrThrGluSerMetAlaGlyLysArgGluMet-
ValIleIleThrPheMetSerGlyGluThrPheGlnVal-
GluValProGlySerGlnHisIleAspSerGlnLysAsn-
(Ser)Thr(Ser)Phe(Asn)Tyr;

(i) MetValIleIleThrPheMetSerGlyGluThr-
PheGlnValGluValProGlySerGlnHisIleAsp-
SerGlnLys;

(j) TyrThrGluSerMetAlaGlyLysArgGly; and (k) TyrThrGluSerMetAlaGlyLysArgGluMet-
ValIleIleThrPheMetSerGlyGluThrPheGlnVal-
GluVlProGlySerGlnHisIleAspSerGlnLys wherein the immediately above parenthesized amino acid residues, $R_{a-f}^{1-6}$ and $R_{g-l}^{7-12}$ are as before defined;

said polypeptide having at least about 10% of the antigenicity of that of biologic heat-stable enterotoxin of *Escherichia coli* and capable of inducing antibodies to said enterotoxin, and having thin layer chromatographic and electrophoretic mobilities different from said biologic heat stable enterotoxin.

15. An antigenic synthetic polypeptide including the amino acid sequence taken from left to right in the direction from amino-terminus to carboxy-terminus, represented by the formula:

$$R_m^{13}\text{Asn(Ser)Thr(Ser)Phe(Asn)TyrCysCysGluLeuCysCys}$$
$$\text{Tyr(Asn)Pro Ala(Thr)CysAlaGlyCysAsn(Tyr)}$$

wherein lines connecting two Cys residues represent intramolecular disulfide bonds of cystine residues;
the six specific amino acid residues in parentheses are each an alternative to the immediately preceding amino acid residue;
$R_m^{13}$ is a linking group, the acyl portion of a carboxylic acid containing 1 to about 20 carbon atoms that forms an amide bond with the amine of the amino-terminal residue, or a polypeptide corresponding in sequence to a polypeptide, taken from left to right and in the direction from amino-terminus to carboxy-terminus, selected from the group consisting of
MetValIleIleThrPheMetSerGlyGluThrPheGln-ValGluValProGlySerGlnHisIleAspSerGlnLys; TyrThrGluSerMettAlaGlyLysArgGly; and TyrThrGlusSerMetAlaGlyLysARgGluMet-ValIleIleThrPheMetSerGlyGluThrPheGlnVal-GluValProGlySerGlnHisIleAspSerGlnLys
said polypeptide having at least about 10% of the antigenicity of that of biologic heat-stable enterotoxin of *Escherichia coli* and capable of inducing antibodies to said enterotoxin, and having thin layer chromatographic and electrophoretic mobilities different from said biologic heat stable enterotoxin.

16. An antigenic synthetic network polymer having at least about 10% of the antigenicity of that of heat-stable enterotoxin of *Escherichia coli* and capable of inducing antibodies to said enterotoxin comprising a plurality of polypeptide repeating units including the amino acid residue sequence, taken left to right and in the direction from amino-terminus to carboxy-terminus, represented by the formula:

$$R_m^{13}\text{—Cys}(R_g^7)\text{Cys}(R_n^8)\text{GluLeuCys}(R_1^9)\text{Cys}(R_j^{10})\text{Tyr(Asn)}$$
$$R_c^3$$
$$R_e^5 \quad R_f^6$$
$$\text{ProAlaCys}(R_k^{11})\text{Ala(Thr)GlyCys}(R_l^{12})\text{Asn(Tyr)}$$

wherein the three specific amino acid residues in parentheses are each an alternative to the immediately preceding amino acid residue in said sequence;
a-f and g-l are integers each having a value of zero or one, with the proviso that if the value of any of a-f or g-l is zero, the corresponding $R_{a-f}^{1-6}$- or $R_{g-l}^{7-12}$-group is absent, and when an $R_{a-f}^{1-6}$-group is absent the sulfur atom of the Cys residue having an absent $R_{1-f}^{1-6}$-group forms a cystine disulfide bond, while if the value of said a-f or g-l is one, said corresponding $R_{a-f}^{1-6}$- or $R_{g-l}^{7-12}$- group is present;
said $R_{a-f}^{1-6}$ groups when taken individually, are the same or different moieties bonded to the sulfur atom of the Cys residue and are selected from the group consisting of hydrogen, an alkyl group containing 1 to about 4 carbon atoms, and a substituted alkyl group containing 2 to about 20 carbon atoms;
said $R_{g-l}^{7-12}$ groups are alternative Ser amino acid residues to each immediately preceding Cys residue;
at least two of a-f and two of g-l are zero and two Cys residues are present with the proviso that said synthetic polypeptide contains at last one intramolecular cystine disulfide bond formed from the at least two Cys residues present; and
"m" is an integer having the value of zero or one with the proviso that if "m" is zero $R_m^{13}$ is absent, and if "m" is one, $R_m^{13}$ is a linking group, the acyl portion of a carboxylic acid containing 1 to about 20 carbon atoms that forms an amide bond with the amine of the amino-terminal residue, an amino acid residue or a polypeptide chain of amino acid residues wherein the amino acid residues of said polypeptide are taken from left to right and in the direction from amino-terminus to carboxy-terminus, and selected from the group consisting of
(a) Tyr;
(b) Asn(Ser)Thr(Ser)Phe(Asn)Tyr;
(c)

$$\overset{R_a^1}{|}\quad\overset{R_b^2}{|}\quad\quad\overset{R_d^4}{|}$$
$$\text{Cys}(R_g^7)\text{Cys}(R_h^8)\text{GluLeuCys}(R_i^9)\text{Cys}(R_j^{10})\text{Tyr(Asn)}$$
$$\overset{R_c^3}{|}$$

$$\overset{R_e^5}{|}\quad\quad\overset{R_f^6}{|}$$
$$\text{ProAlaCys}(R_k^{11})\text{Ala(Thr)GlyCys}(R_l^{12})\text{Asn(Tyr)};$$

(d)

$$\overset{R_a^1}{|}\quad\overset{R_b^2}{|}$$
$$\text{Asn(Ser)Thr(Ser)Phe(Asn)TyrCys}(R_g^7)\text{Cys}(R_h^8)\text{Glu}$$

$$\overset{R_d^4}{|}\quad\quad\overset{R_e^5}{|}$$
$$\text{LeuCys}(R_i^9)\text{Cys}(R_j^{10})\text{Tyr(Asn)ProAlaCys}(R_k^{11})\text{Ala(Thr)Gly}$$
$$\overset{R_c^3}{|}$$

$$\overset{R_f^6}{|}$$
$$\text{Cys}(R_l^{12})\text{Asn(Tyr)};$$

(e)

$$\overset{R_a^1}{|}\quad\overset{R_b^2}{|}$$
$$\text{Asn(Ser)Thr(Ser)Phe(Asn)TyrCys}(R_g^7)\text{Cys}(R_h^8)\text{Glu}$$

$$\overset{R_c^3}{|}\quad\overset{R_d^4}{|}\quad\quad\overset{R_e^5}{|}$$
$$\text{LeuCys}(R_i^9)\text{Cys}(R_j^{10})\text{Tyr(Asn)ProAlaCys}(R_k^{11})\text{Ala(Thr)Gly}$$

$$\overset{R_f^6}{|}$$
$$\text{Cys}(R_l^{12})\text{Asn(Tyr)Asn(Ser)Thr(Ser)Phe(Asn)Tyr};$$

(f) MetValIleIleThrPheMetSerGlyGluThrPheGlnValGluValProGlySerGlnHisIleAspSerGlnLysAsn(Ser)Thr(Ser)Phe(Asn)Tyr;

(g) TyrThrGluSerMetAlaGlyLysArgGlyAsn(Ser)Thr(Ser)Phe(Asn)Tyr;

(h) TyrThrGluSerMetAlaGlyLysArgGluMetValIleIleThrPheMetSerGlyGluThrPheGlnValGluValProGlySerGlnHisIleAspSerGlnLysAsn(Ser)Thr(Ser)Phe(Asn)Tyr;

(i) MetValIleIleThrPheMetSerGlyGluThrPheGlnValGluValProGlySerGlnHisIleAspSerGlnLys;

(j) TyrThrGluSerMetAlaGlyLysArgGly; and (k) TyrThrGluSerMetAlaGlyLysArgGluMetValIleIleThrPheMetSerGlyGluThrPheGlnValGluValProGlySerGlnHisIleAspSerGlnLys wherein the immediately above parenthesized amino acid residues, $R_{a-f}^{1-6}$ and $R_{g-l}^{7-12}$ are as before defined;

said plurality of repeating units being bonded together by cross-links supplied by intramolecular, interpolypeptide cystine disulfide bonds.

17. An antigenic synthetic network polymer comprising a plurality of polypeptide repeating units, said synthetic polymer having at least about 10% of the antigenicity of that of biologic heat-stable enterotoxin of *Escherichia coli* and capable of inducing antibodies to said enterotoxin, having thin layer chromatographic and electrophoretic mobilities different from said biologic heat-stable enterotoxin, being free of sulfhydryl group and having an average molecular weight of at least about 40,000 daltons, said repeating units including the amino acid residue sequence, taken from left to right and in the direction from amino-terminus to carboxy-terminus, represented by the formula:

Asn(Ser)Thr(Ser)Phe(Asn)TyrCysCysGluLeuCysCys

Tyr(Asn)ProAla(Thr)CysAlaGlyCysAsn(Tyr)

wherein the six specific amino acid residues in parentheses are each an alternative to the immediately preceding amino acid residue;

said repeating units being bonded together by intramolecular, interpolypeptide cystine disulfide bonds formed between the Cys residues of said polypeptide repeating units.

18. The antigenic network polymer according to claim 17 wherein said polypeptide repeating unit includes the amino acid residue sequence, taken from left to right and in the direction from amino-terminus to carboxy-terminus, represented by the formula:

AsnThrPheTyrCysCysGluLeuCysCysTyrProAlaCysAlaGlyCysAsn.

19. The synthetic network polymer according to claim 16 wherein:
all of said a–f are zero;
all of said g–l are zero;
said "m" is one; and
said $R_m^{13}$ is a peptide containing the amino acid residue sequence of the four amino-terminal residues of ST Ib.

* * * * *